(12) United States Patent
Bangera et al.

(10) Patent No.: US 9,456,777 B2
(45) Date of Patent: *Oct. 4, 2016

(54) SYSTEMS, METHODS, AND DEVICES FOR ASSESSING MICROBIOTA OF SKIN

(71) Applicant: Elwha LLC, Bellevue, WA (US)

(72) Inventors: Mahalaxmi G. Bangera, Renton, WA (US); Michael H. Baym, Cambridge, MA (US); Roderick A. Hyde, Redmond, WA (US); Jordin T. Kare, Seattle, WA (US); Eric C. Leuthardt, St. Louis, MO (US); Gary L. McKnight, Bothell, WA (US); Tony S. Pan, Cambridge, MA (US); Katherine E. Sharadin, Redmond, WA (US); Elizabeth A. Sweeney, Seattle, WA (US); Clarence T. Tegreene, Mercer Island, WA (US); Lowell L. Wood, Jr., Bellevue, WA (US)

(73) Assignee: Elwha LLC, Bellevue, WA (US)

( * ) Notice: Subject to any disclaimer, the term of this patent is extended or adjusted under 35 U.S.C. 154(b) by 572 days.

This patent is subject to a terminal disclaimer.

(21) Appl. No.: 13/975,067

(22) Filed: Aug. 23, 2013

(65) Prior Publication Data

US 2015/0054944 A1 Feb. 26, 2015

(51) Int. Cl.
*G06K 9/00* (2006.01)
*A61B 5/00* (2006.01)
*A61B 10/02* (2006.01)

(52) U.S. Cl.
CPC ............. *A61B 5/443* (2013.01); *A61B 10/02* (2013.01); *A61B 5/0077* (2013.01); *A61B 5/6803* (2013.01)

(58) Field of Classification Search
CPC .... A61B 5/443; A61B 10/02; A61B 5/0077; A61B 5/6803
USPC ........................................................ 382/100
See application file for complete search history.

(56) References Cited

U.S. PATENT DOCUMENTS 4,384,288 A 5/1983 Walton
5,077,210 A * 12/1991 Eigler .................... C12N 11/06
435/176

(Continued)

FOREIGN PATENT DOCUMENTS

JP 2002-284618 A 10/2002
WO WO 2008/059274 A1 5/2008

(Continued)

OTHER PUBLICATIONS

Ozalp et al., Antimicrobialaptamers for detection and inhibition of microbial pathogen growth, Mar. 2013.*

(Continued)

*Primary Examiner* — John Strege

(57) ABSTRACT

Devices, systems, and methods for assessing microbiota of skin are described which include: a skin-covering material with an inner surface conforming in shape to a topography of a skin surface and including a plurality of specific microbe-binding elements; an image capture device to capture an image of the inner surface of the skin-covering material and to transform the image into a digital output including information associated with at least one property and a spatial distribution of at least one type of microbe bound to the specific microbe-binding elements; and a computing device including circuitry configured to receive the digital output from the image-capture device, compare the at least one property of the at least one type of microbe bound to the specific microbe-binding elements with a database of reference microbe properties, and generate a digital profile including the at least one property and the spatial distribution of the at least one type of microbe bound to the specific microbe-binding elements.

28 Claims, 29 Drawing Sheets

(56) References Cited

U.S. PATENT DOCUMENTS

| | | | |
|---|---|---|---|
| 5,728,028 A * | 3/1998 | Dusch | A63B 23/03 424/78.03 |
| 5,747,022 A * | 5/1998 | Slavtcheff | A61K 8/0212 424/401 |
| 6,106,457 A | 8/2000 | Perkins et al. | |
| 6,199,557 B1 | 3/2001 | Laughlin | |
| 6,255,461 B1 | 7/2001 | Mosbach et al. | |
| 6,291,234 B1 | 9/2001 | Raz et al. | |
| 6,371,370 B2 | 4/2002 | Sadler et al. | |
| 6,379,920 B1 * | 4/2002 | El-Sayed | C12Q 1/02 435/29 |
| 6,433,244 B1 * | 8/2002 | Roe | A61F 13/42 604/359 |
| 6,797,522 B1 | 9/2004 | Still et al. | |
| 6,802,811 B1 | 10/2004 | Slepian | |
| 6,905,692 B2 | 6/2005 | Farmer | |
| 7,070,590 B1 | 7/2006 | Santini, Jr. et al. | |
| 7,215,976 B2 | 5/2007 | Brideglall | |
| 7,303,875 B1 | 12/2007 | Bock et al. | |
| 7,314,453 B2 | 1/2008 | Kuo | |
| 7,319,038 B2 | 1/2008 | Southard | |
| 7,386,333 B1 | 6/2008 | Birecki et al. | |
| 7,413,567 B2 | 8/2008 | Weckwerth et al. | |
| 7,494,465 B2 | 2/2009 | Brister et al. | |
| 7,507,402 B1 | 3/2009 | Farmer et al. | |
| 7,931,592 B2 | 4/2011 | Currie et al. | |
| 8,028,708 B2 | 10/2011 | Molema et al. | |
| 8,041,147 B2 | 10/2011 | Molnar et al. | |
| 8,109,875 B2 | 2/2012 | Gizewski | |
| 8,260,010 B2 | 9/2012 | Chhibber et al. | |
| 8,358,348 B2 * | 1/2013 | Mohammadi | A61B 5/442 348/207.1 |
| 8,385,619 B2 | 2/2013 | Soenksen | |
| 8,475,789 B2 * | 7/2013 | Bisgaard-Frantzen | A23C 3/08 424/130.1 |
| 8,557,560 B2 | 10/2013 | Jiménez et al. | |
| 9,028,846 B2 * | 5/2015 | Eddy | A01N 33/12 424/400 |
| 9,186,278 B2 | 11/2015 | Baym et al. | |
| 2003/0007942 A1 * | 1/2003 | Koenig | A61K 8/19 424/70.1 |
| 2003/0108896 A1 * | 6/2003 | Vogt | C12Q 1/6886 435/6.16 |
| 2003/0173525 A1 * | 9/2003 | Seville | G01N 21/6447 250/458.1 |
| 2003/0225362 A1 | 12/2003 | Currie et al. | |
| 2004/0078219 A1 | 4/2004 | Kaylor et al. | |
| 2004/0111035 A1 | 6/2004 | Kondoh et al. | |
| 2004/0125996 A1 | 7/2004 | Eddowes et al. | |
| 2004/0202685 A1 | 10/2004 | Manzo | |
| 2004/0223985 A1 | 11/2004 | Dunfield et al. | |
| 2005/0019291 A1 | 1/2005 | Zolotarsky et al. | |
| 2005/0171434 A1 | 8/2005 | Madden et al. | |
| 2006/0037197 A1 | 2/2006 | Hawes et al. | |
| 2006/0048278 A1 * | 3/2006 | Pitsolis | A45D 44/002 2/206 |
| 2006/0052739 A1 | 3/2006 | Henley et al. | |
| 2006/0172318 A1 | 8/2006 | Medinz et al. | |
| 2006/0257993 A1 | 11/2006 | McDevitt et al. | |
| 2007/0134337 A1 * | 6/2007 | Villanueva | A61L 2/02 424/489 |
| 2007/0134649 A1 | 6/2007 | Kolari et al. | |
| 2008/0060148 A1 | 3/2008 | Pinyayev et al. | |
| 2008/0139974 A1 | 6/2008 | Da Silva | |
| 2008/0262321 A1 | 10/2008 | Erad et al. | |
| 2008/0262576 A1 * | 10/2008 | Creamer | A61N 5/0616 607/88 |
| 2009/0001012 A1 * | 1/2009 | Kepner | A01N 25/34 210/287 |
| 2009/0041727 A1 | 2/2009 | Suzuki et al. | |
| 2009/0186342 A1 | 7/2009 | Bruno et al. | |
| 2009/0286263 A1 * | 11/2009 | Graham | C07K 16/065 435/7.21 |
| 2010/0055161 A1 * | 3/2010 | Ahn | A61K 8/0212 424/449 |
| 2010/0074872 A1 | 3/2010 | Blaser et al. | |
| 2010/0185064 A1 | 7/2010 | Bandic et al. | |
| 2010/0204802 A1 | 8/2010 | Wilson et al. | |
| 2010/0239625 A1 * | 9/2010 | Puckett | A41D 13/1115 424/402 |
| 2010/0331641 A1 | 12/2010 | Bangera et al. | |
| 2011/0035898 A1 | 2/2011 | Marek et al. | |
| 2011/0117025 A1 * | 5/2011 | Dacosta | A61B 5/0059 424/9.6 |
| 2011/0212485 A1 | 9/2011 | Mitragotri et al. | |
| 2011/0245094 A1 | 10/2011 | Washburn et al. | |
| 2011/0274676 A1 | 11/2011 | Farmer et al. | |
| 2012/0058464 A1 | 3/2012 | Ermantraut et al. | |
| 2012/0065086 A1 * | 3/2012 | Benson | C12Q 1/6806 506/9 |
| 2012/0092461 A1 | 4/2012 | Fisker et al. | |
| 2012/0171193 A1 * | 7/2012 | Blaser | A61K 35/74 424/130.1 |
| 2012/0241391 A1 * | 9/2012 | Carlson | A01N 25/10 210/808 |
| 2013/0078298 A1 | 3/2013 | Av-Gay et al. | |
| 2013/0079605 A1 | 3/2013 | Bandaru et al. | |
| 2013/0084259 A1 | 4/2013 | Lee | |
| 2013/0115317 A1 | 5/2013 | Charbonneau et al. | |
| 2013/0218024 A1 | 8/2013 | Boctor et al. | |
| 2013/0317741 A1 | 11/2013 | Brashear et al. | |
| 2013/0338039 A1 | 12/2013 | Mazed et al. | |
| 2014/0037688 A1 | 2/2014 | Berkes et al. | |
| 2014/0309662 A1 | 10/2014 | Brewer et al. | |
| 2015/0054944 A1 * | 2/2015 | Bangera | A61B 5/443 348/135 |
| 2015/0054945 A1 * | 2/2015 | Bangera | G01N 33/56911 348/135 |
| 2015/0148684 A1 | 5/2015 | Baym et al. | |
| 2015/0148685 A1 | 5/2015 | Baym et al. | |
| 2015/0339513 A1 * | 11/2015 | Bolea | C12Q 1/04 382/133 |

FOREIGN PATENT DOCUMENTS

| | | |
|---|---|---|
| WO | WO 2008/086596 A1 | 7/2008 |
| WO | WO 2010/093503 A2 | 8/2010 |
| WO | WO 2010/094976 A1 | 8/2010 |
| WO | WO 2011/103144 A1 | 8/2011 |
| WO | WO 2012/044794 A2 | 4/2012 |
| WO | WO 2013/070893 A1 | 5/2013 |

OTHER PUBLICATIONS

Author unknown, Wikipedia article for Antibody Mimetic, obtained from wayback machine Feb. 6, 2011.*

Chawla et al.; "An overview of passive RFID"; IEEE Applications & Practice; Sep. 2007; pp. 11-17; IEEE.

Didenko et al.; "Horseradish peroxidase-driven fluorescent labeling of nanotubes with quantum dots"; Biotechniques; NIH Public Access Author Manuscript; Mar. 2006; pp. 295-302; vol. 40; No. 3.

Finkenzeller, Klaus; "RFID Handbook. Fundamentals and Applications in Contactless Smart Cards and Identification"; printed on Apr. 16, 2014; pp. 29-59; John Wiley & Sons, Ltd.

Hagleitner et al.; "Smart single-chip gas sensor microsystem"; Nature; Nov. 15, 2001; pp. 293-296; vol. 414; Macmillan Magazines Ltd.

Kumar et al.; "AnimalLectinDB: An integrated animal lectin database"; Bioinformation; published Apr. 22, 2011; pp. 134-136; vol. 6; No. 3; Biomedical Informatics.

Mohanty et al.; "Micro Electrical Impedance Spectroscopy of Bovine Chromaffin Cells"; printed on Nov. 14, 2013; pp. 1-5.

Snow et al.; "Chemical Detection with a Single-Walled Carbon Nanotube Capacitor"; Science; Mar. 25, 2005; pp. 1942-1945; vol. 307; American Association for the Advancement of Science.

Sun et al.; "Broadband single cell impedance spectroscopy using maximum length sequences: theoretical analysis and practical considerations"; Measurement Science and Technology; 2007; pp. 2589-2868; vol. 18; IOP Publishing Ltd, UK.

(56) References Cited

OTHER PUBLICATIONS

Yusa et al.; "Controlled multiple quantum coherences of nuclear spins in a nanometre-scale device"; Nature; Apr. 21, 2005; pp. 1001-1005; vol. 434; Nature Publishing Group.

Adak et al.; "Bishydrazide Glycoconjugates for Lectin Recognition and Capture of Bacterial Pathogens"; Bioconjug Chem; Nov. 17, 2010; pp. 1-27; vol. 21; No. 11.

Alexander et al.; "Molecular imprinting science and technology: a survey of the literature for the years up to and including 2003"; Journal of Molecular Recognition; Jan. 4, 2006; pp. 106-180; vol. 19; John Wiley & Sons, Ltd.

Ammor, Mohammed Salim; "Recent Advances in the Use of Intrinsic Fluorescence for Bacterial Identification and Characterization"; J Fluoresc; Mar. 12, 2007; pp. 1-5; Springer Science + Business Media, LLC.

Baddour et al.; "High Frequency Ultrasound Imaging of Changes in Cell Structure Including Apoptosis"; PDF created on Aug. 12, 2013; pp. 1-6; IEEE.

Barlen et al.; "Detection of *Salmonella* by Surface Plasmon Resonance"; Sensors; Aug. 7, 2007; pp. 1427-1446; vol. 7; MDPI.

Bernardini et al.; "The 3D Model Acquisition Pipeline"; Computer Graphics Forum; 2002; pp. 149-172; vol. 21; No. 2; The Eurographics Association and Blackwell Publishers Ltd.

Bhatta et al.; "Use of Fluorescence Spectroscopy to Differentiate Yeast and Bacterial Cells"; Applied Microbiology and Biotechnology; 2006; pp. 121-126; vol. 71; No. 1.

Blank et al.; "A force-based protein biochip"; PNAS; Sep. 30, 2003; pp. 11356-11360; vol. 100; No. 20; The National Academy of Sciences of the USA.

Bouchard et al.; "Optical characterization of Pseudomonas fluorescens on meat surfaces using time-resolved fluorescence"; Journal of Biomedical Optics; Jan./Feb. 2006; pp. 014011-1-014011-7; vol. 11; No. 1.

Brennan, John D.; "Preparation and Entrapment of Fluorescently Labeled Proteins for the Development of Reagentless Optical Biosensors"; Journal of Fluorescence; Apr. 28, 1999; pp. 295-312; vol. 9; No. 4; Plenum Publishing Corporation.

Bright et al.; "Regenerable Fiber-Optic-Based Immunosensor"; Analytical Chemistry; May 15, 1990; pp. 1065-1069; vol. 62, No. 10; American Chemical Society.

Cady et al.; "Optimized linkage and quenching strategies for quantum dot molecular beacons"; Molecular and Cellular Probes; 2007; pp. 116-124; vol. 21; Elsevier Ltd.

Cao et al.; "Molecular Beacon Aptamers for Protein Monitoring in Real-Time and in Homogeneous Solutions"; Current Proteomics; 2005; pp. 31-40; vol. 2; Bentham Science Publishers Ltd.

Chen et al.; "Aptamer from whole-bacterium SELEX as new therapeutic reagent against virulent Mycobacterium tuberculosis"; Biochemical and Biophysical Research Communications; Apr. 11, 2007; pp. 743-748; vol. 357; Elsevier Inc.

Cho et al.; "The Human Microbiome: at the interface of health and disease"; Nat Rev Genet; Oct. 1, 2012; pp. 260-270; vol. 13; No. 4.

Chung et al.; "Size Comparisons among Integral Membrane Transport Protein Homologues in Bacteria, Archaea, and Eucarya"; Journal of Bacteriology; Feb. 2001; pp. 1012-1021; vol. 183; No. 3; American Society for Microbiology.

Cockburn et al.; "High throughput DNA sequencing to detect differences in the subgingival plaque microbiome in elderly subjects with and without dementia"; Investigative Genetics; 2012; pp. 1-12; vol. 3; No. 19; Cockburn et al, Biomed Central Ltd.

Cole et al.; "The Ribosomal Database Project: improved alignments and new tools for rRNA analysis"; Nucleic Acids Research; published online Nov. 12, 2008; pp. D141-D145; vol. 37; The Author(s).

Cowan et al.; "Development of engineered biofilms on poly-L-lysine patterened surfaces"; Biotechnology Letters; Accepted May 23, 2001; pp. 1235-1241; vol. 23; Kluwer Academic Publishers; Netherlands.

Crawford et al.; "Peptide aptamers: Tools for biology and drug discovery"; Briefings in Functional Genomics and Proteomics; Apr. 2003; pp. 72-79; vol. 2; No. 1; Henry Stewart Publications.

Crowe et al.; "Candida albicans binds human plasminogen: identification of eight plasminogen-binding proteins"; Molecular Microbiology; 2003; pp. 1637-1651; vol. 47; No. 6; Blackwell Publishing Ltd.

De Château et al.; "Protein PAB, an Albumin-binding Bacterial Surface Protein Promoting Growth and Virulence"; The Journal of Biological Chemistry; revised Jul. 22, 1996; pp. 26609-26615; vol. 271; No. 43; Issue of Oct. 25, 1996; The American Society for Biochemistry and Molecular Biology, Inc.; USA.

Dewhirst et al.; "The Human Oral Microbiome"; Journal of Bacteriology; Accepted Jul. 10, 2010; pp. 5002-5017; vol. 192; No. 19; American Society for Microbiology.

Doornbos et al.; "White Blood Cell Differentiation Using a Solid State Flow Cytometer"; Cytometry; accepted Mar. 16, 1993; pp. 589-594; vol. 14; Wiley-Liss, Inc.

Dwarakanath et al.; "Quantum dot-antibody and aptamer conjugates shift fluorescence upon binding bacteria"; Biochemical and Biophysical Research Communications; Received Oct. 11, 2004; pp. 739-743; vol. 325; Elsevier Inc.

Elston, Dirk M.; "Fluorescence of fungi in superficial and deep fungal infections"; BMC Microbiology; Sep. 24, 2001; pp. 1-4; vol. 1; No. 21; Elston.

Fan et al.; "Sensitive optical biosensors for unlabeled targets: A review"; Analytica Chimica Acta; 2008; pp. 8-26; vol. 620; Elsevier B.V.

Fan et al.; "Structures in Bacillus subtilis Are Recognized by CD14 in a Lipopolysaccharide Binding Protein-Dependent Reaction"; Infection and Immunity; Jun. 1999; pp. 2964-2968; vol. 67; No. 6; American Society for Microbiology.

Fei-Fei et al.; "One-Shot Learning of Object Categories"; IEEE Transactions on Pattern Analysis and Machine Intelligence; Apr. 2006; pp. 594-611; vol. 28; No. 4; IEEE Computer Society.

Feng et al.; "Computer-assisted technique for the design and manufacture of realistic facial prostheses"; British Journal of Oral and Maxillofacial Surgery; 2010; pp. 105-109; vol. 48; The British Association of Oral and Maxillofacial Surgeons.

Freeman et al.; "Chemiluminescent and Chemiluminescence Resonance Energy Transfer (CRET) Detection of DNA, Metal Ions, and Aptamer—Substrate Complexes Using Hemin/G-Quadruplexes and CdSe/ZnS Quantum Dots"; Journal of the American Chemical Society; 2011; pp. 11597-11604; vol. 133; American Chemical Society.

Gaitanis et al.; "The Malassezia Genus in Skin and Systemic Diseases"; Clinical Microbiology Reviews; Jan. 2012; pp. 106-141; vol. 25; No. 1; American Society for Microbiology.

Gao et al.; "A Micro Sensing Probe for Detecting Individual Biological Cells"; Proceedings of the $25^{th}$ Annual International Conference of the IEEE EMBS, Cancun, Mexico; Sep. 17-21, 2003; pp. 3348-3351; IEEE.

Gauglitz et al.; "Host Defence Against Candida albicans and the Role of Pattern-recognition Receptors"; Acta Derm Venereol; 2012; pp. 291-298; vol. 92; The Authors; Journal Compilation: Acta Dermato-Venereologica.

Giana et al.; "Rapid Identification of Bacterial Species by Fluorescence Spectroscopy and Classification Through Principal Components Analysis"; Journal of Fluorescence; Nov. 2003; pp. 489-493; vol. 13, No. 6; Plenum Publishing Corporation.

Gopinath et al.; "Aptamer That Binds to the gD Protein of Herpes Simplex Virus 1 and Efficiently Inhibits Viral Entry"; Journal of Virology; Jun. 2012; pp. 6732-6744; vol. 86; No. 12; American Society for Microbiology.

Graham, Anna R.; "Fungal Autofluorescence with Ultraviolet Illumination"; American Journal of Clinical Pathology; Feb. 1983; pp. 231-234; vol. 79; No. 2; American Society of Clinical Pathologists.

Grice et al.; "A diversity profile of the human skin microbiota"; Genome Research; 2008; pp. 1043-1050; vol. 18; Cold Spring Harbor Laboratory Press.

(56) References Cited

OTHER PUBLICATIONS

Grice et al.; "The skin microbiome"; Nature Reviews—Microbiology; Apr. 2011; pp. 244-253; vol. 9; Macmillan Publishers Limited.
Griffen et al.; "Core: A Phylogenetically-Curated 16S rDNA Database of the Core Oral Microbiome"; PLoS One; Apr. 2011; pp. 1-10; vol. 6; Issue 4; Griffen et al.
Harz et al.; "Vibrational Spectroscopy—A Powerful Tool for the Rapid Identification of Microbial Cells at the Single-Cell Level"; Cytometry Part A Journal of the International Society for Advancement of Cytometry; 2009; pp. 104-113; vol. 75A; International Society for Advancement of Cytometry.
Helm et al.; "Classification and identification of bacteria by Fourier-transform infrared spectroscopy"; Journal of General Microbiology; 1991; pp. 69-79; vol. 137; SGM; Printed in Great Britain.
Hildebrand et al.; "Acoustic microscopy of living cells"; Proc. Natl. Acad. Sci.; Mar. 1981; pp. 1656-1660; vol. 78; No. 3.
Hilton, Peter J.; "Laser induced fluorescence imaging of bacteria"; SPIE; PDF created on Aug. 12, 2013; pp. 1174-1178; vol. 3491.
Hornyak, Tim; "RFID Powder"; Scientific American; Feb. 2008; pp. 68-71; Scientific American, Inc.
Huff et al.; "Light-scattering sensor for real-time identification of Vibrio parahaemolyticus, Vibrio vulnificus and Vibrio cholera colonies on solid agar plate"; Microbial Biotechnology; 2012; pp. 607-620; vol. 5, No. 5; The Authors; Microbial Biotechnology-Society for Applied Microbiology and Blackwell Publishing Ltd.
Ikanovic et al.; "Fluorescence Assay Based on Aptamer-Quantum Dot Binding to Bacillus Thuringiensis Spores"; J Fluoresc; 2007; pp. 193-199; vol. 17; Springer Science + Business Media, LLC.
Jaiswal et al.; "Long-term multiple color imaging of live cells using quantum dot bioconjugates"; Nature Biotechnology; Jan. 2003; pp. 47-51; vol. 21; Nature Publishing Group; www.nature.com/naturebiotechnology.
Jhaveri et al.; "In vitro selection of signaling aptamers"; Nature Biotechnology; Dec. 2000; pp. 1293-1297; vol. 18; Nature America Inc.
Kashyap et al.; "Surface Plasmon Resonance-Based Fiber and Planar Waveguide Sensors"; Journal of Sensors; Accepted Jun. 26, 2009; pp. 1-9; vol. 2009; Hindawi Publishing Corporation.
Kim et al.; "Lens-Free Imaging for Biological Applications"; Journal of Laboratory Automation; Jan. 27, 2012; pp. 43-49; vol. 17; No. 1; Society for Laboratory Automation and Screening.
Knappik et al.; "Fully Synthetic Human Combinatorial Antibody Libraries (HuCAL) Based on Modular Consensus Frameworks and CDRs Randomized with Trinucleotides"; J. Mol. Biol.; 2000; pp. 57-86; vol. 296; Academic Press.
Koenig et al.; "Laser-Induced Autofluorescence for Medical Diagnosis"; Journal of Fluorescence; 1994; pp. 17-40; vol. 4; No. 1; Plenum Publishing Corporation.
Koo et al.; "Development of a Streptavidin-Conjugated Single-Chain Antibody That Binds Bacillus cereus Spores"; Applied and Environmental Microbiology; Jul. 1998; pp. 2497-2502; vol. 64; No. 7; American Society for Microbiology.
Kupper et al.; "Generation of human antibody fragments against *Streptococcus* mutans using a phage display chain shuffling approach"; BMC Biotechnology; Jan. 25, 2005; pp. 1-12; vol. 5; No. 4; Kupper et al.
Lee et al.; "A micro-machined LC-resonator for high-frequency magnetic sensor applications"; Intermag 2006; Downloaded on Nov. 17, 2009; pp. 1.
Lee et al.; "Graphene-Based Chemiluminescence Resonance Energy Transfer for Homogeneous Immunoassay"; ACS NANO; 2012; pp. 2978-2983; vol. 6; No. 4; American Chemical Society.
Liu et al.; "Deep Sequencing of the Oral Microbiome Reveals Signatures of Periodontal Disease"; PLos One; Jun. 2012; pp. 1-16; vol. 7; Issue 6; Liu et al.
Low et al.; "A DNA Aptamer Recognizes the Asp f 1 Allergen of Aspergillus fumigatus"; Biochem Biophys Res Commun.; Aug. 28, 2009; pp. 544-548; vol. 386; No. 3; Elsevier Inc.
Majid et al.; "Integration of stereophotogrammetry and triangulation-based laser scanning system for precise mapping of craniofacial morphology"; The International Archives of the Photogrammetry, Remote Sensing and Spatial Information Sciences; 2008; pp. 805-812; vol. XXXVII; Part B5; Beijing.
Markiewicz et al.; "The Use of 3D Imaging Tools in Facial Plastic Surgery"; Facial Plast Surg Clin N. Am; 2011; pp. 655-682; vol. 19; Elsevier Inc.
Martin et al.; "Learning to Detect Natural Image Boundaries Using Local Brightness, Color, and Texture Cues"; IEEE Transactions on Pattern Analysis and Machine Intelligence; May 2004; pp. 530-549; vol. 26; No. 5; IEEE Computer Society.
Mateus et al.; "Adherence of Candida albicans to Silicone Induces Immediate Enhanced Tolerance to Fluconazole"; Antimicrobial Agents and Chemotherapy; Sep. 2004; pp. 3358-3366; vol. 48; No. 9; American Society for Microbiology.
Meerwaldt et al.; "Skin Autofluorescence, a Measure of Cumulative Metabolic Stress and Advanced Glycation End Products, Predicts Mortality in Hemodialysis Patients"; Journal of the American Society of Nephrology; 2005; pp. 3687-3693; vol. 16; American Society of Nephrology.
Modlin, Robert L.; "Innate Immunity. Ignored for decades, but not forgotten"; J Invest Dermatol.; Mar. 2012; pp. 882-886; vol. 132; No. 3.
Mohan et al.; "Bokode: Imperceptible Visual tags for Camera Based Interaction from a Distance"; PDF created on Aug. 12, 2013; pp. 1-8; http://cameraculture.media.mit.edu/bokode.
Murakami et al.; "A miniature confocal optical microscope with mems gimbal scanner"; Transducers '03; The $12^{th}$ International Conference on Solid State Sensors, Actuators and Microsystems, Boston, Jun. 8-12, 2003; pp. 587-590; IEEE.
Nakatsuji et al.; "Antibodies Elicited by Inactivated Propionibacterium acnes-Based Vaccines Exert Protective Immunity and Attenuate the IL-8 Production in Human Sebocytes: Relevance to Therapy for Acne Vulgaris"; Journal of Investigative Dermatology; published online May 8, 2008; pp. 2451-2457; vol. 128; The Society for Investigative Dermatology.
Nitsche et al.; "One-step selection of Vaccinia virus-binding DNA aptamers by MonoLEX"; BMC Biotechnology; published Aug. 15, 2007; pp. 1-12; vol. 7; No. 48; Nitsche et al.
Oberreuter et al.; "Identification of coryneform bacteria and related taxa by Fourier-transform infrared (FT-IR) spectroscopy"; International Journal of Systematic and Evolutionary Microbiology; 2002; pp. 91-100; vol. 52; IUMS.
Peppas et al.; "Polymers and Gels as Molecular Recognition Agents"; Pharmaceutical Research; May 2002; pp. 578-587; vol. 19; No. 5; Plenum Publishing Corporation.
Proske et al.; "Aptamers—basic research, drug development, and clinical applications"; Appl Microbiol Biotechnol; Published online Nov. 11, 2005; pp. 367-374; vol. 69; Springer-Verlag.
Quast et al.; "The SILVA ribosomal RNA gene database project: improved data processing and web-based tools"; Nucleic Acids Research; Published Nov. 28, 2012; pp. D590-D596; vol. 41; The Author(s) 2012; Oxford University Press.
Raghavan et al.; "BIAcore: a microchip-based system for analyzing the formation of macromolecular complexes"; Structure; Apr. 15, 1995; pp. 351-333; vol. 3; No. 4; Current Biology Ltd.
Rucker et al.; "Functional Antibody Immobilization on 3-Dimensional Polymeric Surfaces Generated by Reactive Ion Etching"; Langmuir; In Final Form Jun. 2, 2005; pp. 7621-7625; vol. 21; American Chemical Society.
Seidl et al.; "Opto-mechanical combination of a line scanning camera and a micro laser scanner system"; PDF created on Aug. 12, 2013; pp. 1-6.
Selinummi et al.; "Software for quantification of labeled bacteria from digital microscope images by automated image analysis"; BioTechniques; Dec. 2005; pp. 859-863; vol. 39; No. 6.
Shimobaba et al.; "Gigapixel inline digital holographic microscopy using a consumer scanner"; Physics Optics; May 27, 2013; pp. 1-6; Optical Society of America.
Son et al.; "An implantable wireless microdosimeter for radiation oncology"; MEMS 2008, Tucson, AZ, USA; Jan. 13-17, 2008; pp. 256-259; IEEE.

(56) References Cited

OTHER PUBLICATIONS

Spear et al.; "Isolation, characterization, and recovery of small peptide phage display epitopes selected against viable malignant glioma cells"; Cancer Gene Therapy; Received Mar. 5, 2001; pp. 506-511; vol. 8, No. 7; Nature Publishing Group.

Sun et al.; "An Enhanced Active Shape Model for Facial Features Extraction"; 2008 11th IEEE International Conference on Communication Technology Proceedings; 2008; pp. 661-664; IEEE.

Szeliski, Richard; "Image Alignment and Stitching: A Tutorial"; Computer Graphics and Vision; 2006; pp. 1-104; vol. 2; No. 1; R. Szeliski.

Tachon et al.; "Experimental conditions affect the site of tetrazolium violet reduction in the electron transport chain of Lactococcus lactis"; Microbiology; Accepted Jun. 7, 2009; pp. 2941-2948; vol. 155; SGM.

Terada et al.; "Bacterial adhesion to and viability on positively charged polymer surfaces"; Microbiology; Accepted on Aug. 22, 2006; pp. 3575-3583; vol. 152; SGM.

Ulicny, J.; "Lorenz-Mie Light Scattering in Cellular Biology"; Gen. Physiol. Biophys.; 1992; pp. 133-151; vol. 11.

Valm et al.; "Systems-level analysis of microbial community organization through combinatorial labeling and spectral imaging"; PNAS; Mar. 8, 2011; pp. 4152-4157; vol. 108; No. 10.

Van Heerbeek et al.; "Three dimensional measurement of rhinoplasty results"; Rhinology; 2009; pp. 121-125; vol. 47.

Vashist, Sandeep Kumar; "A Review of Microcantilevers for Sensing Applications"; AZojono Journal of Nanotechnology Online; Jun. 2007; pp. 1-15; vol. 3; AZoM.com Pty Ltd.

Yasuda et al.; "Lectin Microarray Reveals Binding Profiles of Lactobacillus casei Strains in a Comprehensive Analysis of Bacterial Cell Wall Polysaccharides"; Applied and Environmental Microbiology; Jul. 2011; pp. 4539-4546; vol. 77, No. 13; American Society for Microbiology.

Ye et al.; "Molecularly imprinted polymers as antibody and receptor mimics for assays, sensors and drug discovery"; Anal Bioanal Chem; Published online Jan. 22, 2004; pp. 1887-1897; vol. 378; Springer-Verlag.

Zelada-Guillen et al ; "Immediate Detection of Living Bacteria at Ultralow Concentrations Using a Carbon Nanotube Based Potentiometric Aptasensor"; Angew. Chem. Int. Ed; 2009; pp. 1-4; vol. 48; Wiley-VCH Verlag GmbH & Co. KGaA; Weinheim.

Zharov et al.; "In vivo high-speed imaging of individual cells in fast blood flow"; Journal of Biomedical Optics; Sep./Oct. 2006; pp. 054034-1-054034-4; vol. 11; No. 5; SPIE.

Zharov et al.; "In vivo Photothermal Flow Cytometry: Imaging and Detection of Individual Cells in Blood and Lymph Flow"; Journal of Cellular Biochemistry; 2006; pp. 916-932; vol. 97; Wiley-Liss, Inc.

Zheng et al.; "Enhanced active shape model for facial feature localization"; Proceedings of the Seventh International Conference on Machine Learning and Cybernetics, Kunming; Jul. 12-15, 2008; pp. 2841-2845; IEEE.

Zitova et al.; "Image registration methods: a survey"; Image and Vision Computing; accepted Jun. 2003; pp. 977-1000; vol. 21; Elsevier B.V.

PCT International Search Report; International App. No. PCT/US2014/052081; Nov. 20, 2014; pp. 1-8.

PCT International Search Report; International App. No. PCT/US2014/052077; Nov. 28, 2014; pp. 1-4.

PCT International Search Report; International App. No. PCT/US2014/052086; Nov. 28, 2014; pp. 1-3.

PCT International Search Report; International App. No. PCT/US2014/051928; Dec. 1, 2014; pp. 1-3.

PCT International Search Report; International App. No. PCT/US2014/051934; Dec. 1, 2014; pp. 1-3.

\* cited by examiner

Fig. 5
Fig. 5A
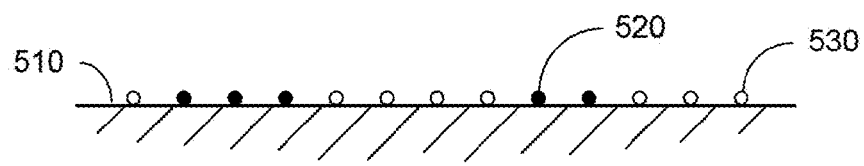
Fig. 5B
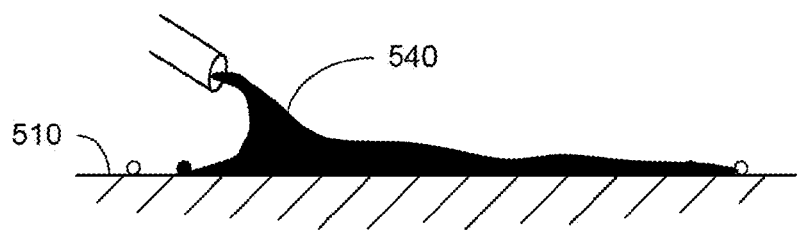
Fig. 5C
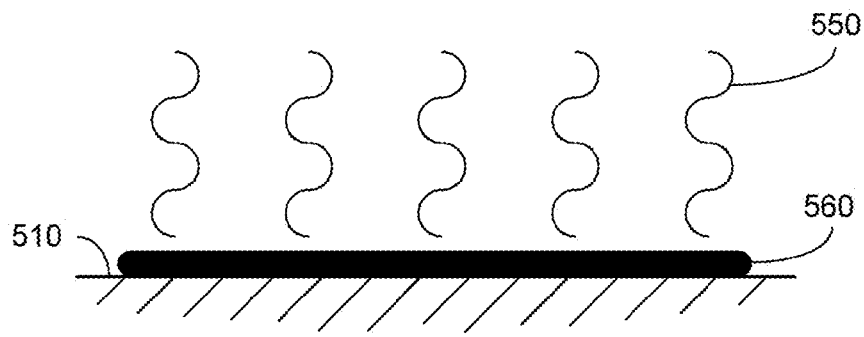
Fig. 5D
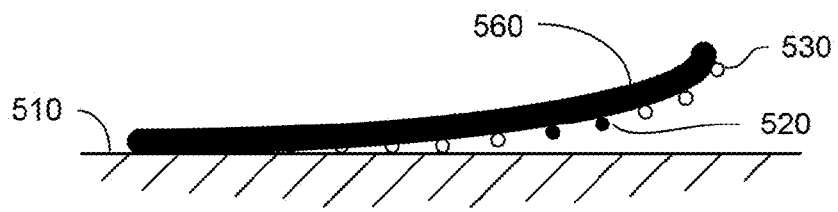
Fig. 5E
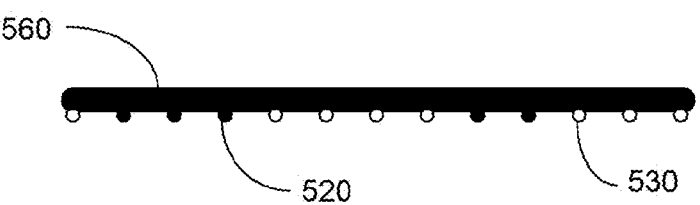

Fig. 6

600 Receiving a digital output from an image-capture device, the digital output including information associated with at least one property and a spatial distribution of at least one type of microbe captured on a microbe-capture region on an inner surface of a skin-covering material 610 Identifying the at least one type of microbe captured on the microbe-capture region by comparing the information associated with the at least one property of the at least one type of microbe with a database of reference microbe properties 620 Reporting to a user an identification and spatial profile of the identified at least one microbe captured on the microbe-capture region on the inner surface of the skin-covering material

Fig. 7

| 600 Receiving a digital output from an image-capture device, the digital output including information associated with at least one property and a spatial distribution of at least one type of microbe captured on a microbe-capture region on an inner surface of a skin-covering material |
|---|
| 700 From at least one digital camera |
| 705 From at least one scanning device |

| 610 Identifying the at least one type of microbe captured on the microbe-capture region by comparing the information associated with the at least one property of the at least one type of microbe with a database of reference microbe properties | |
|---|---|
| 710 Comparing at least one of an optical property | 715 Comparing at least one of a fluorescence property |
| 720 Comparing at least one of an infrared spectral property | 725 Comparing at least one of an acoustic property |
| 730 Comparing at least one of a reflective property | 735 Comparing at least one of a light scattering property |
| 740 Comparing at least one of an opacity property | 745 Comparing at least one of a size |
| 750 Comparing at least one of a morphological property | 755 Comparing at least one of a physical feature |

| 620 Reporting to a user an identification and spatial profile of the identified at least one microbe captured on the microbe-capture region on the inner surface of the skin-covering material |
|---|

600 Receiving a digital output from an image-capture device, the digital output including information associated with at least one property and a spatial distribution of at least one type of microbe captured on a microbe-capture region on an inner surface of a skin-covering material

---

610 Identifying the at least one type of microbe captured on the microbe-capture region by comparing the information associated with the at least one property of the at least one type of microbe with a database of reference microbe properties

---

620 Reporting to a user an identification and spatial profile of the identified at least one microbe captured on the microbe-capture region on the inner surface of the skin-covering material

---

800
Generating a digital alignment of the spatial profile of the identified at least one type of microbe captured on the microbe-capture region on the inner surface of the skin-covering material with a digital image of a skin surface of an individual covered by the microbe-capture region of the skin-covering material; and
Reporting to the user a personalized microbe profile including the identification and the spatial profile of the identified at least one type of microbe on the skin surface of the individual

| 810 Providing a visual representation of the personalized microbe profile on a display | 820 Providing a printout of the personalized microbe profile | 830 Exporting the personalized microbe profile to a computing device |

840
Comparing the personalized microbe profile with a reference microbe profile
Generating a recommended treatment regimen for the individual based on the comparison; and
Reporting the recommended treatment regimen to the user

| 850 Comparing with a reference microbe profile generated for the individual at a previous point in time | 860 Comparing with a reference microbe profile generated for one or more other individuals |

870
Generating a recommended treatment regimen based on the identification and the spatial profile of the at least one type of microbe captured on the microbe-capture region of the skin-covering material
Reporting the recommended treatment regimen to the user

1000
Applying a skin-covering material to a skin surface of an individual, the skin-covering material including an inner surface and an outer surface, the inner surface substantially conforming in shape to a topography of the skin surface of the individual and including a microbe-capture region

1010
Removing the skin-covering material from the skin surface of the individual

1020
Capturing at least one image of the inner surface of the skin-covering material with an image-capture device and transforming the captured at least one image into a digital output, the digital output including information associated with at least one type of microbe bound to the microbe-capture region

1030
Receiving the digital output from the image-capture device including information associated with the at least one property and the spatial distribution of the at least one type of microbe bound to the microbe-capture region

1040
Identifying the at least one type of microbe bound to the microbe-capture region by comparing the information associated with the at least one property of the at least one type of microbe with a database of reference microbe properties

1050
Reporting to a user an identification and spatial profile of the identified at least one microbe bound to the microbe-capture region on the inner surface of the skin-covering material

Fig. 11

| 1100 Applying a microbe-capture material to the inner surface of the skin-covering material prior to applying the skin-covering material to the skin surface of the individual |

| 1000 Applying a skin-covering material to a skin surface of an individual, the skin-covering material including an inner surface and an outer surface, the inner surface substantially conforming in shape to a topography of the skin surface of the individual and including a microbe-capture region |

| 1010 Removing the skin-covering material from the skin surface of the individual |

| 1110 Applying at least one signal-generating agent to the skin-covering material, capturing at least one image of the inner surface of the skin-covering material with the image-capture device to detect one or more signals emitted or reflected from the at least one signal-generating agent bound to one or more of the at least one type of microbe bound to the microbe-capture region; and transforming the one or more signals into a digital output |

| 1120 Separating the skin-covering material into one or more pieces along one or more tearable lines of perforation; and capturing at least one image with the image-capture device of the inner surface of at least one of the one or more pieces of the skin-covering material |

| 1020 Capturing at least one image of the inner surface of the skin-covering material with an image-capture device and transforming the captured at least one image into a digital output, the digital output including information associated with at least one type of microbe bound to the microbe-capture region |

| 1030 Receiving the digital output from the image-capture device including information associated with the at least one property and the spatial distribution of the at least one type of microbe bound to the microbe-capture region |

| 1040 Identifying the at least one type of microbe bound to the microbe-capture region by comparing the information associated with the at least one property of the at least one type of microbe with a database of reference microbe properties |

| 1130 Generating a digital alignment of the spatial profile of the identified at least one type of microbe captured on the microbe-capture region on the inner surface of the skin-covering material with a digital image of the skin surface of the individual covered by the inner surface of the skin-covering material; and reporting to the user a personalized microbe profile including the identification and the spatial profile of the identified at least one type of microbe on the skin surface of the individual |

| 1050 Reporting to a user an identification and spatial profile of the identified at least one microbe bound to the microbe-capture region on the inner surface of the skin-covering material |

| 1140 Generating a recommended treatment regimen based on the identification and the spatial profile of the at least one type of microbe bound to the microbe-capture region on the inner surface of the skin-covering material; and reporting the recommended treatment regimen to the user |

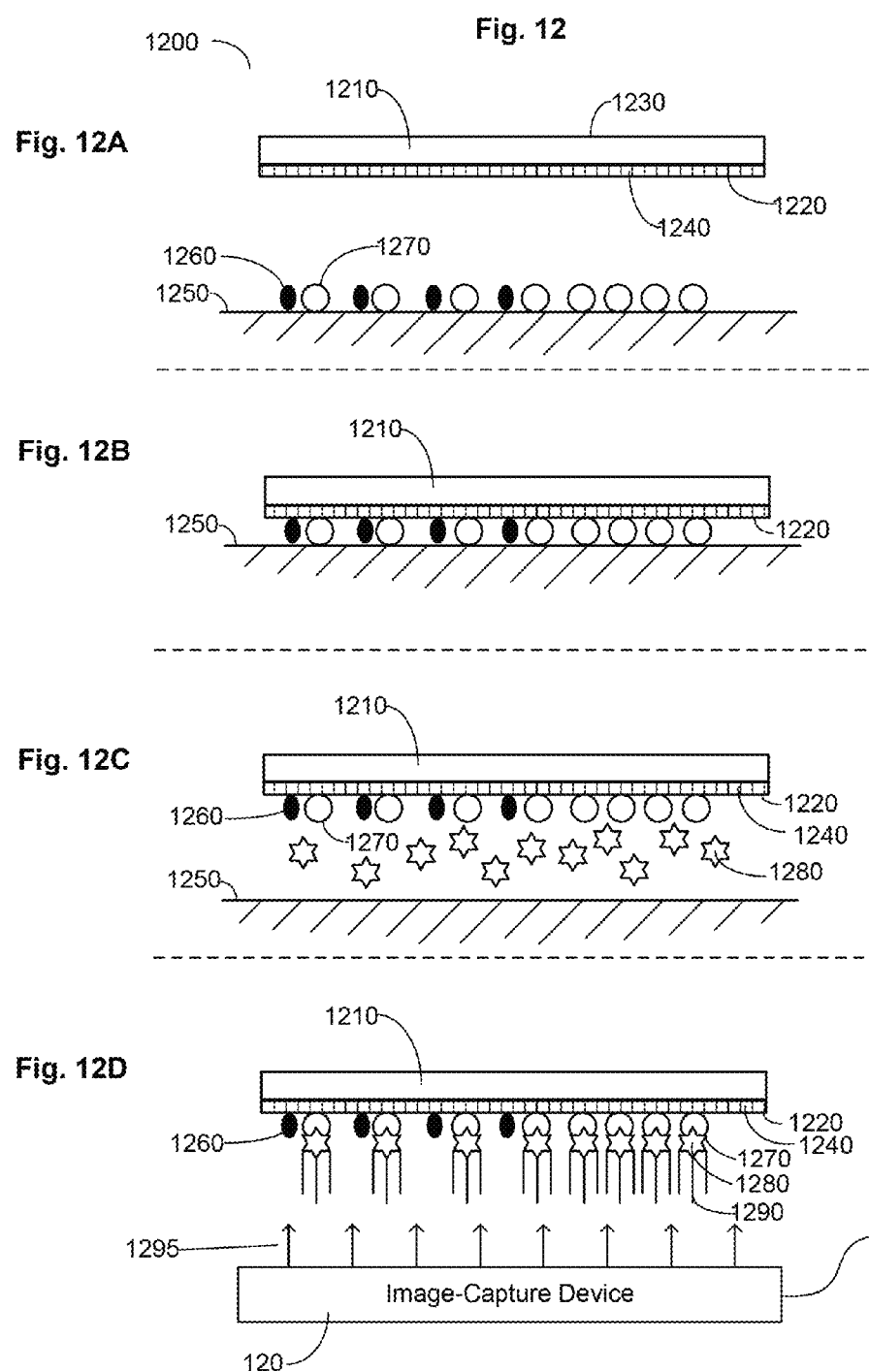

Fig. 13

1300 An article of manufacture

1310
Non-transitory machine readable media bearing one or more instructions for assessing microbiota of skin, the one or more instructions including:

1320
One or more instructions for receiving a digital output from an image-capture device, the digital output including information associated with at least one property and a spatial distribution of at least one type of microbe captured on a microbe-capture region on an inner surface of a skin-covering material

1330
One or more instructions for comparing the information associated with the at least one property of the at least one type of microbe captured on the microbe-capture region with a database of reference microbe properties

1340
One or more instructions for generating a microbe profile including the at least one property and the spatial distribution of the at least one type of microbe captured on the microbe-capture region

1350
One or more instructions for generating a recommended treatment regimen for an individual based on a comparison of the microbe profile with a reference microbe profile

1360
One or more instructions for reporting to a user at least one of the microbe profile or the recommended treatment regimen

2000
Receiving a digital output from an image-capture device, the digital output including information associated with at least one property and a spatial distribution of at least one type of microbe bound to at least one of a plurality of specific microbe-binding elements associated with an inner surface of a skin-covering material 2010
Identifying the at least one type of microbe bound to the at least one of the plurality of specific microbe-binding elements by comparing the information associated with the at least one property of the at least one type of microbe with a database of reference microbe properties 2020
Reporting to a user an identification and spatial profile of the identified at least one type of microbe bound to the at least one of the plurality of specific microbe-binding elements associated with the inner surface of the skin-covering material

Fig. 21

2000
Receiving a digital output from an image-capture device, the digital output including information associated with at least one property and a spatial distribution of at least one type of microbe bound to at least one of a plurality of specific microbe-binding elements associated with an inner surface of a skin-covering material > 2100 From at least one digital camera > 2105 From at least one scanning device

2010
Identifying the at least one type of microbe bound to the at least one of the plurality of specific microbe-binding elements by comparing the information associated with the at least one property of the at least one type of microbe with a database of reference microbe properties

| 2110 Comparing at least one of an optical property | 2115 Comparing at least one of a fluorescence property |
| --- | --- |
| 2120 Comparing at least one of an infrared spectral property | 2125 Comparing at least one of an acoustic property |
| 2130 Comparing at least one of a reflective property | 2135 Comparing at least one of a light scattering property |
| 2140 Comparing at least one of an opacity property | 2145 Comparing at least one of a size |
| 2150 Comparing at least one of a morphological property | 2155 Comparing at least one of a physical feature |

2020
Reporting to a user an identification and spatial profile of the identified at least one type of microbe bound to the at least one of the plurality of specific microbe-binding elements associated with the inner surface of the skin-covering material

Fig. 22

2000
Receiving a digital output from an image-capture device, the digital output including information associated with at least one property and a spatial distribution of at least one type of microbe bound to at least one of a plurality of specific microbe-binding elements associated with an inner surface of a skin-covering material

2010
Identifying the at least one type of microbe bound to the at least one of the plurality of specific microbe-binding elements by comparing the information associated with the at least one property of the at least one type of microbe with a database of reference microbe properties

2020
Reporting to a user an identification and spatial profile of the identified at least one type of microbe bound to the at least one of the plurality of specific microbe-binding elements associated with the inner surface of the skin-covering material

2200
Generating a digital alignment of the spatial profile of the identified at least one type of microbe bound to the at least one of the plurality of specific microbe-binding elements associated with the inner surface of the skin-covering material with a digital image of a skin surface of an individual covered by the inner surface of the skin-covering material; and
Reporting to the user a personalized microbe profile including the identification and the spatial profile of the identified at least one type of microbe on the skin surface of the individual

2210 Providing a visual representation of the personalized microbe profile on a display

2220 Providing a printout of the personalized microbe profile

2230 Exporting the personalized microbe profile to a computing device

2240
Comparing the personalized microbe profile with a reference microbe profile
Generating a recommended treatment regimen for the individual based on the comparison; and
Reporting the recommended treatment regimen to the user

2250 Comparing with a reference microbe profile generated for the individual at a previous point in time

2260 Comparing with a reference microbe profile generated for one or more other individuals

2270
Generating a recommended treatment regimen based on the identification and the spatial profile of the at least one type of microbe bound to the at least one of the plurality of specific microbe-binding elements associated with the inner surface of the skin-covering material
Reporting the recommended treatment regimen to the user

Fig. 23

2300
Receiving a first digital output from an image-capture device, the first digital output including information associated with at least one property and a spatial distribution of a first set of one or more microbes bound at a first time point to one or more of a plurality of specific microbe-binding elements on an inner surface of a first skin-covering material

2310
Receiving a second digital output from an image-capture device, the second digital output including information associated with at least one property and a spatial distribution of a second set of one or more microbes bound at a second time point to one or more of a plurality of specific microbe-binding elements on an inner surface of a second skin-covering material

2320
Comparing the first digital output with the second digital output

2330
Generating a recommended treatment regimen based on the comparison of the first digital output with the second digital output

2340
Reporting the recommended treatment regimen to a user

Fig. 24

2400
Applying a skin-covering material to a skin surface of an individual, the skin-covering material including an inner surface and an outer surface, the inner surface substantially conforming in shape to a topography of the skin surface of the individual and including associated thereto a plurality of specific microbe-binding elements 2410
Removing the skin-covering material from the skin surface of the individual 2420
Capturing at least one image of the inner surface of the skin-covering material with an image-capture device and transforming the captured at least one image into a digital output, the digital output including information associated with at least one property and a spatial distribution of at least one type of microbe bound to the at least one of the plurality of specific microbe-binding elements associated with the inner surface of the skin-covering material 2430
Receiving the digital output from the image-capture device, the digital output including the information associated with the at least one property and the spatial distribution of the at least one type of microbe bound to the at least one of the plurality of the at least one type of specific microbe-binding element associated with the inner surface of the skin-covering material 2440
Identifying the at least one type of microbe bound to the at least one of the plurality of the at least one type of specific microbe-binding element by comparing the information associated with the at least one property of the at least one type of microbe with a database of reference microbe properties 2450
Reporting to a user an identification and spatial profile of the identified at least one type of microbe bound to the at least one of the plurality of the at least one type of specific microbe-binding element associated with the inner surface of the skin-covering material

Fig. 25

> 2500 Applying the plurality of the at least one type of specific microbe-binding element to the inner surface of the skin-covering material prior to applying the skin-covering material to the skin surface of the individual 2400 Applying a skin-covering material to a skin surface of an individual, the skin-covering material including an inner surface and an outer surface, the inner surface substantially conforming in shape to a topography of the skin surface of the individual and including associated thereto a plurality of specific microbe-binding elements 2410 Removing the skin-covering material from the skin surface of the individual 2420 Capturing at least one image of the inner surface of the skin-covering material with an image-capture device and transforming the captured at least one image into a digital output, the digital output including information associated with at least one property and a spatial distribution of at least one type of microbe bound to the at least one of the plurality of specific microbe-binding elements associated with the inner surface of the skin-covering material > 2510 Separating the skin-covering material into one or more pieces along one or more tearable lines of perforations; and scanning the inner surface of at least one of the one or more pieces of the skin covering material 2430 Receiving the digital output from the image-capture device, the digital output including the information associated with the at least one property and the spatial distribution of the at least one type of microbe bound to the at least one of the plurality of the at least one type of specific microbe-binding element associated with the inner surface of the skin-covering material > 2520 Generating a digital alignment of the spatial profile of the identified at least one type of microbe bound to the at least one of the plurality of the at least one type of specific microbe-binding element associated with the inner surface of the skin-covering material with a digital image of the skin surface of the individual covered by the inner surface of the skin-covering material; and reporting to the user a personalized microbe profile including the identification and the spatial profile of the identified at least one type of microbe on the skin surface of the individual 2440 Identifying the at least one type of microbe bound to the at least one of the plurality of the at least one type of specific microbe-binding element by comparing the information associated with the at least one property of the at least one type of microbe with a database of reference microbe properties 2450 Reporting to a user an identification and spatial profile of the identified at least one type of microbe bound to the at least one of the plurality of the at least one type of specific microbe-binding element associated with the inner surface of the skin-covering material > 2530 Generating a recommended treatment regimen based on the identification and the spatial profile of the at least one type of microbe bound to the at least one of the plurality of the at least one type of specific microbe-binding element associated with the inner surface of the skin-covering material; and reporting the recommended treatment regimen to the user Fig. 26
Fig. 26A
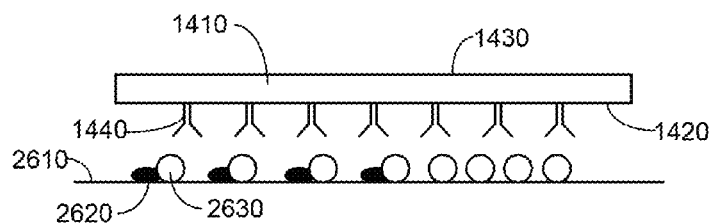
Fig. 26B
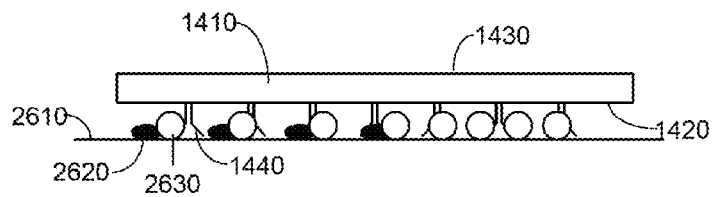
Fig. 26C
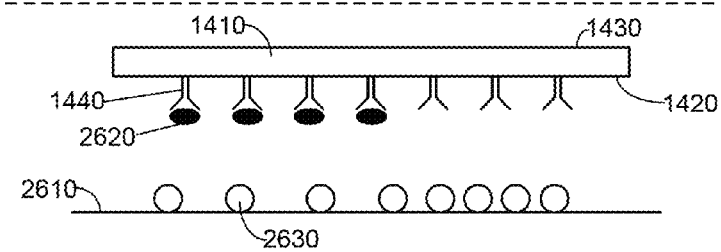
Fig. 26D
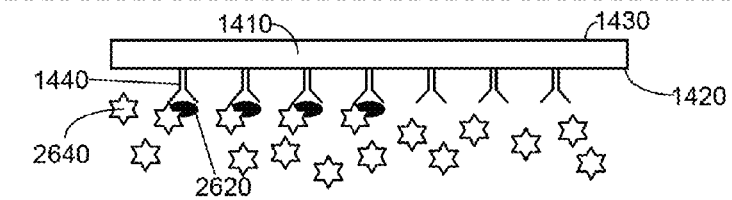
Fig. 26E
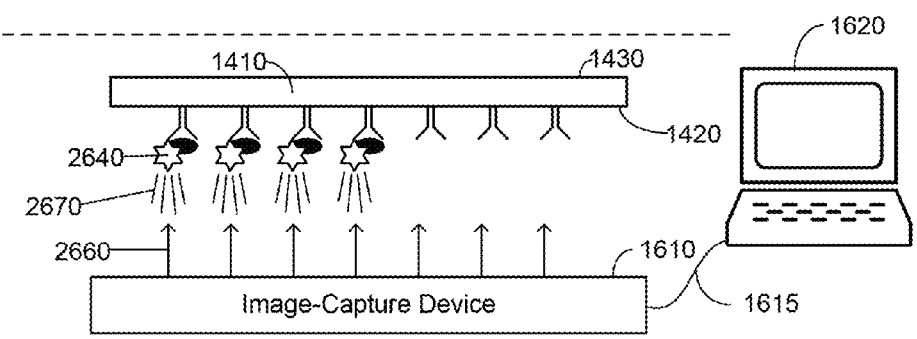

Fig. 27

| 2700 An article of manufacture |
|---|

| 2710<br>Non-transitory machine readable media bearing one or more instructions for assessing microbiota of skin, the one or more instructions including: |
|---|

| 2720<br>One or more instructions for receiving a digital output from an image-capture device, the digital output including information associated with at least one property and a spatial distribution of at least one type of microbe bound to at least one of a plurality of specific microbe-binding elements on an inner surface of a skin-covering material |
|---|
| 2730<br>One or more instructions for identifying the at least one type of microbe bound to the at least one of the plurality of specific microbe-binding elements by comparing the information associated with the at least one property of the at least one type of microbe with a database of reference microbe properties |
| 2740<br>One or more instructions for generating a digital alignment of the spatial distribution of the identified at least one type of microbe bound to the at least one of the plurality of specific microbe-binding elements on the inner surface of the skin-covering material with a digital image of a skin surface of an individual covered by the inner surface of the skin-covering material |
| 2750<br>One or more instructions for generating a personalized microbe profile from the digital alignment, the personalized microbe profile including the identity of the at least one type of microbe and the spatial distribution of the at least one type of microbe on the skin surface of the individual |
| 2760<br>One of more instructions for comparing the personalized microbe profile with a reference microbe profile |
| 2770<br>One of more instructions for generating a recommended treatment regimen for the individual based on the comparison of the personalized microbe profile with the reference microbe profile |
| 2780<br>One or more instructions for reporting to a user at least one of the personalized microbe profile or the recommended treatment regimen |

Fig. 28
Fig. 28A
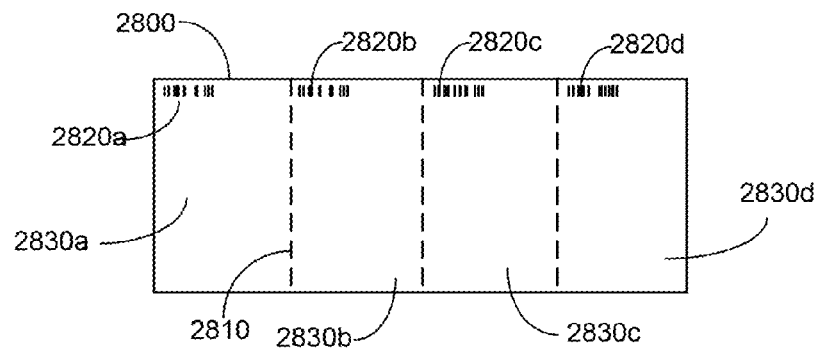
Fig. 28B
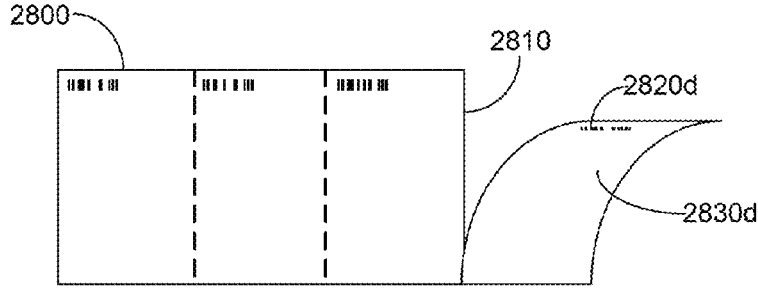
Fig. 28C
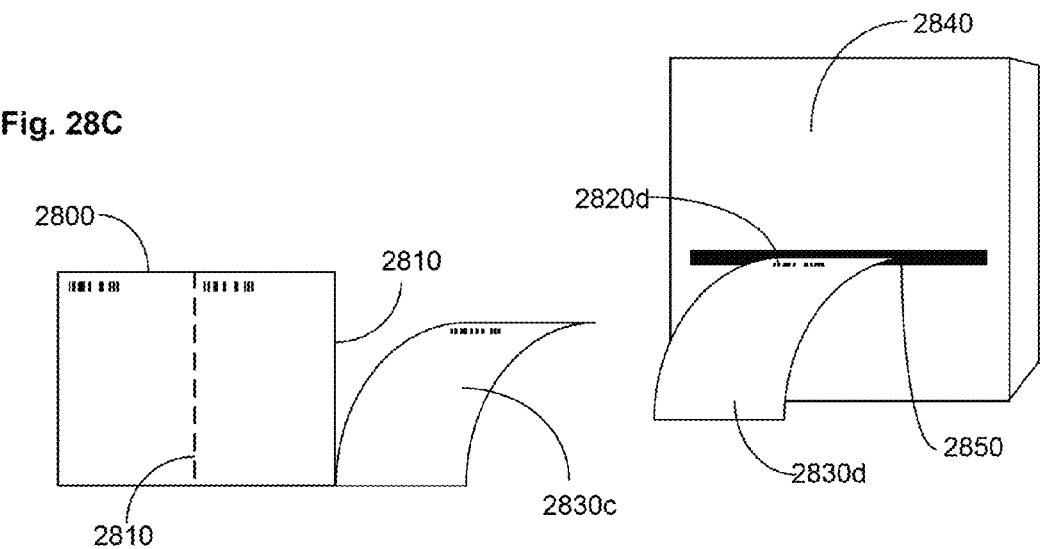

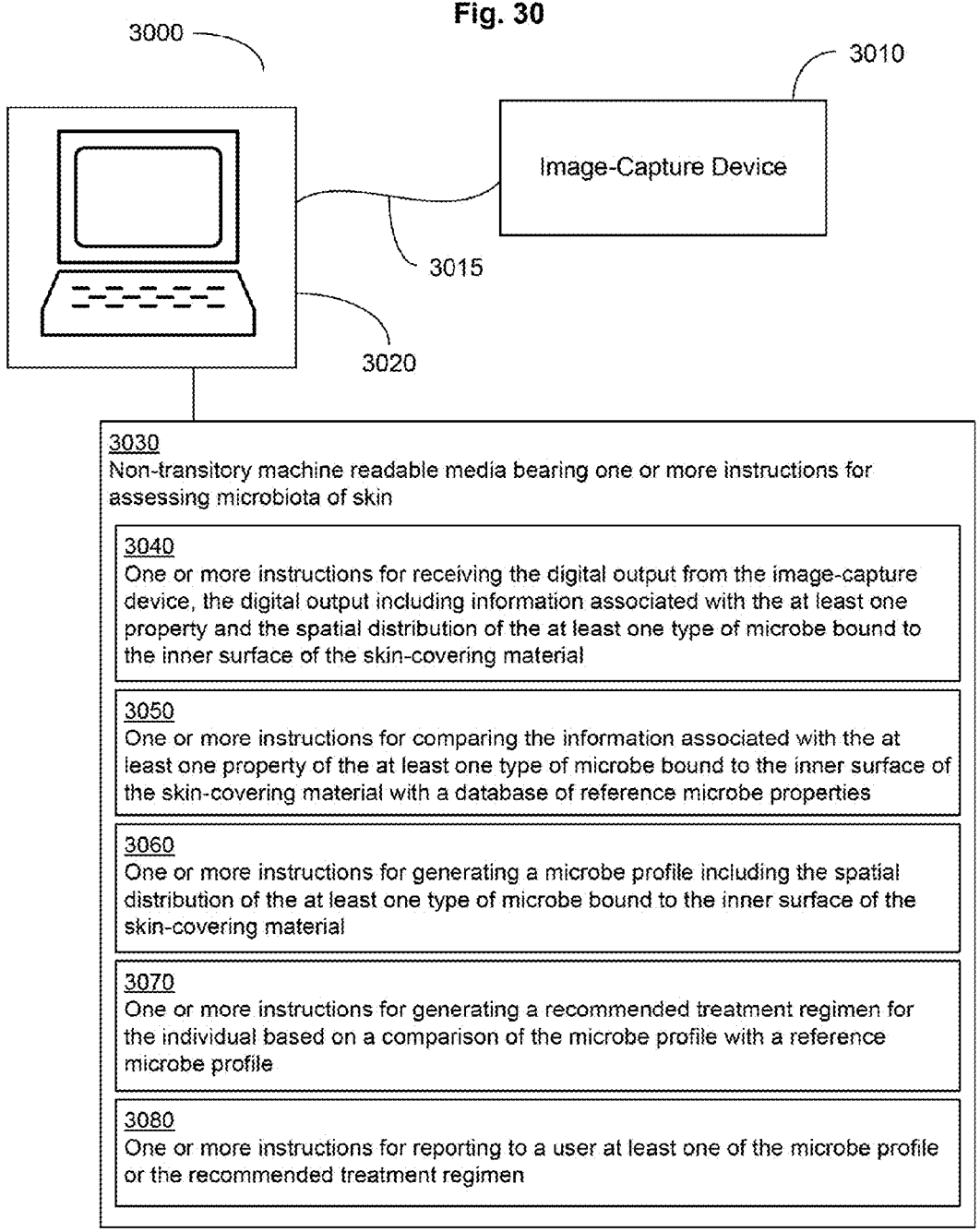

SYSTEMS, METHODS, AND DEVICES FOR ASSESSING MICROBIOTA OF SKIN

If an Application Data Sheet (ADS) has been filed on the filing date of this application, it is incorporated by reference herein. Any applications claimed on the ADS for priority under 35 U.S.C. §§119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC §119(e) for provisional patent applications, for any and all parent, grandparent, great-grandparent, etc. applications of the Priority Application(s)). In addition, the present application is related to the "Related Applications," if any, listed below.

PRIORITY APPLICATIONS

None

RELATED APPLICATIONS

U.S. patent application Ser. No. 13/975,055, entitled SYSTEMS, METHODS, AND DEVICES FOR ASSESSING MICROBIOTA OF SKIN, naming Mahalaxmi G. Bangera, Michael H. Baym, Roderick A. Hyde, Jordin T. Kare, Eric C. Leuthardt, Gary L. McKnight, Tony S. Pan, Katherine E. Sharadin, Elizabeth A. Sweeney, Clarence T. Tegreene, and Lowell L. Wood, Jr. as inventors, filed 23 Aug. 2013, is related to the present application.

U.S. patent application Ser. No. 13/975,079, entitled SYSTEMS, METHODS, AND DEVICES FOR ASSESSING MICROBIOTA OF SKIN, naming Mahalaxmi G. Bangera, Michael H. Baym, Roderick A. Hyde, Jordin T. Kare, Eric C. Leuthardt, Gary L. McKnight, Tony S. Pan, Katherine E. Sharadin, Elizabeth A. Sweeney, Clarence T. Tegreene, and Lowell L. Wood, Jr. as inventors, filed 23 Aug. 2013, is related to the present application.

If the listings of applications provided above are inconsistent with the listings provided via an ADS, it is the intent of the Applicant to claim priority to each application that appears in the Priority Applications section of the ADS and to each application that appears in the Priority Applications section of this application.

All subject matter of the Priority Applications and the Related Applications and of any and all parent, grandparent, great-grandparent, etc. applications of the Priority Applications and the Related Applications, including any priority claims, is incorporated herein by reference to the extent such subject matter is not inconsistent herewith.

SUMMARY

In an aspect, a system for assessing microbiota of skin includes, but is not limited to, a skin-covering material having an inner surface and an outer surface, the inner surface substantially conforming in shape to a topography of a skin surface of an individual and including a microbe-capture region; an image-capture device including circuitry to capture at least one image of the inner surface of the skin-covering material and to transform the captured at least one image into a digital output including information associated with at least one property and a spatial distribution of at least one type of microbe bound to the microbe-capture region; and a computing device including a processor, the computing device operably coupled to the image-capture device and including circuitry configured to receive the digital output from the image-capture device including the information associated with the at least one property and the spatial distribution of the at least one type of microbe bound to the microbe-capture region, compare the at least one property of the at least one type of microbe with a database of reference microbe properties, and generate a digital profile including the at least one property and the spatial distribution of the at least one type of microbe bound to the microbe-capture region of the skin-covering material. In addition to the foregoing, other system aspects are described in the claims, drawings, and text forming a part of the present disclosure.

In an aspect, a method includes, but is not limited to, receiving at digital output from an image-capture device, the digital output including information associated with at least one property and a spatial distribution of at least one type of microbe captured on a microbe-capture region on an inner surface of a skin-covering material; identifying the at least one type of microbe captured on the microbe-capture region by comparing the information associated with the at least one property of the at least one type of microbe with a database of reference microbe properties; and reporting to a user an identification and spatial profile of the identified at least one type of microbe captured on the microbe-capture region on the inner surface of the skin-covering material. In addition to the foregoing, other method aspects are described in the claims, drawings, and text forming a part of the present disclosure.

In an aspect, a method includes, but is not limited to, receiving a first digital output from an image-capture device, the first digital output including information associated with at least one property and a spatial distribution of a first set of one or more microbes captured at a first time point on a microbe-capture region on an inner surface of a first skin-covering material; receiving a second digital output from the image-capture device, the second digital output including information associated with at least one property and a spatial distribution of a second set of one or more microbes captured at a second time point on a microbe-capture region on an inner surface of a second skin-covering material; comparing the first digital output with the second digital output; generating a recommended treatment regimen based on the comparison of the first digital output and the second digital output; and reporting the recommended treatment regimen to a user. In addition to the foregoing, other method aspects are described in the claims, drawings, and text forming a part of the present disclosure.

In an aspect, a method includes, but is not limited to, applying a skin-covering material to a skin surface of an individual, the skin-covering material including an inner surface and an outer surface, the inner surface substantially conforming in shape to a topography of the skin surface of the individual and including a microbe-capture region; removing the skin-covering material from the skin surface of the individual; capturing at least one image of the inner surface of the skin-covering material with an image-capture device and transforming the captured at least one image into a digital output, the digital output including information associated with at least one property and a spatial distribution of at least one type of microbe bound to the microbe-capture region; receiving the digital output from the image-capture device, the digital output including information associated with the at least one property and the spatial distribution of the at least one type of microbe bound to the microbe-capture region; identifying the at least one type of microbe bound to the microbe-capture region by comparing the information associated with the at least one property of the at least one type of microbe with a database of reference microbe properties; and reporting to a user an identification and spatial profile of the identified at least one type of microbe bound to the microbe-capture region on the inner surface of the skin-covering material. In addition to the foregoing, other method aspects are described in the claims, drawings, and text forming a part of the present disclosure.

In an aspect, an article of manufacture includes, but is not limited to, non-transitory machine readable media bearing one or more instructions for assessing microbiota of skin, the one or more instructions including one or more instructions for receiving a digital output from an image-capture device, the digital output including information associated with at least one property and a spatial distribution of at least one type of microbe captured on a microbe-capture region on an inner surface of a skin-covering material; one or more instructions for comparing the information associated with the at least one property of the at least on type of microbe captured on the microbe-capture region with a database of reference microbe properties; one or more instructions for generating a microbe profile including the at least one property and the spatial distribution of the at least one type of microbe captured on the microbe-capture region; one or more instructions for generating a recommended treatment regimen for an individual based on a comparison of the microbe profile with a reference microbe profile; and one or more instructions for reporting to a user at least one of the microbe profile or the recommended treatment regimen. In addition to the foregoing, other aspects of the article of manufacture are described in the claims, drawings, and text forming a part of the present disclosure.

In an aspect, a device includes, but is not limited to, a skin-covering material having an inner surface and an outer surface, the inner surface substantially conforming in shape to a topography of a skin surface of an individual and including associated thereto a plurality of specific microbe-binding elements. In addition to the foregoing, other device aspects are described in the claims, drawings, and text forming a part of the present disclosure.

In an aspect, a system for assessing microbiota of skin includes, but is not limited to, a skin-covering material having an inner surface and an outer surface, the inner surface substantially conforming in shape to a topography of a skin surface of an individual and including associated thereto a plurality of specific microbe-binding elements; an image-capture device including circuitry to capture at least one image of the inner surface of the skin-covering material and to transform the captured at least one image into a digital output including information associated with at least one property and a spatial distribution of at least one type of microbe bound to at least one of the plurality of specific microbe-binding elements; and a computing device including a processor, the computing device operably coupled to the image-capture device and including circuitry configured to receive the digital output from the image-capture device including the information associated with the at least one property and the spatial distribution of the at least one type of microbe bound to the at least one of the plurality of specific microbe-binding elements associated with the inner surface of the skin-covering material, compare the at least one property of the at least one type of microbe with a database of reference microbe properties, and generate a digital profile including the at least one property and the spatial distribution of the at least one type of microbe bound to the at least one of the plurality of specific microbe-binding elements. In addition to the foregoing, other system aspects are described in the claims, drawings, and text forming a part of the present disclosure.

In an aspect, a method includes, but is not limited to, receiving a digital output from an image-capture device, the digital output including information associated with at least one property and a spatial distribution of at least one type of microbe bound to at least one of a plurality of specific microbe-binding elements associated with an inner surface of a skin-covering material; identifying the at least one type of microbe bound to the at least one of the plurality of specific microbe-binding elements by comparing the information associated with the at least one property of the at least one type of microbe with a database of reference microbe properties; and reporting to a user an identification and a spatial profile of the identified at least one type of microbe bound to the at least one of the plurality of specific microbe-binding elements associated with the inner surface of the skin-covering material. In addition to the foregoing, other method aspects are described in the claims, drawings, and text forming a part of the present disclosure.

In an aspect, a method includes, but is not limited to, receiving a first digital output from an image-capture device, the first digital output including information associated with at least one property and a spatial distribution of a first set of one or more microbes bound at a first time point to one or more of a plurality of specific microbe-binding elements on an inner surface of a first skin-covering material; receiving a second digital output from the image-capture device, the second digital output including information associated with at least one property and a spatial distribution of a second set of microbes bound at a second time point to one or more of a plurality of specific microbe-binding elements on an inner surface of a second skin-covering material; comparing the first digital output with the second digital output; generating a recommended treatment regimen based on the comparison of the first digital output with the second digital output; and reporting the recommended treatment regimen to a user. In addition to the foregoing, other method aspects are described in the claims, drawings, and text forming a part of the present disclosure.

In an aspect, a method includes, but is not limited to, applying a skin-covering material to a skin surface of an individual, the skin-covering material including an inner surface and an outer surface, the inner surface substantially conforming in shape to a topography of the skin surface of the individual and including a plurality of specific microbe-binding elements; removing the skin-covering material from the skin surface of the individual; capturing at least one image of the inner surface of the skin-covering material with an image-capture device and transforming the captured at least one image into a digital output, the digital output including information associated with at least one property and a spatial distribution of at least one type of microbe bound to the at least one of the plurality of specific microbe-binding elements on the inner surface of the skin-covering material; receiving the digital output from the image-capture device, the digital output including information associated with at least one property and a spatial distribution of at least one type of microbe bound to the at least one of the plurality of specific microbe-binding elements on the inner surface of the skin-covering material; identifying the at least one type of microbe bound to the at least one of the plurality of specific microbe-binding elements by comparing the information associated with the at least one property of the at least one type of microbe with a database of reference microbe properties; and reporting to a user an identification and spatial profile of the identified at least one type of microbe bound to the at least one of the plurality of specific microbe-binding elements on the inner surface of the skin-covering material. In addition to the foregoing, other method aspects are described in the claims, drawings, and text forming a part of the present disclosure.

In an aspect, an article of manufacture includes, but is not limited to, non-transitory machine readable media bearing one or more instructions for assessing microbiota of skin, the one or more instructions including one or more instructions for receiving a digital output from an image-capture device, the digital output including information associated with at least one property and a spatial distribution of at least one type of microbe bound to at least one of a plurality of specific microbe-binding elements on an inner surface of a skin-covering material; one or more instructions for identifying the at least one type of microbe bound to the at least one of the plurality of specific microbe-binding elements by comparing the information associated with the at least one property of the at least one type of microbe with a database of reference microbe properties; one or more instructions for generating a digital alignment of the spatial distribution of the identified at least one type of microbe bound to the at least one of the plurality of specific microbe-binding elements on the inner surface of the skin-covering material with a digital image of a skin surface of an individual covered by the inner surface of the skin-covering material; one or more instructions for generating a personalized microbe profile from the digital alignment, the personalized digital profile including the identity of the at least one type of microbe and the spatial distribution of the at least one type of microbe on the skin surface of the individual; one or more instructions for comparing the personalized microbe profile with a reference microbe profile; one or more instructions for generating a recommended treatment regimen for the individual based on the comparison of the personalized microbe profile with the reference microbe profile; and one or more instructions for reporting to a user at least one of the personalized microbe profile or the recommended treatment regimen. In addition to the foregoing, other aspects of the article of manufacture are described in the claims, drawings, and text forming a part of the present disclosure.

In an aspect, a system includes, but is not limited to, an image-capture device including circuitry to capture at least one image of an inner surface of a skin-covering material and to transform the captured at least one image into a digital output including information associated with at least one property and a spatial distribution of at least one type of microbe bound to the inner surface of the skin-covering material; a computing device including a processor, the computing device operably coupled to the image-capture device; and non-transitory machine readable media readable by the computing device and bearing one or more instructions assessing microbiota of a skin surface of an individual, the one or more instructions including one or more instructions for receiving the digital output from the image-capture device, the digital output including the information associated with the at least one property and the spatial distribution of the at least one type of microbe bound to the inner surface of the skin-covering material; one or more instructions for comparing the information associated with the at least one property of the at least one type of microbe bound to the inner surface of the skin-covering material with a database of reference microbe properties; one or more instructions for generating a microbe profile including the at least one property and the spatial distribution of the at least one type of microbe bound to the inner surface of the skin-covering material; one or more instructions for generating a recommended treatment regimen for the individual based on a comparison of the microbe profile with a reference microbe profile; and one or more instructions for reporting to a user at least one of the microbe profile or the recommended treatment regimen. In addition to the foregoing, other aspects of the system are described in the claims, drawings, and text forming a part of the present disclosure.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIGS. 5A-5E illustrate aspects of a peelable skin-covering material.

FIG. 6 is a flowchart of a method for assessing microbiota of skin.

FIG. 7 is a flowchart showing aspects of a method such as depicted in FIG. 6.

FIG. 8 is a flowchart depicting aspects of a method such as shown in FIG. 6.

FIG. 10 is a flowchart of a method for assessing microbiota of skin.

FIG. 11 is a flowchart showing aspects of a method such as depicted in FIG. 10.

FIGS. 12A-12D illustrate aspects of a system for assessing microbiota of skin.

FIG. 13 is a schematic an article of manufacture for assessing microbiota of skin.

FIG. 20 is a flowchart of a method for assessing microbiota of skin.

FIG. 21 is a flowchart illustrating aspects of a method such as shown in FIG. 21.

FIG. 22 is a flowchart showing aspects of a method depicted in FIG. 21.

FIG. 23 is a flowchart of a method for assessing microbiota of skin.

FIG. 24 is a flowchart of a method for assessing microbiota of skin.

FIG. 25 is a flowchart illustrating aspects of a method such as shown in FIG. 25.

FIGS. 26A-26E illustrates aspects of a system for assessing microbiota of skin.

FIG. 27 is a schematic of an article of manufacture for assessing microbiota of skin.

FIGS. 28A-28C illustrates aspects of a system for assessing microbiota of skin.

FIG. 30 illustrates aspects of a system for assessing microbiota of skin.

DETAILED DESCRIPTION

Figure 1:
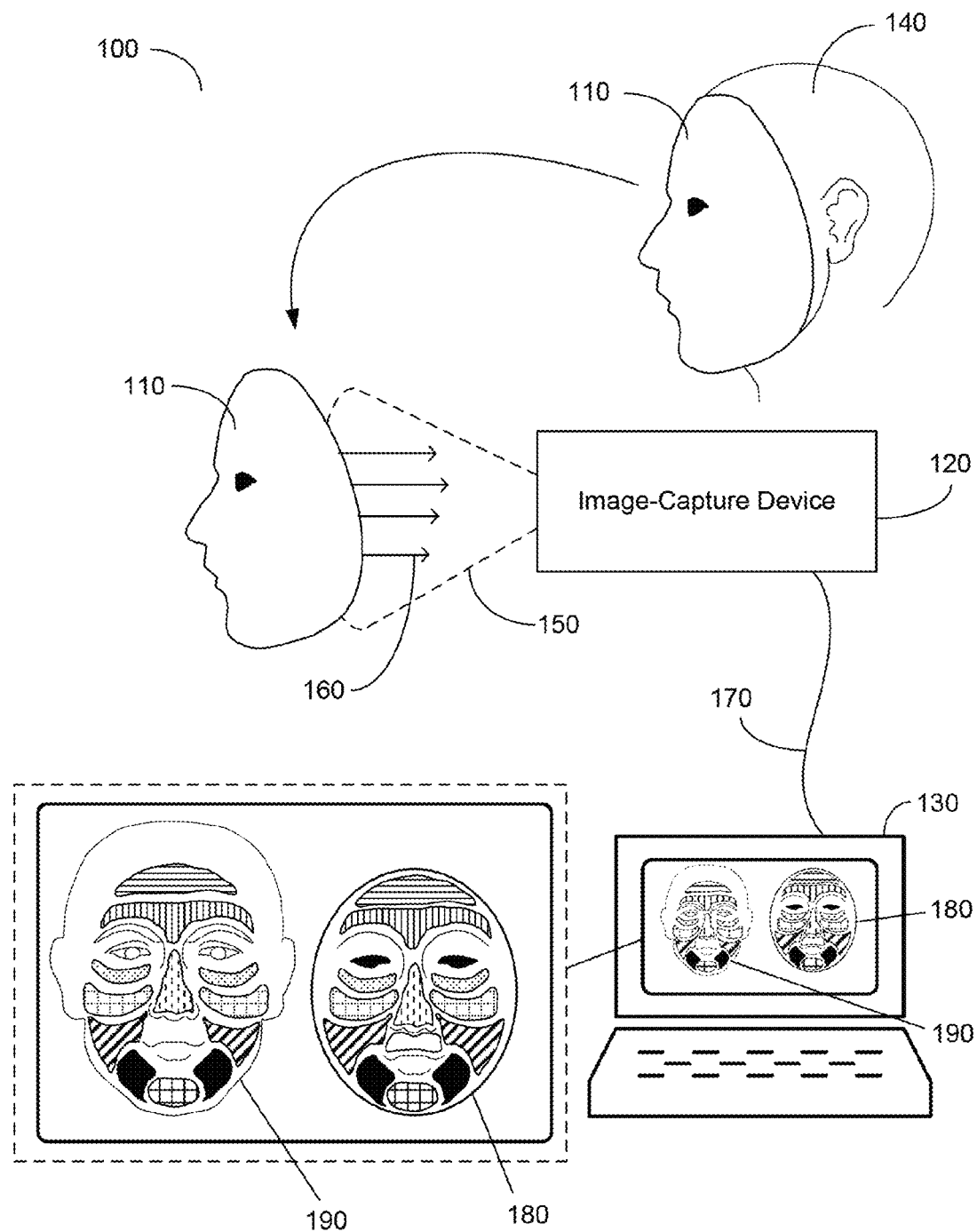
FIG. 1 is a schematic of a system for assessing microbiota of skin.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

The skin, the largest organ of the mammalian body, is inhabited by a diverse array of microbes, including bacteria, fungi, viruses, parasites, archaea, or small arthropods (e.g., mites). Variations in regional properties of the skin, e.g., variations in pH, moisture, pores, texture, and the like, from one body location to another contribute to the spatial diversity of skin-associated microbes. Similarly, the type of microbes and/or spatial distribution of one or more microbes on the skin surface may change in response to cleaning of the skin surface, application of anti-microbial agents, application of irritating agents, e.g., make-up, lotion, sun screen, or exposure to irritating conditions, e.g., diet, disease, wind, or sun exposure. In some instances, skin-resident microbes on the skin surface, e.g., commensal bacteria, provide a benefit to the individual. For example, *Staphylococcus epidermidis* has been demonstrated to modulate the host innate immune response, inhibiting other bacterial pathogens such as *Staphylococcus aureus* and Group A *Streptococcus*. See, e.g., Orrice & Segre (2011) Nat. Rev. Microbiol. 9:244-53, which is incorporated herein by reference. In some instances, skin-resident microbes have been linked to pathological conditions including acne, psoriasis, and atopic dermatitis. See, e.g., Cho & Blaser (2012) *Nat. Rev. Genet.* 13:260-270, which is incorporated herein by reference. In general, understanding the identity and spatial distribution of skin-resident microbes on the skin under normal and/or pathological conditions can contribute to decisions regarding therapeutic, preventative, and/or cosmetic treatments. Described here are embodiments of systems, methods, and devices for assessing the microbiota of skin.

FIG. 1 illustrates aspects of a system for assessing the microbiota of skin. System 100 includes components configured to sample and report to a user the identity and the spatial distribution of microbes on a skin surface of an individual. System 100 includes a skin-covering material 110, an image-capture device 120, and a computing device 130. Skin-covering material 110 includes an inner surface and an outer surface, the inner surface substantially conforming in shape to a topography of a skin surface of individual 140. At least a portion of the inner surface of skin-covering 110 includes a region configured to capture or bind microbes from the skin surface of individual 140. In an aspect, the inner surface of skin-covering 110 includes a microbe-capture region. In general, skin-covering material 110 is configured to be in physical contact with the skin surface of an individual and to capture at least one type of microbe from the skin surface of the individual.

System 100 includes image-capture device 120. Image-capture device 120 includes circuitry to capture at least one image of the inner surface of skin-covering material 110 and to transform the captured at least one image into a digital output including information associated with at least one property and a spatial distribution of at least one type of microbe bound to the microbe-capture region on the inner surface of skin-covering material 110.

System 100 includes computing device 130. Computing device 130 includes a processor and is operably coupled to image-capture device 120 through a communication link 170. Communication link 170 can include at least one of a wireless communication link, e.g., Bluetooth or other radio transmission link, or a wired communication link, e.g., an electrical link. Computing device 130 further includes circuitry configured to receive a digital output from image-capture device 120 including information associated with at least one property and a spatial distribution of the at least one type of microbe bound to the microbe-capture region; compare the at least one property of the at least one type of microbe with a database of reference microbe properties; and generate a digital profile 180 including the at least one property and the spatial distribution of the at least one type of microbe bound to the microbe-capture region of skin-covering material 110. In an aspect, computing device 130 further includes circuitry to generate a digital alignment 190 of digital profile 180 of the at least one type of microbe captured on the microbe-capture region of skin-covering material 110 with a digital image of a skin surface of individual 140 covered by the microbe-capture region of skin-covering material 110. Digital alignment 190 can be reported to a user of the system, e.g., individual 140 or another individual, e.g., a service provider, to aide in determining a recommended treatment regimen to maintain or alter the current types and spatial distribution of microbes on the skin surface of the individual.

Skin-Covering Material

Skin-covering material 110 includes an inner surface that substantially conforms in shape to a topography of a skin surface of an individual. The topography of the skin surface can include both the micro-topography, e.g., the texture and/or pattern of the skin surface, and the macro-topography, e.g., anatomical features such as nose, lips, cheeks, large wrinkles, joints, and the like. The skin surface can include any of a number of regions of the body including, but not limited to the facial region, torso region, abdominal region, head region, neck region, upper extremity, lower extremity, buttocks, or any other body region for which analysis of the spatial distribution of microbiota of the individual is desired. In an aspect, the skin-covering material substantially conforms in shape to a topography of a mucous membrane associated with a body cavity. In an aspect, the skin-covering material substantially conforms in shape to a topography of nasal mucosa, vaginal mucosa, oral mucosa, urethral mucosa, rectal mucosa, or ear mucosa. In an aspect, the skin-covering material may be configured to substantially conform in shape to the topography of the skin surface of all or part of the individual's face to form, for example, a mask-like covering. In an aspect, the skin-covering material is personalized to substantially conform to the topography of the skin surface of a specific individual. In an aspect, the skin-covering material is non-planar, e.g., substantially conforming in shape to a topography of a skin surface that includes non-planar contours, e.g., the features of a face.

In an aspect, skin-covering material 110 includes a pre-formed skin-covering. In an aspect, the pre-formed skin-covering material includes a semi-rigid pre-formed skin-covering material. For example, the skin-covering material can include a thin flexible substrate that conforms to the topography of the skin surface of the individual. For example, the skin-covering material can include a flexible strip, a wrap, a band, or the like that conforms to the curvature of a skin surface, e.g., the curvature of the face or arm pit or around an extremity, making uniform contact with the skin so as to uniformly capture representative microbes from all portions of the covered skin. For example, the semi-rigid pre-formed skin-covering material may include a specially coated strip of bendable material, e.g., a coated sheet of Mylar or a treated piece of fabric, that when applied to a skin surface substantially conforms in shape to the topography of the skin surface, e.g., wraps around the contours of a body part. In an aspect, the skin-covering material includes a flexible strip similar to a wound covering but with a region configured to capture one or more skin-resident microbes.

In an aspect, the pre-formed skin-covering material includes a rigid pre-formed skin-covering material. For example, the rigid pre-formed skin-covering material can include a rigid thin plastic substrate that has been designed and manufactured, e.g., by three-dimensional printing, to substantially conform in shape to the topography of an individual's skin surface. For example, the rigid pre-formed skin-covering material can include a mask-like structure that substantially conforms in shape to the topography of the skin surface of an individual's face. In general, the pre-formed skin-covering material is configured to substantially conform to the topography of the skin surface of the individual to achieve uniform contact of the microbe-capture region on the inner surface of the skin-covering material with the underlying skin surface.

In an aspect, the pre-formed skin-covering material includes a thin substrate that is non-planar and is either flexible or rigid. For example, the pre-formed skin-covering material may include a structure that mirrors the contours and/or topography of a specific region of the skin. For example, the pre-formed skin-covering material may have a non-planar structure that mirrors the contours and/or topography of an individual's face and as such when placed on the surface of the skin makes uniform contact with substantially all of the overlapping portions. For example, the pre-formed skin-covering material can include a non-planar, flexible latex-like thin substrate that substantially conforms to the topography of the skin surface of the individual. For example, the pre-formed skin-covering material can include a non-planar, hard plastic-like, thin substrate that substantially conforms to the topography of the skin surface of the individual. In an aspect, the rigid or semi-rigid pre-formed skin-covering material is formed using three-dimensional printing to substantially conform to a digital rendering of a skin surface topography of an individual. In an aspect, the rigid or semi-rigid pre-formed skin-covering material is generic, substantially conforming to the topography of the skin surface of any of a number of individuals.

In an aspect, the pre-formed skin-covering material may cause the topography of the skin to conform to the topography of the skin-covering material, e.g., when a pre-formed skin-covering material is pressed upon a conformable body part, e.g., a body part including ample soft tissue. For example, a pre-formed rigid skin-covering material, e.g., a mask, may be pressed against an individual's cheek, buttocks, or upper thigh to achieve uniform contact of the pre-formed skin-covering material with the underlying skin surface.

The pre-formed skin-covering material can include any of a number of materials capable of being shaped, molded or printed to form the pre-formed skin-covering material. Non-limiting examples of shapeable, moldable or printable materials include acrylic, nylon, plastic, ceramic, resin, rubber, epoxy, thermoplastic, polymer, photopolymer, polyurethane, gel, hydrogel, latex, or silicone. Additional non-limiting examples of shapeable, moldable or printable materials for use in forming the skin covering include: metals such as titanium/titanium alloys, TiNi (shape memory/super elastic), aluminum oxide, platinum/platinum alloys, stainless steels, pyrolytic carbon, silver or glassy carbon; polymers such as polyurethanes, polycarbonates, silicone elastomers, polyolefins including polyethylenes or polypropylenes, polyvinyl chlorides, polyethers, polyesters, nylons, polyvinyl pyrrolidones, polyacrylates and polymethacrylates such as polymethylmethacrylate (PMMA), n-Butyl cyanoacrylate, polyvinyl alcohols, polyisoprenes, rubber, cellulosics, polyvinylidene fluoride (PVDF), polytetrafluoroethylene, ethylene tetrafluoroethylene copolymer (ETFE), acrylonitrile butadiene ethylene, polyamide, polyimide, styrene acrylonitrile, and the like; minerals or ceramics such as hydroxapatite; organic materials such as wood, cellulose, or compressed carbon; and other materials such as glass, or the like.

The pre-formed skin-covering material may be formed from shapeable, moldable, or printable materials by a variety of manufacturing methods. In some embodiments, the pre-formed skin-covering material is generated from a mold made of a skin surface of the individual. For example, a mold of a skin surface of an individual can be generated by covering the skin surface, e.g., an individual's face, with a material that hardens to conform in shape to a topography of the skin surface. For example, alginate may be used in combination with plaster bandages to create a mold of a skin surface of an individual, e.g., the individual's face. In some embodiments, the mold itself can be used as the pre-formed skin-covering material. Non-limiting examples of materials that can be used for generating a mold of a skin surface of an individual include modeling clay, plaster, alginate, or combinations thereof. In some embodiments, the mold can be a reusable template for forming one or more pre-formed skin-covering material with a material, e.g., latex, that is poured or spread into the mold, hardened, and removed from the mold.

In an aspect, the pre-formed skin-covering material is personalized to substantially conform to the topography of the skin surface of the individual. For example, a digital three-dimensional representation of the skin surface of the individual may be used to digitally render a pre-formed skin-covering, the latter of which is used as a template for manufacturing the pre-formed skin-covering using a three-dimensional printer. One or more digital images of the skin surface of the individual for use in generating a digital three-dimensional representation of the skin surface can be acquired from one or more of a digital camera or scanning device. For example, two video cameras, slightly apart, can be used to image the same portion of skin surface of the individual in a process termed stereophotogrammetry. For example, a single camera can be used to take multiple images under different lighting conditions or from different positions. In an aspect, the topography of the skin surface of an individual can be acquired in a point-cloud format using a three-dimensional sensing system consisting of two or more digital cameras and one or more projectors connected to a personal computer. The camera position and shutter can be adjusted to the body region, which is exposed to structured light, allowing for optical representation of the surface by a cloud of up to 300,000 points in three-dimensional coordinates (see, e.g., Feng et al., *Br. J. Oral Maxillofac. Surg.* (2010) 48:105-109, which is incorporated herein by reference). In some embodiments, the combination of stereophotogrammetry and 3D laser scanner techniques can be combined to generate a three-dimensional model of the skin surface of an individual (see, e.g., Majid, et al. *International Archives of the Photogrammetry, Remote Sensing and Spatial Information Science.* Vol.) (XXVII. Part B5. (2008) 805-811; Markiewicz & Bell, *Facial Plast. Surg. Clin. N. Am.* (2011) 19:655-682; van Heerbeek et al., *Rhinology* (2009) 47:121-125, which are incorporated herein by reference). Scanners for scanning head, face and/or whole body are commercially available (from, e.g., Cyberware, Monterey Calif.; Accurex Measurement Inc., Swathmore, Pa.; 3dMD Atlanta, Ga.; Konica/Minolta, Ramsey, N.J.)

In an aspect, surface scanning software can be used to import individual points of the skin surface, e.g., of the face, and then combine them in the X, Y, and Z axes to render a three-dimensional representation of the topography of the skin surface. In some embodiments, the one or more images of the skin surface may include point clouds of data that are reconstructed using one or more three-dimensional modeling algorithms to form a digitally rendered model of the skin-covering material. One or more modeling programs can be used for this purpose. Non-limiting examples of types of modeling programs include polygonal mesh three-dimensional modeling programs, non-uniform rational basis spline (NURBS) surface modeling programs, or editable feature-based computer aided design (CAD) modeling programs. In some embodiments, the data may be modeled using a first modeling approach, for example, a NURBS based modeling program and further refined using a second modeling approach, for example, a CAD-based modeling program. Numerous software programs are available for generating three-dimensional models from scanned images. For example, non-limiting examples of CAD/CAM software programs applicable to medical imaging include Amira (Visage Imaging GmbH, Berlin Germany); Analyze (Ana-lyzeDirect, Inc, Overland Park, Kans.); iNtellect Cranial Navigation System (Stryker, Freiburg, Germany); iPlan (BrainLab, Westchester, Ill.); Maxilim (Medicim, Bruges Belgium), Mimics, SurgiCase CMF, and SimPlant OMS (Materialise, Leuven, Belgium); Voxim (IVS Solutions, Chemnitz, Germany), 3dMD (Atlanta, Ga.); Alma3D (Alma IT Systems, Barcelona, Spain); and ImageJ (National Institutes of Health, Boston, Mass.) (see, e.g., Markiewicz & Bell, *Facial Plast. Surg. Clin. N. Am.* (2011) 19:655-682, which is incorporated herein by reference). Facial feature extraction can be acquired using one or more of an active shape model algorithm (see, e.g., Sun & Xie, 11$^{th}$ *IEEE International Conference on Communication Technology Proceedings,* (2008) pp. 661-664; Zheng & Yang *IEEE Proceedings of the Seventh International conference on Machine Learning and Cybernetics,* (2008) pp. 2841-2845, which are incorporated herein by reference). Other software packages capable of generating a digitally rendered model of the skin-covering material from one or more digital images of a skin surface of an individual can be used for this purpose. Additional approaches for generating three-dimensional models are described in Bernardini & Rushmeier *Computer Graphics Forum* (2002) 21:149-172, which is incorporated herein by reference.

In an aspect, information regarding the digitally rendered model of the pre-formed skin-covering material is sent to a manufacturing device which produces the pre-formed skin-covering material based on the received information. Non-limiting examples of methods for generating a three-dimensional structure from digitized information include stereolithography, laser sintering, fused deposition modeling, polyjet, three-dimensional printing, vacuum casting, reaction injection molding, or injection molding. Non-limiting examples of materials for generating a three-dimensional structure from digitized information include one or more of acrylic, nylon, plastic, ceramic, resin, rubber, epoxy, thermoplastic, photopolymer, polyurethane, latex or silicone. The type of material used for forming the pre-formed skin-covering material is dependent upon the method used to form the pre-formed skin-covering material and the desired properties, e.g., rigidity, transparency, and/or porosity, of the final product. Exemplary materials and methods for forming a pre-formed skin-covering material using stereolithography, laser scintering or three-dimensional printing as well as other methods for forming a pre-formed skin-covering material from the digitally rendered model of the pre-formed skin-covering material are described herein.

In an aspect, the pre-formed skin-covering material is formed using an additive manufacturing process. Additive manufacturing refers to a class of manufacturing process in which a three-dimensional object is built by adding layers of material upon one another. Other terms include layered manufacturing, direct digital manufacturing, or solid freeform fabrication. Non-limiting examples of additive manufacturing processes include liquid-based processes, e.g., stereolithography, jetted photopolymer, and ink jet printing; powder-based processes, e.g., selective laser sintering, direct metal laser sintering, and three-dimensional printing; and solid-based processes, e.g., laminated object manufacturing, fused deposition modeling.

In an aspect, the pre-formed skin-covering material is formed using a subtractive manufacturing process. Subtractive manufacturing refers to a class of manufacturing process in which a three-dimensional object is built by cutting away material. Non-limiting examples of subtractive manufacturing processes include machining, milling, turning, and drilling. Other non-limiting examples of manufacturing processes include molding, e.g., blow molding, injection molding, or thermoforming; and casting, e.g., centrifugal casting, die casting, sand casting, shell mold casting.

In an aspect, the pre-formed skin-covering material is generated using stereolithography using one or more optically curable photopolymers. Non-limiting examples of materials useful for stereolithography include poly(ethylene glycol) 1500, Accura 60, Accura 25, Accura Xtreme, Somos 9420, Somos 11122, Somos 18420, Somos DMX, Rigi2200, TuskXC2700T/Tusk2700W, Nano5000, Flex45, Flex65, Flex70B, Flex 80, Protogen White. Other non-limiting examples of stereolithography include three-dimensional printing (3D printing), optical fabrication, photo-solidification, solid free-form fabrication, and solid imaging.

In some embodiments, the pre-formed skin-covering material can be generated by 3D printing using an inkjet technology, e.g., PolyJet™ (from Objet Ltd) in which photopolymer materials are jetted in ultra-thin layers onto a build tray and cured layer by layer with UV light. Non-limiting examples of materials for use in generating a pre-formed skin-covering material using inkjet technology include Fullcure 720, VeroWhite, VeroBlack, VeroBlue, and VeroGray for rigid structures; Durus for semi-flexible structures; and Tango Elastomers for rubber-like structures. Other examples of 3D printers include ProJet and ZPrinters available from 3D Systems Corporation, Rock Hill S.C. and Freeform Pico, Asiga, Anaheim Hills, Calif.

In some embodiments, the pre-formed skin-covering material is generated using selective laser sintering in which a high power laser, e.g., a carbon dioxide laser, is used to fuse small particles of plastic, metal, ceramic, glass powders, or combinations thereof into a mass that has a desired three-dimensional shape. Non-limiting examples of material for use in generating a pre-formed skin-covering material guide using laser sintering include polyamide, nylon, carbon, hydroxyapatite, glass filled polyamide, and alumide.

In some embodiments, the pre-formed skin-covering material is generated using fused deposition modeling. Fused deposition modeling is an extrusion-based three-dimensional modeling process using thermoplastic materials. Non-limiting examples of materials for use in fused deposition modeling include the thermoplastics ABS, ABS/F1, polycarbonate, and Ultem 9085. The uPrint SE from Stratasys (Eden Prairie, Minn.) or the Dimension Elite 3D printer from Dimension, Inc. (Eden Prairie, Minn.) are non-limiting examples of systems for fused deposition modeling with thermoplastics that might be appropriate for use in a medical clinic.

In an aspect, the pre-formed skin-covering material can be formed from a three-dimensional mold surface formed from the digitally rendered model of the pre-formed skin-covering material and using the three-dimensional mold surface with a moldable material to generate the pre-formed skin-covering material. For example, a three-dimensional mold surface of the individual's face can be fabricated from a thermoplastic material based on the digitally rendered model of the wearable injection guide. A moldable material, e.g., latex, can then be poured into or over the three-dimensional mold surface to generate the formed pre-formed skin-covering material. The three-dimensional mold surface can be used repeatedly to generate one or more pre-formed skin-covering material.

In an aspect, skin-covering material 110 includes a peelable skin-covering material. The peelable skin-covering material can include any of a number of materials applied to the skin surface of the individual and subsequently peeled as a single piece from the surface of the skin. For example, the peelable skin-covering material can include one or more shapeable or moldable materials applied to the skin surface of an individual and peeled therefrom. In some embodiments, the shapeable or moldable material may harden over an elapsed period of time or by exposure to ambient air. In some embodiments, the shapeable or moldable material may be hardened in response to electromagnetic energy, e.g., light of a specific wavelength, or in response to elevated temperature.

In an aspect, the peelable skin-covering material includes a settable material. The settable material includes at least one material configured to undergo a phase change from a liquid or gelled phase to a flexible or rigid solid phase in response to an applied stimulus. For example, the settable material can include a material that is poured onto the skin surface of an individual. For example, the settable material can include a material that is spread onto the skin surface of an individual. Non-limiting examples of settable material include latex, gel, polymer, plastic, or resin. For example, the settable material can include one or more polymers, e.g., polyvinyl alcohol, polyacrylate, polymethacrylate and/or polyacrylamide. See, e.g., U.S. Pat. No. 5,747,022; U.S. Patent Application 2005/0019291, which are incorporated herein by reference. The applied stimulus can include one or more of exposure to air, a thermal stimulus, e.g., heat, or an electromagnetic stimulus, e.g., exposure to a specific wavelength or spectrum of light.

In an aspect, the peelable skin-covering material includes a shrink-wrap material that is applied to the skin surface as a thin sheet and conformed in shape to the topography of the skin surface using an applied stimulus, e.g., heat.

In an aspect, the skin-covering material, whether pre-formed or peelable from a settable material, further includes a medicament for treating a skin condition. The medicament can be included as a layer on the inner surface of a pre-formed skin-covering material or as part of the settable material used to form a peelable skin-covering material. In an aspect, the medicament can be eluted by simple diffusion from a gel, e.g., a hydrogel, associated with the skin-covering material. Non-limiting examples of medicaments for treating a skin condition include antibacterial agents, anti-fungal agents, antiviral agents, moisturizers, chemotherapies, e.g., 5-fluorourasil, probiotics, prebiotics, benzoyl peroxide, retinoid derivatives, and salicylic acid.

In an aspect skin-covering material 110 includes at least one registration mark to register the skin-covering material to at least one landmark on the skin surface of the individual. One or more registration marks on the skin-covering material can be used to align with one or more landmarks on the skin surface. The one or more landmarks can include one or more of pigmentation, pigmented areas, tattoos, skin texture patterns, blemishes, scars, anatomical features, or subsurface blood vessels associated with the skin surface. In an aspect, the one or more registration marks are incorporated into the manufacture of the skin-covering material based on a digital image of the skin surface including the one or more landmarks over which the skin-covering material will be placed. In an aspect, the one or more registration marks can be added with a pen or other marking device while the skin-covering material is on the skin surface of the individual.

In an aspect, the skin-covering material includes one or more tearable lines of perforations. In an aspect, the skin-covering material can be manufactured with perforations. For example, the skin-covering material may be manufactured using a three-dimensional printing process as described herein in which the digital template for the skin-covering material includes perforations. In an aspect, the perforations are added to the skin-covering material after manufacture. For example, a skin-covering material manufactured from a thin sheet of material, e.g., latex or paper may be modified with a device configured to punch holes through the skin-covering material. In general, the tearable lines of perforations allow the skin-covering material to be separated into pieces that can be accommodated by the imaging window or scanning surface of the image-capture device.

Microbe-Capture Region

Returning to FIG. 1, skin-covering material 110 includes an inner surface including a microbe-capture region configured to capture at least one type of microbe from the skin surface of an individual when the skin-covering material is placed in physical contact with the skin surface of the individual. The at least one type of microbe includes at least one type of bacteria, fungus, virus, parasite, archaea, or small arthropod (e.g., mites). In an aspect, the at least one type of microbe includes at least one type of mutualistic microbe, commensal microbe, or pathogenic microbe. In an aspect, the at least one type of microbe captured by the skin-covering material can include at least one type of skin-resident microbe. Non-limiting examples of skin-associated or skin-resident bacteria include proteobacteria, e.g., *Pseudomonas* sp., *Janthinobacterium* sp, *Alphaproteobacteria*, other gammaproteobacteria, and betaproteobacteria; *Actinobacteria*, e.g., *Kocuria* sp., *Propionibacteria* sp.; *Firmicutes*, e.g., *Staphylococcus epidermidis*; *Bacteroidetes*; and *Spirochaetes*. See, e.g., Grice et al. (2008) *Genome Res.* 18:1043-1050; Grice & Segre (2011) *Nat. Rev. Microbiol.* 9:244-253, which are incorporated herein by reference. Non-limiting examples of fungi, including skin-resident or associated types of fungi, include dermatophtyes, e.g., trichophyton, microsporum, epidermophyton, tinea capitis. Other skin associated fungi include but are not limited to yeast, *Candida*, e.g., *Candida albicans*; and *Malassezia* spp (e.g., *M. dermatis, M. furfur, M. globosa,* and *M. restricta*). See, e.g., Gaitanis et al. (2012) *Clin. Microbiol. Rev.* 25:106-141, which is incorporated herein by reference. Non-limiting examples of skin-associated or skin-resident viruses include herpes simplex virus type I (HSV-1), herpes zoster, Molluscum contagiosum, human papillomavirus (HPV), Coxsackie virus A16, and herpes gladiatorum. Non-limiting examples of other parasites resident or associated with a skin surface include skin-associated parasitic arthropods including parasitic mites, e.g., *Demodex* spp including *D. folliculorum* and *D. brevis*, and *Sarcoptes scabiei*, a skin parasite associated with scabies.

In an aspect, the microbe-capture region includes one or more materials configured to non-selectively capture microbes from the skin surface of the individual. In an aspect, the microbe-capture region includes one or more materials configured to non-selectively capture a representative sample of the microbes, i.e., all microbes, on the skin surface of the individual. In an aspect, the microbe-capture region includes one or more material configured to non-selectively capture a subtype of microbe, e.g., all of a type of microbe, for example, bacteria versus fungi. In general, the microbe-capture region can include one or more materials that interact with biomolecules on the outer surface of microbes, e.g., proteins, polysaccharides, carbohydrates, phospholipids, proteoglycans, and the like. In an aspect, the one or more materials take advantage of hydrogen bonding, electrostatic and/or hydrophobic interactions to capture microbes from the skin surface onto the microbe-capture region. Non-limiting examples of materials for use in a microbe-capture region include poly-ionic surfaces, e.g., poly-cationic surfaces such as polyamino acids (e.g., polylysine) and fibronectin for binding microbes that have an overall negative surface charge. Other non-limiting examples of materials for use in a microbe-capture region include nitrocellulose, cellulose nitrate, hydrophobic polymers, PVDF coated surface, nylon coated surface, streptavidin coated substrate to bind biotin labeled DNA, protein, peptide, Concanavalin A, NHS-ester coated surface covalently coupled with biomolecules containing primary amines, epoxy coated substrate (binds protein and peptides), aldehyde coated substrate for immobilizing amino modified oligos and cDNAs, native proteins, tissues, and cells, and amine substrate for immobilizing long oligos and cDNAs.

The microbe-capture region includes at least a portion of the inner surface of the skin-covering material. In an aspect, the microbe capture region covers the entire inner surface of the skin-covering material. In an aspect, the microbe-capture region is an integral part of the skin-covering material, e.g., the entirety of the skin-covering material has microbe-capturing properties. For example, one or more materials used to form the skin-covering material may include properties, e.g., "tackiness" or charge properties, which allow for non-selective capture of one or more types of microbes from a skin surface. In an aspect, the microbe-capture region forms a separate layer on the inner surface of the skin-covering material. For example, the microbe-capture region may include a material, e.g., a liquid, a gel, or a spray which is spread on the inner surface of a pre-formed skin-covering material to generate the microbe-capture region.

In an aspect, the microbe-capture region forms a separate layer on the inner surface of the skin-covering material. For example, the microbe-capture region may include one or more materials applied to the inner surface of the skin-covering material, e.g., to the inner surface of a pre-formed skin-covering material. For example, the microbe-capture region may include one or more materials that are sprayed onto the inner surface of the skin-covering material. For example, the microbe-capture region may include an adhesive material that is poured or spread on the inner surface of the pre-formed skin-covering material. For example, the microbe-capture region may include a sheet of material, e.g., double-sided adhesive tape, which is applied to the inner surface of the pre-formed skin-covering material. In general, application of the microbe-capture region to the inner surface of the skin-covering material maintains the integrity of the inner surface to substantially conform in shape to the topography of the skin surface to which the skin-covering material is to be placed. For example, the addition of a layer of material constituting the microbe-capture region to the inner surface of a skin-covering material designed for use on an individual's face does not diminish the one-to-one contact of the skin-covering material with the skin surface, allowing for uniform contact and capture of microbes from the skin surface.

In an aspect, the microbe-capture region is replaceable. For example, the microbe-capture region may include a material, e.g., an adhesive, which can be removed, e.g., washed off, from the inner surface of a pre-formed skin-covering material after a first use and replaced with a fresh coating of adhesive for one or more subsequent uses. For example, the microbe-capture region may include one or more strips of material that can be removed from the inner surface of the skin-covering material and replaced with a new strip or sheet of material. For example, the microbe-capture region may include multiple sheets of material, and after each use, the used sheet is removed revealing a fresh, underlying sheet.

In an aspect, the replaceable microbe-capture region is used with a reusable skin-covering material. For example, the skin-covering material may include a pre-formed skin-covering material made from a washable plastic material, the inner surface of which is repeatedly coated with one or more material to form the microbe-capture region. For example, the pre-formed skin-covering material with the adhesive microbe-capture region is used to capture at least one type of microbe at a first time point, washed, the adhesive microbe-capture region reapplied to the inner surface of the pre-formed skin-covering material and used to capture at least one type of microbe at one or more second time point. In an aspect, the reusable skin-covering material is only used for a specific individual, e.g., the individual for whom the skin-covering material has been personally designed for. For example, a pre-formed skin-covering material designed for a specific individual's face using one or more of the manufacturing methods described above may have a replaceable microbe-capture region that is renewed every time the individual visits a service provider, e.g., a dermatologist or cosmetologist, for analysis of microbes on the individual's face. In this manner, changes in the identity and/or spatial distribution of the microbes on the individual's face can be monitored over time without having to generate a new skin-covering material for each visit. Similarly, a reusable, optionally personalized, pre-formed skin-covering material with an easily replaceable microbe-capture region can be used repeatedly by a consumer in the home to periodically monitor microbes on a skin surface. In an aspect, the reusable skin-covering material is applicable to use with any individual, and once sterilized and recoated with a microbe-capture region, usable by any individual.

In an aspect, the microbe-capture region includes at least one consumable. For example, the at least one consumable can include a consumable liquid, spread, or spray containing one or more materials for applying a microbe-capture region to the inner surface of a pre-formed skin-covering.

In an aspect, the microbe-capture region includes a charged surface, e.g., a positively charged surface. In an aspect, the positive charge is provided by the one or more materials used to form the skin-covering material. In an aspect, the positive charge is provided by a positively charged material used to coat the inner surface of the skin-covering material to form the microbe-capture region. For example, polymers of secondary and tertiary amino groups can be used to create a positively charged surface capable of binding bacteria. See, e.g., Terada et al. (2006) *Microbiology* 152:3575-3583, which is incorporated herein by reference. For example, poly-L-lysine, a highly positively charged amino acid chain, can be used to bind microbes to a surface. See, e.g., Cowan et al. (2001) *Biotechnology Letters* 23:1235-1241, which is incorporated herein by reference. For example, the positively charged surface can include cationic polymer, e.g., Kymene® or a responsive polymer. See, e.g., U.S. Patent Application 2007/0134337; WO2010094976, which are incorporated herein by reference.

In an aspect, the microbe-capture region includes at least one of an adhesive, an absorbent, or an adsorbent. For example, the microbe-capture region can include an adhesive or sticky substance that when brought in contact with the skin surface and then removed, non-selectively captures material from the skin including microbes. In an aspect, the adhesive can include one or more pressure-sensitive adhesive, e.g., adhesive tape, applicable for contact with a skin surface. Non-limiting examples of adhesives designed for healthcare use include any of a number of silicone-based pressure sensitive adhesives from, for example, Dow Corning, Midland, Mich. or 3M, St. Paul, Minn. In an aspect, the adhesive forms a separate layer on the inner surface of the semi-rigid skin-covering material. For example, an adhesive may be applied to the inner surface of a preformed plastic or semi-rigid sheet of Mylar that has been shaped or can take a shape that substantially conforms to the topography of a skin surface of an individual.

In an aspect, the microbe-capture region includes a biomolecule-binding polymer. In an aspect, the biomolecule-binding polymer includes a form of cellulose, e.g., nitrocellulose. Binding of biomolecules, e.g., proteins, to nitrocellulose is by a combination of weak intermolecular forces, probably dominated by hydrophobic and van der Waals interactions. In an aspect, biomolecule-binding polymer includes agarose, starch, cellulose acetate, or polyacrylamide. In an aspect, the biomolecule-binding polymer includes one or more polyamino acids. Non-limiting examples of polyamino acids include poly-L-lysine, poly-D-lysine, poly-L-ornithine. For example, poly-L-lysine contains positively charged hydrophilic amino groups that electrostatically bind to the cell surface of bacteria and other cell types.

In an aspect, the microbe-capture region includes one or more biological materials associated with an extracellular matrix, non-limiting examples of which include collagen, laminin, fibronectin, mucopolysaccharides, heparin sulfate, hyaluronidate, and chondroitin sulfate. In an aspect, the microbe-capture region includes albumin. See, e.g., de Chateau et al. (1996) *J. Biol. Chem.* 271:26609-26615, which is incorporated herein by reference.

In an aspect, the microbe-capture region includes one or more microbe-binding lipids bound to the inner surface of the skin-covering material. For example, one or more glycosphingolipids can be attached to a surface of a piece of PVDF membrane and then placed in contact with the skin surface. For example, one or more phospholipids, e.g., phosphatidylcholine, phosphatidylethanolamine, phosphatidylinositol, phosphatidylserine, sphingomyelin can be attached to a surface of a piece of PVDF membrane and then placed in contact with a skin surface.

In an aspect, the microbe-capture region includes a gel. Non-limiting examples of gels include at least one of a hydrogel, a colloid, agar, or gelatin. In an aspect, the entirety of the skin-covering material is comprised of a gel. In an aspect, the entirety of the skin-covering material includes a semi-rigid pre-formed gel. In an aspect, the entirety of the skin-covering material includes a peelable gel. In an aspect, the gel is applied to an inner surface of the skin-covering material, e.g., to the inner surface of a pre-formed skin-covering material. In an aspect, the microbe-capture region includes agar as a separate layer on the inner surface of a pre-formed skin-covering material. For example, a pre-formed skin-covering material may be formed from a plastic material to substantially conform to the topography of a region of a skin surface of an individual and a thin layer of agar applied to at least a portion of the inner surface of the plastic skin-covering to form the microbe-capture region. Contacting the skin with the inner surface of the plastic skin-covering allows skin-resident microbes to be captured on the agar. For example, skin-covering material may include a Mylar sheet that is coated on one surface with a thin layer of gel, the surface including the gel placed in contact with a skin surface to capture at least one type of microbe from the skin surface. In an aspect, the entirety of the skin-covering material is comprised entirely of agar.

In some embodiments, the microbe-capture region may be wetted with a biologically relevant liquid, e.g., water, saline, or buffered saline, prior to placing the skin-covering material on the skin surface of the individual.

In some embodiments, the moisture associated with a settable material, e.g., in a liquid or a gelled phase, can provide an aqueous environment for capturing one or more microbes from the skin surface of the individual.

In an aspect, system 100 further includes at least one enhancing component to enhance binding of the at least one type of microbe on the microbe-capture region of the inner surface of the skin-covering material. In an aspect, the enhancing component includes a thermal component, a vacuum component, a humidity component, a chemical component, or a pressure component. For example, a thermal component, e.g., heat at a temperature compatible with skin, may be used to open skin pores to allowing access for sampling by the skin-covering material. For example, a vacuum component associated with the skin-covering material may be used to suck the at least one type of microbe from the skin surface and onto the microbe-capture region. For example, a humidity component, e.g., pre-wetting the face or the skin-covering material, may be used to create an aqueous environment for binding. For example, a pressure component, e.g., applying equal pressure to the skin-covering material while it is on the skin surface of the individual may ensure equal capture and representation of microbes from the skin surface.

In an aspect, the at least one enhancing component includes a chemical enhancing component, non-limiting examples of which include at least one of a skin-softener, a detergent, or a lysing compound. For example, the chemical enhancing component can be applied to the skin surface prior to applying the skin-covering material. For example, the chemical enhancing component may be included in the inner surface of the skin-covering material and makes contact with the skin upon applying the skin-covering material to the skin surface. In general, the chemical enhancing component either enhances capture of microbes from the skin surface, e.g., enhancing accessibility, or enhances detection of one or more biomolecules associated with the microbes. In an aspect, the enhancing component includes at least one skin-softener, non-limiting examples of which include emollients, moisturizers, lubricants, and/or oils.

In an aspect, the enhancing component includes a lysing compound to lyse the one or more microbes either directly on the skin surface or on the microbe-capture region. The lysing compound allows biomolecules, e.g., proteins or nucleic acids, in the interior of the microbe to be more accessible for detection. Non-limiting examples of lysing compounds includes urea, enzymes for lysing bacterial cell walls (e.g., lysozyme, labiase, lysostaphin, mutanolysis, achromopeptidase), and enzymes for lysing fungal, e.g., yeast, cell walls (e.g., kitalase, lyticase, chitinase, glucanase). One or more detergents or surfactants may also be used for lysing cells, non-limiting examples of which include nonionic detergents, e.g., Triton X-100, Nonidet P-40, Tween 20; zwitterionic detergents, e.g., CHAPS; and ionic detergents, e.g., sodium dodecyl sulfate.

Image-Capture Device

Returning to FIG. 1, system 100 for assessing the microbiota of the skin surface of an individual further includes an image-capture device 120 including circuitry configured to capture at least one image of the inner surface of the skin-covering material. In an aspect, image-capture device 120 includes an energy-emitting mechanism and circuitry to scan the inner surface of skin-covering material 110 with directed energy to detect one or more signals emitted from the inner surface of skin-covering 110 and to transform the one or more detected signals into a digital output for receipt by computing device 130.

In an aspect, the image-capture device includes at least one camera, e.g., a digital camera, configured to capture one or more images. In an aspect, the at least one camera may capture one or more images in the visible spectrum. In an aspect, the at least one camera may capture one or more images in other portions of the electromagnetic spectrum, e.g., infrared or ultraviolet. In an aspect, the at least one camera may capture emitted and/or reflected light. The image-capture device can include one or more electronic image sensors, e.g., photodiodes, photoresistors, charge-coupled devices (CCD), and/or complementary metal oxide semiconductor (CMOS) devices. In an aspect, the image-capture device includes a single-shot capture device with one CCD with a Bayer filter mosaic or three separate image sensors, which are exposed to the same image via a beam splitter. In an aspect, the image-capture device includes a multi-shot capture device. For example, a single CCD sensor may obtain additive color information by capturing an image three times, each with a different filter (e.g., red, green, and blue). For example, the CCD sensor may capture images as it is moved to various locations on the focal plane and a high resolution composite image "stitched" together. In an aspect, the image-capture device includes a scanning device in which the sensor moves across the focal plane. For example, the camera can include a rotating line camera with a linear CCD array to assemble a high resolution digital image as the camera rotates. Camera can include an area array of CCD or CMOS sensors. Camera can include a linear array of CCD (monochrome) or 3-strip CCD with color filters.

In an aspect, the image-capture device includes at least one scanning device. Non-limiting examples of scanners include optical scanners, fluorescence scanners, acoustic scanners, electrical scanners, electromagnetic scanners, or magnetic scanners. In an aspect, the scanner includes an energy-emitting mechanism, e.g., a light source or a laser, and circuitry to scan the inner surface of a skin-covering material with directed energy, e.g., light of a specified wavelength, to detect one or more signals emitted or reflected from the inner surface of skin-covering material and to transform the one or more detected signals into a digital output. The one or more signals emitted or reflected from the inner surface of the skin-covering material indicative of the identity and/or spatial distribution of microbes captured from the skin surface of the individual.

In an aspect, the image-capture device includes a colorimetric scanner configured to detect color from the at least one type of microbe or a colored reagent in proximity to the at least one type of microbe. For example, the color may be an inherent property of the microbe. For example, the color may arise from addition of one or more developing reagents, e.g., a colored antibody or chemically modified antibody, e.g., alkaline phosphatase or horseradish peroxidase modified antibody, capable of undergoing a colorimetric change, or a stain or dye able to directly apply color to a microbe or to the substrate. An example of a commercially available colorimetric scanner includes SpotWare™ Colorimetric Microarray Scanners (Arrayit® Corporation, Sunnyvale, Calif.).

In an aspect, the image-capture device includes a fluorescence scanning device. In an aspect, the fluorescence scanning device can include fixed excitation/emission wavelengths based on the use of standard commercially available fluorescent dyes in the green, red, and near infrared wavelengths. For example, the fluorescence scanning device can include a two color scanner for scanning at two distinct wavelengths or wavelength bands. In an aspect, the fluorescence scanning device can include adjustable excitation/emission wavelengths, e.g., with one or more excitation sources and filters to adjust the excitation/emission wavelengths. Non-limiting examples of fluorescent scanners include Fluoroimage 595 or ImageQuant (GE Healthcare Life Sciences, Piscataway, N.J.), Tecan fluorescence scanners (Invitrogen, Carlsbad, Calif.), SureScan Microarray Scanner (Agilent Technologies, Inc., Santa Clara, Calif.), InnoScan® (Innopsys Inc., Chicago, Ill.). Additional examples include fluorescence scanners with motorized stage for line scans across a surface (see, e.g., U.S. Pat. No.

6,371,370 or U.S. Pat. No. 8,385,619, which are incorporated herein by reference), and "stitching together" several image blocks to generate larger image (see, e.g., U.S. Pat. No. 8,041,147, which is incorporated herein by reference).

In an aspect, the image-capture device can be configured to measure the light absorption, light emission, fluorescence, luminescence, chemiluminescence, or phosphorescence associated with the at least one type of microbe. Such electromagnetic properties can be inherent properties of all or a portion of the at least one type of microbe (e.g. auto-fluorescence), or can be associated with one or more signal-generating agents or elements incorporated into or added to the skin-covering material or the at least one type of microbe.

In an aspect, the image-capture device includes one or more imaging sensors including, but not limited to, one or more piezo transducers, one or more MEMS device, one or more cavity resonators, one or more magneto resistive sensors, one or more magnetic field sensors, and/or one or more thermal sensors.

In an aspect, the image-capture device includes components for micro-scanning in which a single CCD sensor with a Bayer filter is moved over the focus plane of the lens to "stitch" together a higher resolution image than the CCD would allow otherwise. In an aspect, the micro-scanning device includes a micro laser scanning device. See, e.g., Seidl et al. (2006) *International Society for Photogrammetry and Remote Sensing.* Volume XXXVI Part 5. Sep. 25-27, 2006, Dresden Germany.

In an aspect, the image-capture device includes a three-dimensional scanning device. Non-limiting examples of three-dimensional scanning devices include NextEngine 3D Scanner (NextEngine, Inc., Santa Monica, Calif.), Handyscan 3D (Creaform USA Inc., Newark, Del.), or Konica Minolta 3D scanners (Konica Minolta, Ramsey, N.J.).

In an aspect, the image-capture device includes a confocal laser scanner. In an aspect, the confocal laser scanner can include a handheld confocal laser scanning microscope (e.g., VIVASCOPE 3000, MAVIG GmbH, Munich, Germany). In an aspect, the confocal laser scanner includes a MEMS confocal laser scanner. See, e.g., Murakami et al. (2003) *The 12th International Conference on Solid State Sensors, Actuators and Microsystems,* Boston, Jun. 8-12, 2003, pp. 587-590, which is incorporated herein by reference.

In an aspect, the image-capture device includes a darkfield scanner capable of scanning an optical pattern of microbes, e.g., bacteria on a solid surface. See, e.g., Adak et al. (2010) *Bioconjug. Chem.* 21:2065-2075, which is incorporated herein by reference.

In an aspect, the image-capture device includes a light source and a detector for measuring reflected and/or absorbed light. In an aspect, the image-capture device measures changes in refractive index on the surface of the skin-covering material. The inner surface can be illuminated with a light source. Resonance occurs at a specific angle of incident light and is dependent on the concentration of microorganisms on the surface. See, e.g., Barlen, et al. (2007) *Sensors,* 7:1427-1446; and Kashyap & Nemova (2009) *J. Sensors*: Article ID 645162, each of which is incorporated herein by reference.

In an aspect, the image-capture device includes a spectrometer or spectrophotometer. In an aspect, the spectrophotometer includes a fiber optic spectrophotometer (from, e.g., Ocean Optics, Dunedin Fla.). In an aspect, the image-capture device includes a means of vibrational spectroscopy. Examples of vibrational spectroscopy include, but are not limited to, Fourier transform infrared (FTIR) spectroscopy and micro-Raman spectroscopy. Raman spectroscopy can further include UV-resonance Raman spectroscopy, surface enhanced Raman scattering, or tip-enhanced Raman scattering. See, e.g., Harz et al. (2009) *Cytometry A* 75:104-113, which is incorporated herein by reference. In general vibrational spectra from different bacterial and yeast species and strains share similar bands, but the relative amounts of these components vary between different species and strains.

In an aspect, the image-capture device includes a light source, a digital projector, a CCD camera and a computing device for image-processing for spatial frequency domain imaging, a wide field optical technique.

In an aspect, the image-capture device includes a lens-free imaging system. See, e.g., Kim et al. (2012) *J. Lab. Automation* 17:43-49, which is incorporated herein by reference.

In an aspect, the scanner includes a type of flatbed commercial scanner. For example, a flatbed commercial scanner can be used to image visible color associated with at least one type of microbe bound to the inner surface of the skin-covering material. In an aspect, a commercial flatbed scanner can be combined with a laser-directed energy source and one or more lens to create a gigapixel inline digital holographic microscope capable of scanning a 297 mm by 210 mm area, as described in Shimobaba et al. (2013) *Optical Society of America.* arXiv:1305.6084v1 [physics.optics] 27 May 2013, which is incorporated herein by reference. In an aspect, the scanner includes a mechanical means for feeding the skin-covering material into the scanning device so as to scan the inner surface of the skin-covering material in parts.

In an aspect, the scanner includes an acoustic scanning device capable of using focused sound to image the at least one type of microbe captured on the inner surface of the skin-covering material. See, e.g., Hildebrand et al. (1981) *Proc. Natl. Acad. Sci., USA.* 78:1656-1660, which is incorporated herein by reference.

In an aspect, the image-capture device captures one or more signals emitted or reflected from at least one type of microbe captured on the microbe-capture region on the inner surface of the skin-covering material. In an aspect, the one or more signals from the at least one type of microbe captured on the microbe-capture region are representative of one or more properties of the at least one type of microbe. The one or more properties can include one or more inherent properties or characteristics of the at least one type of microbe that are measureable by the image-capture device. In an aspect, the one or more properties of the at least one type of microbe can include at least one of an optical property, autofluorescence property, an infrared spectral property, a reflective property, a light scattering property, or an opacity property of the at least one type of microbe.

In an aspect, the image-capture device captures one or more signals associated with autofluorescence emitted from the at least one type of microbe in response to a directed energy applied to the microbe-capture region. Autofluorescence emitted from the at least one type of microbe can be captured by the image-capture device. In an aspect, image-capture device 120 includes a fluorescence scanning device. In an aspect, the fluorescence scanning device includes a fluorescence laser scanner configured to detect cellular auto-fluorescence emitted from microbes captured on the inner surface of the skin covering in response to exposure to directed energy, e.g., light of a certain wavelength. For example, naturally occurring autofluorescence emitted by microbes may be derived from fluorophore-containing biomolecules associated with the microbes, e.g., porphyrins, certain amino acids, flavins, and coenzymes NADP and NADPH (see, e.g., Koenig et al. (1994) *J. Fluoresc.* 4:17-40) which is incorporated herein by reference). In an aspect, the fluorescence scanning device can include directed energy that includes one or more excitation wavelengths for exciting autofluorescence emission from captured microbes. For example, the excitation maxima of endogenous fluorophores, e.g., porphyrins, lie in the range of 250-450 nm (spanning the ultraviolet/visible (UV/VIS) spectral range), whereas their emission maxima lie in the range of 280-540 nm (see, e.g., Ammor (2007) *J. Fluoresc.* 17:455-459, which is incorporated herein by reference). See, e.g., U.S. Patent Application 2011/0117025, which is incorporated herein by reference.

In an aspect, autofluorescence associated with naturally occurring, endogenous prophyrins can be used to detect bacteria. For example, a number of skin-associated bacteria produce protophorphyrins, including *Propinibacterium acnes, Staphylococcus aureus, Clostridium, Bifidobacterium*, and *Actinomyces* (see, e.g., Koenig et al. (1994) *J. Fluoresc.* 4:17-40, which is incorporated herein by reference). In an aspect, bacteria may be detected using fluorescence lifetimes measured at 430, 487, and 514 nm after selective excitation at 340, 405, and 430 as described by Bouchard et al. (2006) in *J. Biomed. Opt.* 11:014011, 1-7, which is incorporated herein by reference. In another example, autofluorescence may be used to detect *Staphylococcus* sp. and/or *Pseudomonas aeruginosa* using a scanning device emitting electromagnetic energy at a wavelength of 488 nm as described by Hilton (1998) *SPIE* 3491:1174-1178, which is incorporated herein by reference. For example, *Staphylococcus aureus* may be distinguished from *Escherichia coli* based on emission spectra induced by excitations at 410-430 nm (see, e.g., Giana et al. (2002) *J. Fluoresc.* 13:489-493, which is incorporated herein by reference).

In an aspect, autofluorescence may be used to detect fungi. For example, *Candida albicans* irradiated with electromagnetic energy at wavelengths of 465-495 nm autofluoresces at an emission wavelength of 515-555 mm (see, e.g., Mateus et al. (2004) *Antimicrob. Agents Chemother.* 48:3358-3336, which is incorporated herein by reference). For example, *Aspergillus* may be detected using autofluorescence in response to excitation at 450-490 nm and emission at 560 (see, e.g., Graham (1983) *Am. J. Clin. Pathol.* 79:231-234, which is incorporated herein by reference).

In an aspect, autofluorescence may be used to distinguish between different types of microbes, e.g., bacteria versus fungi. For example, bacteria, e.g., *Lactobacillus*, and fungi, e.g., *Saccharomyces*, can be differentiated using fluorescence spectroscopy, each having its own spectral fingerprint. See, e.g., Bhatta et al. (2006) *Appl. Microbiol. Biotechnol.* 71:121-126, which is incorporated herein by reference. For example, a number of skin associated fungi, e.g., dermatophytosis and tinea, exhibit autofluorescence. See, e.g., Elston (2001) *BMC Microbiology* 1:21, which is incorporated herein by reference.

The autofluorescence emitted by one or more microbes can be measured by a photosensor such as, for example, a charge coupled device (CCD) and/or a complementary metal oxide semiconductor (CMOS) sensor associated with the image-capture device. The captured information may be processed internally by the image-capture device or sent to the computing device for processing. The information is compared with preset algorithms defining, for example, the autofluorescence properties of reference microbes.

In an aspect, the image-capture device can include an optical scanning device. The microbes may be imaged using any of a number of imaging or optical methods including among other things light scattering, electrical impedance, infrared spectroscopy, acoustic imaging, thermal imaging, photothermal imaging, visible light absorption and refraction, and autofluorescence. See, e.g., Doornbos et al. (1993) *Cytometry* 14:589-594; Gao et al. (2003) *Proceedings of the 25th Annual International Conference of the IEEE EMBS*, Cancun, Mexico, Sep. 17-21, 2003; Oberreuter et al. (2002) *Int. J. Syst. Evol. Microbiol.* 52:91-100; Baddour et al. (2002) *Ultrasonics Symposium IEEE* 2:1639-1644; Zharov et al. (2006) *J. Biochem.* 97:916-932; Zharov et al. (2006) *J. Biomed. Opt.* 11:054034-1-4; Koenig et al. (1994) *J. Fluoresc.* 4:17-40; which are each incorporated herein by reference. In an aspect, the image-capture device can include a scanning laser beam and a charge-coupled device camera to acquire light scatter-image signatures. See, e.g., Huff et al. (2012) *Microbial Biotechnology* 5:607-620, which is incorporated herein by reference.

In an aspect, the image-capture device is able to detect luminescence. In an aspect, the image-capture device is able to detect chemiluminescence, e.g., light, emitted from the inner surface of the skin-covering material as a result of a chemical reaction. For example, the interaction of luminol with hydrogen peroxide in the presence of iron or copper and enhanced by horseradish peroxidase results in emitted light. Chemiluminescence on a solid substrate can be detected using a CCD camera system (e.g., GeneGnome5, Syngene USA, Fredrick Md.).

In an aspect, the one or more properties include reflective properties. The reflective properties, e.g., color, can be detected with a camera or other image-capture device.

In an aspect, the one or more properties of the at least one type of microbe can include infrared spectral properties. In general, cells including microbes contain various chemical components with characteristic infrared spectra, including proteins, nucleic acids, carbohydrates and lipids. The spectra are created when a molecule converts infrared radiation into molecular vibrations. These vibrations create bands in a spectrum that occur at specific wavelengths. Differences in the chemical composition of a microbe can be distinguished by changes in spectra. For example, Fourier Transfer Infrared (FTIR) Spectroscopy can be used to distinguish *Streptococcus* from a virus using a spectral range of wavenumbers from 4000 to 800 cm1 (U.S. Pat. No. 6,379,920, which is incorporated herein by reference). Alternatively, FTIR data may be obtained at various frequency ranges, such as for example, 3000-2800 $cm^{-1}$, 1800-1500 $cm^{-1}$, 1500-1200 $cm^{-1}$, and 1200-900 $cm^{-1}$, and 900-700 $cm^{-1}$ and spectra obtained in these various ranges compared with known spectra of various bacteria. See, e.g., Oberreuter et al. (2002) *Int. J. Syst. Evol. Microbiol.* 52:91-100 and Helm et al. (1991) *J. General Microbiology* 137:69-79, which are incorporated herein by reference.

In one or more embodiment, the one or more properties of the at least one type of microbe can include thermal properties. Thermal energy, e.g., infrared energy, emitted from the at least one type of microbe can be detected using infrared photosensors, e.g., indium gallium arsenide or mercury cadmium telluride based photosensors.

In an aspect, the one or more properties of the at least one type of microbe can include one or more of a size, a morphological property, or a physical feature. For example, the image-capture device can be configured to detect by optical or other means the shape, outline, and/or periphery of the at least one type of microbe on the inner surface of the skin-covering material. The shape, outline, and/or periphery can be further used to determine a size, a morphological property, or a physical feature of the at least one type of microbe. For example, bacteria typically range in size from 0.5 to 5.0 micrometers. Common morphologies of bacteria include spherical, e.g., cocci, or rod shaped, e.g., bacilli. Additional morphologies include corkscrew, filamentous, helical, enlarged rod, spirochete. Physical features include hypha or stock of budding or appendaged bacteria or flagella. In contrast, fungi can be multicellular or unicellular. Multicellular fungi are composed of filamentous hyphae. Unicellular fungi include a wide variety of budding yeast. Some fungi, such as *Candida*, are dimorphic with yeast phases and filamentous phases. Viruses range in size from 20 to 300 nanometers. The use of contrast agents, e.g., a tungsten heavy electron dense stain, can increase contrast to aid in visualizing viruses and other microbes. In an aspect, physical features may also include intracellular shapes, outlines, and/or peripheries, e.g., of organelles and the like associated with a type of microbe. In an aspect, the size of the microbe is correlated with its light scattering properties. See, e.g., Ulicny (1992) *Gen. Physiol. Biophys.* 11:133-151, which is incorporated herein by reference.

In an aspect, the at least one type of microbe can be identified based on pattern and image recognition or signal recognition analysis. Various methods have been described for image and shape analysis of cells and subcellular components of cells. See, e.g., Fei-Fei et al. (2006) *IEEE Transactions on Pattern Analysis and Machine Intelligence* 28:594-611; and Martin et al. (2004) *IEEE Transactions on Pattern Analysis and Machine Intelligence* 26:530-549, which are incorporated herein by reference.

In an aspect, the one or more properties of the at least one type of microbe include at least one of metabolic properties, lipid properties, carbohydrate properties, protein properties, or genomic properties of the at least one type of microbe.

In an aspect, the at least the inner surface of the skin-covering material includes one or more label-free optical biosensors that incorporate other optical methodologies, e.g., interferometers, waveguides, fiber gratings, ring resonators, and photonic crystals. See, e.g., Fan, et al., *Anal. Chim. Acta* 620:8-26, 2008, which is incorporated herein by reference.

Returning to FIG. 1, system 100 further includes computing device 130 including a processor and operably coupled to image-capture device 120. Computing device 130 can take various forms or be part of an object, and can include, but is not limited to, a computer, a laptop computer, a personal electronic device, a dedicated computing device, a limited resource computing device, a wireless communication device, a mobile wireless communication device, a handheld electronic writing device, a tablet, a digital camera, a scanner, a cell phone, a PDA, an electronic tablet device, a printer, or any other like device that takes information as an input and gives it back to the end-users. Computing device 130 can include a digital single processor, ASIC, microprocessor, or other type of processor operating on a system such as a personal computer, server, a router, of other device capable of processing data including network interconnection device. In an aspect, computing device 130 and image-capture device 120 are incorporated into a single unit. In an aspect, computing device 130 is part of a kiosk.

Computing device 130 further includes circuitry configured to receive a digital output from image-capture device 120 including information associated with at least one property and a spatial distribution of the at least one type of microbe bound to the microbe-capture region; compare the at least one property of the at least one type of microbe with a database of reference microbe properties; and generate a digital profile 180 including the at least one property and the spatial distribution of the at least one type of microbe bound to the microbe-capture region of skin-covering material 110. In an aspect, computing device 130 includes circuitry configured to identify the at least one type of microbe bound to the microbe-capture region based on comparison of the at least one property of the at least one type of microbe with the database of reference microbe properties. For example, computing device 120 can include a database containing a reference library of microbes and associated autofluorescence properties at given excitation wavelengths. For example, computing device 130 can include a database containing a reference library of microbes and associated optical, fluorescence, reflective, light scattering, opacity, magnetic, acoustic, infrared spectral, electromagnetic, or electrical properties. For example, computing device 130 can include a database containing a reference library of microbes and size, morphological properties, and physical features. For example, computing device 130 can include a database containing a reference library of microbes and their protein properties, carbohydrate properties, metabolic properties, lipid properties, or genomic properties. In an aspect, computing device 130 includes one or more algorithms to process the digital output provided by the image capture device. For example, the one or more algorithms can include an algorithm for assessing the number of microbes in an image field. See, e.g., Selinummi et al., (2005) *BioTechniques* 29:859-863, which is incorporated herein by reference In an aspect, computing device 130 further includes circuitry configured to generate a digital alignment of the digital profile of the at least one type of microbe bound to the microbe-capture region of the skin-covering material with a digital image of the skin surface of the individual covered by the microbe-capture region of the skin-covering material. In an aspect, one or more digital images of the skin surface of the individual can be captured with a digital camera, for example, before or after placement of the skin-covering material onto the skin surface. One or more registration marks on the skin-covering material may be used to register the skin-covering material relative to landmarks on the skin surface incorporated into the digital image of the skin surface. For example, skin-covering material 110 may include at least one registration mark to register the skin-covering material to at least one landmark on the skin surface of the individual. One or more registration marks on the skin-covering material can be used to align with one or more landmarks on the skin surface. The one or more landmarks can include one or more of pigmentation, pigmented areas, tattoos, skin texture patterns, blemishes, scars, anatomical features, or subsurface blood vessels associated with the skin surface. In an aspect, the one or more registration marks are incorporated into the manufacture of the skin-covering material based on the presence of landmarks in the one or more digital images of the skin surface used to form the skin-covering material. In an aspect, the one or more registration marks can be added, e.g., with a pen or other marking device, while the skin-covering material is on the skin-surface of the individual. The digital profile and the one or more images of the underlying skin surface can be aligned using any of a number of image registration algorithms, programs, or software.

In an aspect, the computing device includes circuitry configured to detect one or more features depicted in the digital images, e.g., the physical landmarks, and match these features with features in the digital spatial profile, e.g., the registration marks. Features and the relationships between them may be detected using any of a number of feature-based methods including, but not limited to, segmentation methods, distance transform, affinely invariant neighborhoods, Harris corner detection, Maximally Stable External Regions, Canny detector, Laplacian of Gaussian, elastic contour extraction, existing edge detection, line intersections, local extrema of wavelet transform, inflection points of curves, and the like. The computing device is further operable to match the features detected in the one or more images of skin surface of the individual with features in the digital spatial profile using one or more feature-matching methods, non-limiting examples of which include Euclidean distance matching, invariant moments, nearest neighbor based matching, correlation-like methods, Fourier methods, mutual information methods, optimization methods. Further non-limiting examples include methods using spatial relations, e.g., graph matching algorithms, methods using invariant descriptors, and relaxation methods. The following references are incorporated by reference and include descriptions of computational methods for image registration: Szeliski *Foundations and Trends in Computer Graphics and Vision*, Vol. 2, No. 1 (2006) 1-104, Zitova & Flusser *Image Vision Computing* (2003) 21:977-1000.

In an aspect, computing device 130 further includes circuitry configured to report to a user a personalized microbe profile, the personalized microbe profile including an identity of the at least one type of microbe and a spatial distribution of the identified at least one type of microbe on the skin surface of the individual. The personalized microbe profile may be generated from the digital alignment of the digital profile of the at least one type of microbe bound to the microbe-capture region of the skin-covering material with a digital image of the skin surface of the individual. The one or more registration marks can be used to help align the digital profile with the digital image of the skin surface. In an aspect, the user includes the individual, e.g., the individual for whom the personalized microbe profile is generated. In an aspect, the user includes a service-provider, e.g., a medical professional or cosmetologist who performs the steps to generate the personalized microbe profile for an individual. In an aspect, the user includes a third party individual, e.g., a manufacturer, an insurance company and/or a research group.

In an aspect, computing device 130 includes circuitry configured to provide a visual representation of the personalized microbe profile on a display. In an aspect, the display is operably coupled to computing device 130. For example, a visual representation of an individual's personalized microbe profile may be shown on a display of a computing device in a medical professional or cosmetologist office. For example, a visual representation of an individual's personalized microbe profile may be shown on display of a kiosk. In an aspect, the display is operably coupled to a second computing device. For example, the personalized microbe profile may be available on a display associated with a hand-held device, e.g., a smartphone device.

In an aspect, computing device 130 includes circuitry configured to provide a printout to a user, the printout including the personalized microbe profile. The printout can include textual description and/or visual representation of the personalized microbe profile. For example, the printout may provide the personalized microbe profile as a textual description, e.g., identification of the at least one type of microbe on the skin surface of the individual and generally where the microbes are distributed, e.g., the nose area, the "T-zone," the forehead, and the like. For example, the printout may provide the personalized microbe profile as a hardcopy version of the visual representation shown on a display.

In an aspect, computing device 130 includes circuitry configured to export information regarding the personalized microbe profile to at least one second computing device. For example, the personalized microbe profile may be generated on a first computing device, e.g., in a service-provider's office, and subsequently downloaded to one or more computing devices accessible by the individual, e.g., a home computer or a smartphone device. For example, the personalized microbe profile may be generated by computing device associated with a kiosk and subsequently downloaded to one or more computing devices accessible by the individual. In an aspect, the at least one second computing device is associated with a retailer capable of providing a recommended treatment regimen, e.g., a pharmacy, a cosmetic counter, or other retailer. In an aspect, the at least one second computing device is associated with a manufacturer, e.g., the manufacturer of the skin-covering material and/or a component of a treatment regimen. In an aspect, the at least one second computing device is associated with a third party payer, e.g., an insurance company. In an aspect, the at least one second computing device is associated with a research group.

In an aspect, computing device 130 includes circuitry configured to generate a treatment recommendation based on an identity and a spatial distribution of the at least one type of microbe on the skin surface of the individual. For example, the circuitry can be configured to generate a treatment recommendation including a antimicrobial treatment based on the types of microbes present, e.g., antibiotics for bacteria, fungicide for fungus, or antiviral for a virus. For example, the circuitry can be configured to generate a treatment recommendation including a type of skin cleaning process, e.g., a type of soap or antiseptic rinse, based on the identity and the distribution of the at least one type of microbe. For example, the circuitry can be configured to generate a treatment recommendation including one or more probiotics or prebiotics to alter the microbe profile on the skin surface, e.g., to balance beneficial microbes against harmful microbes. For example, the circuitry can be configured to generate a treatment recommendation including a certain type of cosmetic product that is compatible with the microbes present, e.g., helps to maintain beneficial microbes but discourages harmful microbes and can include probiotics and/or prebiotics. For example, the circuitry can be configured to generate a treatment recommendation including one or more medicaments, e.g., hormone creams, oral hormones, or retinoid creams. Non-limiting examples of treatment recommendations include antimicrobial agents, cleansing products, cosmetic products, probiotics, prebiotics, medicaments, procedures (e.g., shaving or not in sensitive areas, applying warm compresses to open pores, use of a pore-opening or cleaning device, abrasion, and the like), and changes in diet. In an aspect, the circuitry can be configured to alert the individual as to whether the identity and the spatial distribution of the at least one type of microbe warrants discussion with a medical professional. In an aspect, the computing device includes circuitry configured to report to the user the recommended treatment regimen including via a display, a printout, or exportation of data to another device, e.g., a personal handheld device.

Figure 2:
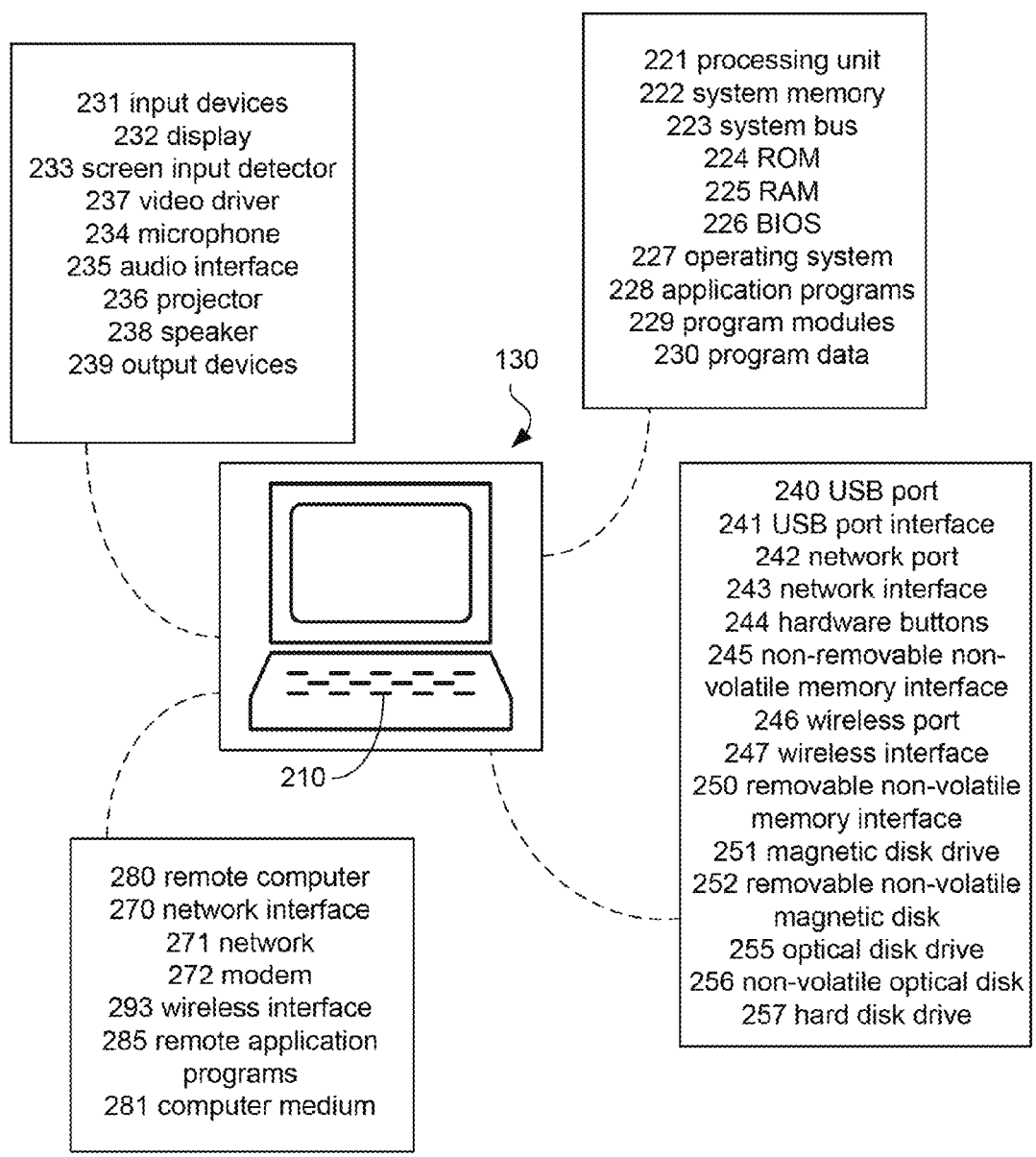
FIG. 2 is a schematic of a computing device.

FIG. 2 illustrates further embodiments of computing device 130 for use in a system for assessing the microbiota of skin. Computing device 130 includes a processing unit 221, a system memory 222, and a system bus 223 that couples various system components including the system memory 222 to the processing unit 221. Processing unit 221 can include a microprocessor, a central processing unit (CPU), a digital signal processor (DSP), an application-specific integrated circuit (ASIC), a field programmable gate entry (FPGA), or the like, or any combinations thereof, and can include discrete digital or analog circuit elements or electronics, or combinations thereof. In an aspect, the computing device includes one or more ASICs having a plurality of pre-defined logic components. In an aspect, the computing device includes one or more FPGA having a plurality of programmable logic commands.

The system bus 223 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus, also known as Mezzanine bus.

Computing device 130 includes a user interface, e.g., one or more input devices 231 and/or output devices 239 for use by a user to interface with the computing device. The one or more input devices 231 can be used to enter information into the computing device and may be integrated into the computing device or may be one or more peripheral devices operably connected through a wired or wireless connection to the computing device. Non-limiting examples of input devices 231 include a graphical user interface, a display, a keyboard, a keypad, a trackball, a joystick, a touch-screen, a mouse, a microphone, an image scanner, a digital camera, a webcam, a light pen, a bar code reader, a fingerprint scanner, a retinal scanner, a game pad, a stylus pen a switch, a dial, or the like. In an aspect, the input device 231 is part of a kiosk structure.

The user interface may include a character, a key-based, or another user data input via a keyboard or touch sensitive display. The user interface may include using a stylus (not shown). Moreover, the user interface is not limited to an actual touch-sensitive panel arranged for directly receiving input, but may alternatively or in addition respond to another input device such as a microphone. A user may enter commands and information into the computing device 130 through user input devices, such as a number of switches and buttons, illustrated as hardware buttons 244, connected to the system via a suitable interface 245. Input devices 231 may further include a touch-sensitive display with suitable input detection circuitry, illustrated as a display 232 and screen input detector 233. The output circuitry of the touch-sensitive display 232 is connected to the system bus 223 via a video driver 237. Other input devices may include a microphone 234 connected through a suitable audio interface 235, and a physical hardware keyboard 210. Output devices may include at least one of the display 232, or a projector display 236. Input device 231 may further include a microphone, keyboard, or pointing device, commonly referred to as a mouse, trackball, or touch pad. Other input devices may include at least one of a touch sensitive display, joystick, game pad, satellite dish, and scanner.

The user interface includes one or more output devices 239 over which processed information is viewed as output results and may be integrated into the computing device or may be one or more peripheral devices operably connected through a wired or wireless connection to the computing device. Non-limiting examples of output devices 239 include but are not limited to television screens, computer monitors, liquid crystal displays, audio speakers, audio headphones, and printers. In an aspect, the computing device 130 may include at least one speaker 238 connected through a suitable audio interface 235. The one or more output devices 239 can be used to report to a user an identification and/or a spatial distribution of at least one type of microbe on a skin surface of an individual. In an aspect, the input/output devices include image-capture device 120 connected through a wired or wireless connection to the computing device.

In an aspect, the one or more input/output devices are connected to the processing unit of the computing device through one or more user input interfaces that are coupled to the system bus, but may be connected by other interfaces and bus structures, such as a parallel port, game port, or a universal serial bus (USB). For example, input devices 231 or output devices 239, may be connected to the processing unit 221 through a USB port 240 and USB port interface 241, to the system bus 223. Alternatively, the other external input devices 231 and output devices 239 may be connected by other interfaces, such as a parallel port, game port or other port. The computing device 130 may further include or be capable of connecting to a flash card memory (not shown) through an appropriate connection port (not shown). The computing device 130 may further include or be capable of connecting with a network through a network port 242 and network interface 243, and through wireless port 246 and corresponding wireless interface 247 may be provided to facilitate communication with other peripheral devices, for example, the scanning device. It will be appreciated that the various components and connections shown are examples and other components and means of establishing communication links may be used.

In an aspect, image-based applications such as viewers and/or toolkits (e.g., Insight Segmentation and Registration Toolkit (ITK)), are incorporated for further intake of information. In an aspect, CAD implementations, image segmentation, or other image analysis algorithms may allow processing of images received from an image capture device.

The system memory includes read-only memory (ROM) 224 and random access memory (RAM) 225. A basic input/output system (BIOS) 226, containing the basic routines that help to transfer information between sub-components within computing device 130, such as during start-up, is stored in the ROM 224. A number of program modules may be stored in the ROM 224 or RAM 225, including an operating system 227, one or more application programs 228, other program modules 229 and program data 230.

Computing device 130 includes computer-readable media products and may include any media that can be accessed by the computing device 130 including both volatile and non-volatile media, removable and non-removable media. By way of example, and not of limitation, computer-readable media may include non-transitory signal-bearing media. By way of example, and not of limitation, computer-readable media may include computer storage media. By way of further example, and not of limitation, computer-readable media may include a communication media.

Communication media may typically embody computer-readable instructions, data structures, program modules, or other data in a modulated data signal such as a carrier wave or other transport mechanism and include any information delivery media. The term "modulated data signal" means a signal that has one or more of its characteristics set or changed in such a manner as to encode information in the signal. By way of example, and not limitation, communication media include wired media, such as a wired network and a direct-wired connection, and wireless media such as acoustic, RF, optical, and infrared media.

Computing device 130 may also include other removable/non-removable, volatile/nonvolatile computer storage media products implemented in any method or technology for storage of information such as computer-readable instructions, data structures, program modules, or other data. For example, such media includes a non-removable non-volatile memory interface (hard disk interface) 245 reads from and writes for example to non-removable, non-volatile magnetic media, or a removable non-volatile memory interface 250 that, for example, is coupled to a magnetic disk drive 251 that reads from and writes to a removable, non-volatile magnetic disk 252, or is coupled to an optical disk drive 255 that reads from and writes to a removable, non-volatile optical disk 256, such as a CD ROM. Other removable/nonremovable, volatile/non-volatile computer storage media that can be used in the example operating environment include, but are not limited to, magnetic tape cassettes, magnetic tape, magnetic disk storage, optical disk storage, memory cards, flash memory cards, DVDs, electrically erasable programmable read-only memory (EEPROM), digital video tape, solid state RAM, and solid state ROM or any other medium which can be used to store the desired information and which can be accessed by the computing device 130. The hard disk drive 257 is typically connected to the system bus 223 through a non-removable memory interface, such as the interface 245, and magnetic disk drive 251 and optical disk drive 255 are typically connected to the system bus 223 by a removable non-volatile memory interface, such as interface 250. In an aspect, computing device 130 includes a computer-readable media drive or memory slot configured to accept non-transitory signal-bearing medium (e.g., computer-readable memory media, computer-readable recording media, or the like). In an aspect, a computer storage media may include a group of computer storage media devices. In an aspect, a computer storage media may include an information store. In an aspect, an information store may include a quantum memory, a photonic quantum memory, or atomic quantum memory. Combinations of any of the above may also be included within the scope of computer-readable media.

In an aspect, a program or set of instructions for causing a system to execute any of the disclosed methods can be stored on, for example, a computer-readable recording medium (CRMM), a non-transitory signal-bearing medium, or the like. Non-limiting examples of signal-bearing media include a recordable type medium such as magnetic tape, floppy disk, a hard disk drive, Compact Disc (CD), a Digital Video Disk (DVD), Blu-Ray Disc, digital tape, computer memory, or the like, as well as transmission type medium such as a digital and/or analog communication medium (e.g., fiber optic cable, waveguide, wired communications link, wireless communication link). Further non-limiting examples of signal-bearing media include, but are not limited to, DVD-ROM, DVD-RAM, DVD+RW, DVD-RW, DVD-R, DVD+R, CD-ROM, Super Audio CD, CD-R, CD+R, CD+RW, CD-RW, Video Compact Discs, Super Video Discs, flash memory, magnetic tape, magneto-optic disk, MINIDISC, non-volatile memory card, EEPROM, optical disk, optical storage, RAM, ROM, system memory, web server, cloud, or the like.

The drives and their associated computer storage media discussed above provide storage of computer-readable instructions, data structures, program modules, and other data for the computing device 130.

The computing device may operate in a networked environment using logical connections to one or more remote computers, such as a remote computer 280. The remote computer 280 may be a personal computer, a server, a router, a network PC, a peer device, or other common network node, and typically includes many or all of the elements described above relative to the computing device 130. The network logical connections include a local area network (LAN) and a wide area network (WAN), and may also include other networks such as a personal area network (PAN) (not shown). Such networking environments are commonplace in offices, enterprise-wide computer networks, intranets, and the Internet.

When used in a networking environment, the computing device is connected to the network 271 through a network interface, such as the network interface 270, the modem 272, or the wireless interface 293. The network may include a LAN network environment, or a WAN network environment, such as the Internet. In a networked environment, program modules depicted relative to the computing device 130, or portions thereof, may be stored in a remote memory storage device. By way of example, and not limitation, remote application programs 285 as residing on computer medium 281. It will be appreciated that the network connections shown are examples and other means of establishing communication link between the computers may be used.

In some embodiments, the computing device includes one or more modules optionally operable for communication with one or more input/output components that are configured to relay user output/input. In an aspect, a module includes one or more instances of electrical, electromechanical, software-implemented, firmware-implemented, or other control devices. Such devices include one or more instances of memory, computing devices, antennas, power or other supplies, logic modules or other signaling modules, gauges or other such active or passive detection components, piezoelectric transducers, shape memory elements, micro-electromechanical systems (MEMS) elements, or other actuators.

In certain instances, one or more elements of the computing device 130 may be deemed not necessary and omitted. In other instances, one or more other components may be deemed necessary and added to computing device 130.

Figure 3:
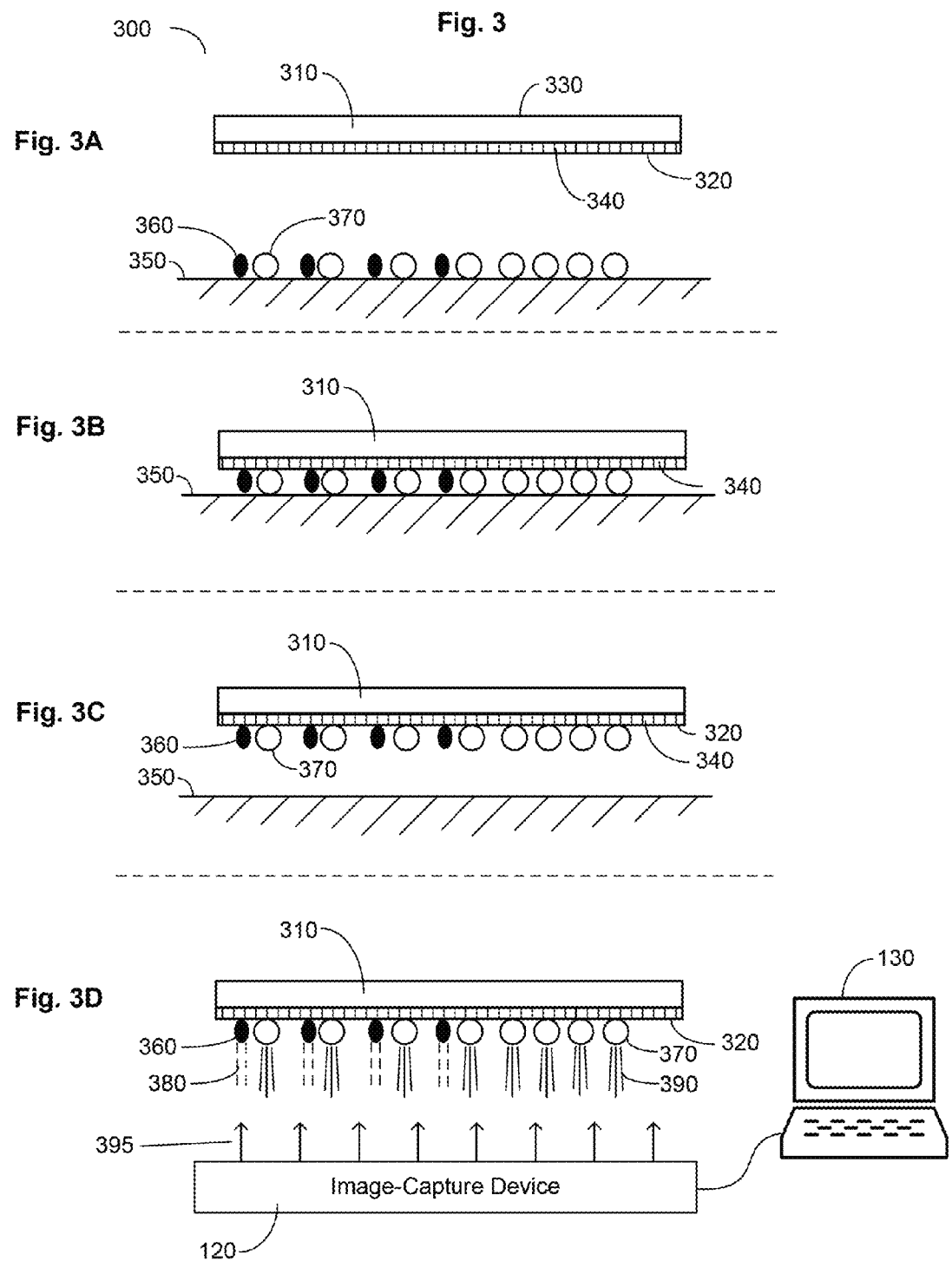
FIGS. 3A-3D illustrate aspects of a system including a pre-formed skin covering material for assessing microbiota of skin.

FIG. 3 illustrates a system for assessing microbiota of skin including a pre-formed skin-covering material that includes a microbe-capture region. System 300 includes pre-formed skin-covering material 310, image-capture device 120, and computing device 130. Pre-formed skin-covering material 310 includes an inner surface and an outer surface, the inner surface substantially conforming in shape to a topography of a skin surface of an individual and including microbe-capture region. Image-capture device 120 includes circuitry to capture at least one image of the inner surface of pre-formed skin-covering material 310 and to transform the captured at least one image into a digital output including information associated with at least one property and a spatial distribution of at least one type of microbe bound to the microbe-capture region. Computing device 130 includes a processor and is operably coupled to image-capture device 120. Computing device 130 further includes circuitry configured to receive the digital output from image-capture device 120 including information associated with at least one property and a spatial distribution of the at least one type of microbe bound to the microbe-capture region; compare the at least one property of the at least one type of microbe with a database of reference microbe properties; and generate a digital profile including the at least one property and the spatial distribution of the at least one type of microbe bound to the microbe-capture region of pre-formed skin-covering material 310.

As shown in FIG. 3A, pre-formed skin-covering material 310 includes inner surface 320 and outer surface 330, wherein inner surface 320 substantially conforms to a topography of skin surface 350 of an individual. Inner surface 320 includes microbe-capture region 320 configured to capture at least one type of microbe 360, 370 from skin surface 350 of the individual. Inner surface 320 further includes microbe-capture region 340 configured to capture at least one first type of microbe 360 and at least one second type of microbe 370 from skin surface 350 of the individual. First type of microbe 360 and second type of microbe 370 can include one or more type of bacteria, fungus, virus, or parasite as described above herein.

In FIG. 3B, microbe-capture region 340 of pre-formed skin-covering material 310 is in physical contact with skin surface 350. Skin-surface 350 can include skin associated with any portion of the body including face, head, neck, torso, or extremities, as well as accessible skin surfaces associated with a body orifice, e.g., associated with nose, vagina, mouth, throat, urethra, rectum, or ears.

In FIG. 3C, pre-formed skin-covering material 310 has been separated from skin-surface 350 and at least one first type of microbe 360 and at least one second type of microbe 370 are attached to microbe-capture region 340 on inner surface 320 of pre-formed skin-covering material 310. In FIG. 3D, inner surface 320 of pre-formed skin-covering material 310 is imaged using image-capture device 120. In this example, image-capture device 120 includes a scanning device which excites microbe-capture region 340 and bound microbes with directed energy 395. In response, signals, e.g., autofluorescence, are emitted from microbe-capture region 340, e.g., one or more first signals 380 from at least one first type of microbe 360 and one or more second signals 390 from at least one second type of microbe 370. Image-capture device 120 is operably coupled to computing device 130 and transforms the one or more signals into output data for receipt by computing device 130.

Microbe-capture region 340 can include one or more materials configured to capture at least one type of microbe when inner surface 320 of skin-covering material 310 is placed in physical contact with the skin surface of an individual. In an aspect, microbe-capture region 340 can include one or more materials configured to non-selectively capture microbes from the skin surface of the individual. In an aspect, microbe-capture region 340 covers at least a portion of inner surface 320 of the semi-rigid skin-covering material 310. In an aspect, microbe-capture region 340 covers the entirety of inner surface 320 of the semi-rigid skin-covering material 310. In an aspect, microbe-capture region 340 is an integral part of semi-rigid skin-covering material 310. For example, one or more materials used to form semi-rigid skin-covering material 310 may include properties, e.g., "tackiness" or charge properties, which allow for non-selective capture of one or more types of microbes from a skin surface. In an aspect, microbe-capture region 340 forms a separate layer on inner surface 320 of semi-rigid skin-covering material 310. For example, microbe-capture region 340 may include a material, e.g., a liquid or a gel, which is spread on inner surface 320 of previously formed semi-rigid skin-covering material 310.

In general, microbe-capture region 340 can include one or more materials that non-selectively interact with biomolecules on the outer surface of microbes, e.g., proteins, polysaccharides, carbohydrates, phospholipids, proteoglycans, and the like. In an aspect, the one or more materials take advantage of hydrogen bonding, electrostatic and/or hydrophobic interactions to capture microbes from the skin surface onto microbe-capture region 340. Non-limiting examples of materials for use in microbe-capture region 340 include poly-ionic surfaces, e.g., poly-cationic surfaces such as polyamino acids (e.g., polylysine) and fibronectin for binding microbes that have an overall negative surface charge. Other non-limiting examples of materials for use in microbe-capture region 340 include nitrocellulose, cellulose nitrate, hydrophobic polymers, PVDF coated surface, nylon coated surface, streptavidin coated substrate to bind biotin labeled microbes, protein, peptide, Concanavalin A, and/or NHS-ester coated surface.

Figure 4:
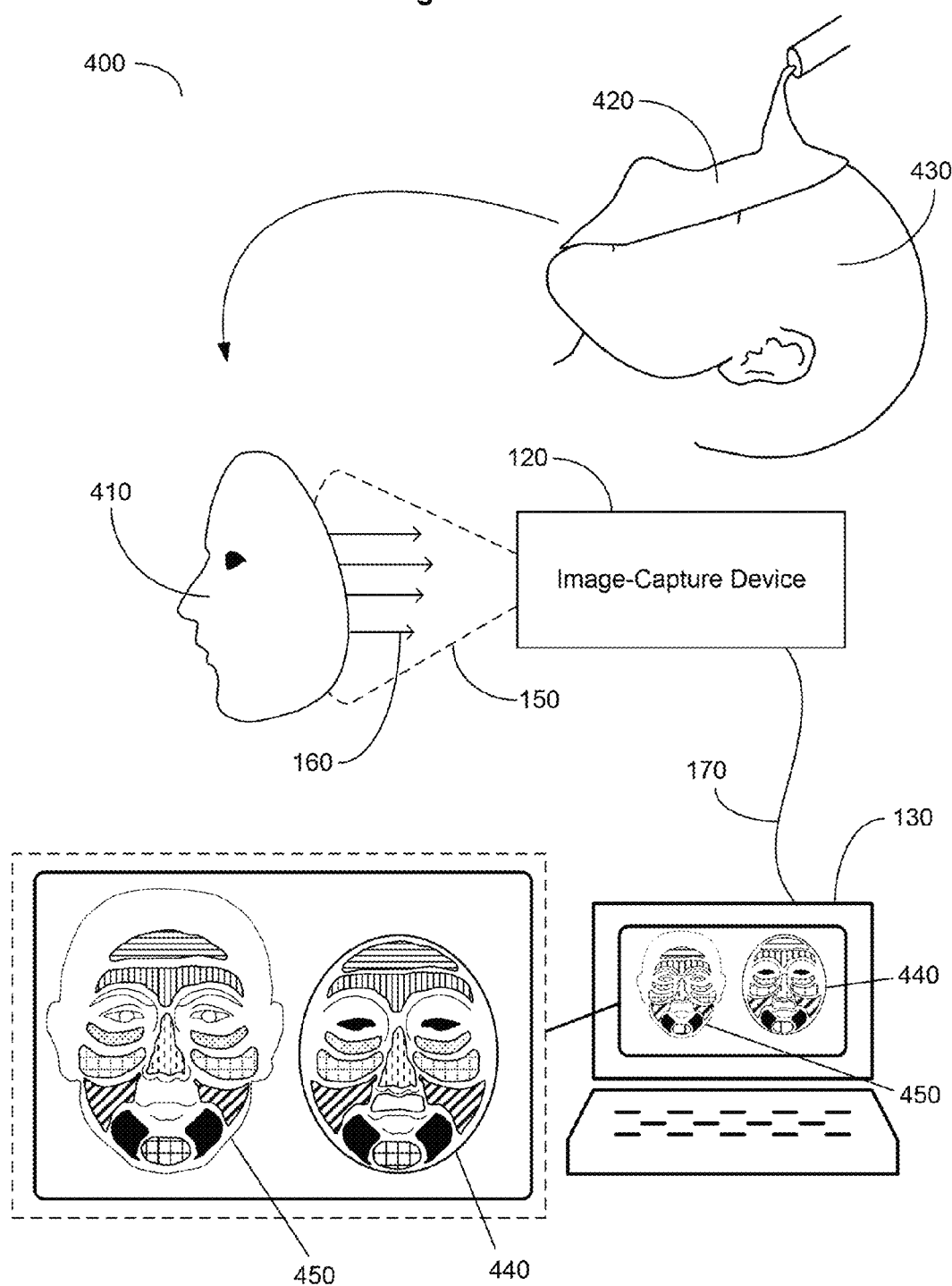
FIG. 4 is a schematic of a system for assessing microbiota of skin.

FIG. 4 illustrates aspects of a system for assessing the microbiota of the skin. System 400 includes peelable skin-covering material 410, image-capture device 120, and computing device 130 including a processor. Computing device 130 includes a processor and is operably coupled through communication link 170 to image-capture device 120. Peelable skin-covering material 410 includes an inner surface and an outer surface, the inner surface substantially conforming in shape to a topography of a skin surface of individual 430 and including a microbe-capture region. Peelable skin-covering material 410 is formed from settable material 420. Settable material 420 is configured for application to a skin surface of individual 430 and undergoes a phase change from a liquid or a gelled phase to a flexible solid phase to from peelable skin covering material 410 in response to an applied stimulus, e.g., air, a thermal stimulus, and/or an electromagnetic stimulus.

Image-capture device 120 includes circuitry to capture at least one image of the inner surface of peelable skin-covering material 410 and to transform the captured at least one image into a digital output including information associated with at least one property and a spatial distribution of at least one type of microbe bound to the microbe-capture region. In some embodiments, image-capture device 120 captures one or more signals 160 from the inner surface of peelable skin-covering material 410 in response to directed energy 150, one or more signals 160 representative of at least one property of the at least one type of microbe bound to the microbe-capture region of peelable skin-covering material 410. In an aspect, directed energy 150 includes light, acoustic, or electromagnetic energy. In an aspect, directed energy 150 can include an excitation energy, e.g., an energy that induces fluorescence. In an aspect, one or more signals 160 include one or more reflected signals in response to directed energy 150. In an aspect, one or more signals 160 include one or more emitted signals in response to directed energy 150. In an aspect, one or more signals 160 are representative of a ratio of absorbed to reflected directed energy 150.

Computing device 130 includes circuitry configured to receive the digital output from image-capture device 120 including the information associated with the at least one property and the spatial distribution of the at least one type of microbe bound to the microbe-capture region of peelable skin-covering material 410, compare the at least one property of the at least one type of microbe with a database of reference microbe properties, and generate digital profile 440 including the at least one property and the spatial distribution of the at least one type of microbe bound to the microbe-capture region of peelable skin-covering material 410. In an aspect, computing device 130 further includes circuitry to generate a digital alignment 450 of digital profile 440 of the at least one type of microbe captured on the microbe-capture region of peelable skin-covering material 410 with a digital image of a skin surface of individual 430 covered by settable material 420 prior to peeling. Digital alignment 450 can be reported to a user of the system, e.g., individual 420 or another individual, to aide in determining a recommended treatment regimen to maintain or alter the current types and spatial distribution of microbes on the skin surface of the individual.

FIG. 5 illustrates aspects of a peelable skin-covering material. FIG. 5A shows skin surface 510 including at least one first type of microbe 520 and at least one second type of microbe 530. FIG. 5B shows settable material 540 applied to skin surface 510, essentially covering skin surface 510 and associated microbes. FIG. 5C shows applied stimulus 550 used to set settable material 540 to form peelable skin-covering material 560. FIG. 5D shows peelable skin-covering material 560 peeled from skin surface 510 and capturing one or more of the at least one first type of microbe 520 and one or more of the at least one second type of microbe 530 from skin surface 510. FIG. 5F shows peelable skin-covering material 560 including one or more of the at least one first type of microbe 520 and one or more of the at least one second type of microbe 530 ready for analysis by an image-capture device.

FIG. 6 shows a flowchart of a method for generating a digital profile of the microbiota of the skin. The method includes receiving a digital output from an image-capture device, the digital output including information associated with at least one property and a spatial distribution of at least one type of microbe captured on a microbe-capture region on an inner surface of a skin-covering material at block 600; identifying the at least one type of microbe captured on the microbe-capture region by comparing the information associated with the at least one property of the at least one type of microbe with a database of reference microbe properties at block 610; and reporting to a user an identification and spatial profile of the identified at least one microbe captured on the microbe-capture region on the inner surface of the skin-covering material at block 620.

FIG. 7 shows further aspects of a method such as shown in FIG. 6. In an aspect, receiving a digital output from an image-capture device can include receiving the digital output from at least one digital camera as illustrated in block 700. Non-limiting examples of digital cameras have been described above herein. In an aspect, receiving a digital output from an image-capture device can include receiving the digital output from at least one scanning device as shown in block 705. In an aspect, receiving the digital output from at least one scanning device includes receiving the digital output from at least one of an optical scanning device. In an aspect, receiving the digital output from at least one scanning device includes receiving the digital output from at least one of a fluorescence scanning device. In an aspect, receiving the digital output from at least one scanning device includes receiving the digital output from at least one of an acoustic scanning device. In an aspect, receiving the digital output from at least one scanning device includes receiving the digital output from at least one of an electromagnetic scanning device.

The method of FIG. 6 includes identifying the at least one type of microbe captured on the microbe-capture region by comparing the information associated with the at least one property of the at least one type of microbe with a database of reference microbe properties. In an aspect, comparing the information associated with the at least one property includes comparing at least one of an optical property as shown in block 710. In an aspect, comparing the information associated with the at least one property includes comparing at least one of a fluorescence property as shown in block 715. In an aspect, comparing the information associated with the at least one property includes comparing at least one of an infrared spectral property as shown in block 720. In an aspect, comparing the information associated with the at least one property includes comparing at least one of an acoustic property as shown in block 725. In an aspect, comparing the information associated with the at least one property includes comparing at least one of a reflective property as shown in block 730. In an aspect, comparing the information associated with the at least one property includes comparing at least one of a light scattering property as shown in block 735. In an aspect, comparing the information associated with the at least one property includes comparing at least one of an opacity property as shown in block 740. In an aspect, comparing the information associated with the at least one property includes comparing at least one of a size as shown in block 745. In an aspect, comparing the information associated with the at least one property includes comparing at least one of a morphological property as shown in block 750. In an aspect, comparing the information associated with the at least one property includes comparing at least one of a physical property as shown in block 755.

In an aspect, comparing the information associated with the at least one property includes comparing at least one of a metabolic property, e.g., utilization of a carbon source. In an aspect, comparing the information associated with the at least one property includes comparing at least one of a lipid property, e.g., association of one or more lipid types on a surface of at least one type of microbe. In an aspect, comparing the information associated with the at least one property includes comparing at least one of a carbohydrate property, e.g., association and/or binding properties of at least one carbohydrate on a surface of at least one type of microbe. In an aspect, comparing the information associated with the at least one property includes comparing at least one of a protein property, e.g., enzymatic and/or binding property of a protein. In an aspect, comparing the information associated with the at least one property includes comparing at least one of a genomic property.

FIG. 8 shows further aspects of a method such as shown in FIG. 6. In an aspect, the method includes generating a digital alignment of the spatial profile of the identified at least one type of microbe captured on the microbe-capture region on the inner surface of the skin-covering material with a digital image of a skin surface of an individual covered by the microbe-capture region of the skin-covering material, and reporting to the user a personalized microbe profile including the identification and the spatial profile of the identified at least one type of microbe on the skin surface of the individual, as illustrated in block 800.

In an aspect, the method includes providing a visual representation of the personalized microbe profile on a display, as illustrated in block 810. The display can include a display coupled to a computing device, wherein the computing device can take various forms or be part of an object, and can include, but is not limited to, a computer, a laptop computer, a personal electronic device, a dedicated computing device, a limited resource computing device, a wireless communication device, a mobile wireless communication device, an electronic pen, a handheld electronic writing device, a tablet, a digital camera, a scanner, an ultrasound device, an x-ray machine, a non-invasive imaging device, a cell phone, a PDA, an electronic tablet device, a medical apparatus (implantable or otherwise), or any other like device that takes information as an input and gives it back to the end-users. In an aspect, the display is part of a kiosk that includes the image-capture device and the computing device.

In an aspect, the method includes providing a printout of the personalized microbe profile, as illustrated in block 820. For example, the printout of the personalized microbe profile can include a text only description of the identity and spatial profile of the identified at least one type of microbe on the skin surface of the individual. For example, the printout of the personalized microbe profile can include a color-coded diagram illustrating the identity and the spatial profile of the identified at least one type of microbe on the skin surface of the individual. The color-coded information can be overlaid on an image of the skin surface of the individual. For example, the color-coded diagram can be overlaid over an image of the individual's face, illustrating the distribution of one or more types of microbes on the individual's face.

In an aspect, the method includes exporting the personalized microbe profile to a computing device, as illustrated in block 830. For example, the personalized microbe profile may be generated on a first computing device, e.g., a service provider's office, operably coupled to the image-capture device, e.g., in a service provider's office, and subsequently exported to a second computing device, e.g., an individual's home computer, a hand-held device, personal electronic device, or the like. For example, the personalized microbe profile may be generated on a first computer in the individual's residence and subsequently exported, e.g., via the Internet, to a second computer associated with a service provider, e.g., a medical practitioner's office, a pharmacy, or cosmetic counter. For example, the personalized microbe profile may be exported to a computing device associated with a manufacturer, e.g., the manufacturer of the skin-covering material and/or the system including the skin-covering material. For example, the personalized microbe profile may be exported to a computing device associated with an insurance company. For example, the personalized microbe profile may be exported to a computing device associated with a research group. In an aspect, the service provider may provide a recommended treatment regimen in response to receipt of an individual's personalized microbe profile.

In an aspect, the method optionally includes comparing the personalized microbe profile with a reference microbe profile, generating a recommended treatment regimen from the individual based on the comparison, and reporting the recommended treatment regimen to the user, as shown in block 840. In an aspect, the method can include comparing with a reference microbe profile generated for the individual at at least one previous point in time, as shown in block 850. For example, the reference microbe profile may include a microbe profile generated for an individual prior to treatment for a skin condition. For example, the reference microbe profile may include a microbe profile generated when the individual was younger.

In an aspect, the method can include comparing with a reference microbe profile generated for one or more other individuals, as shown in block 860. For example, the reference microbe profile can represent an optimal microbe profile generated by averaging microbe profile information gathered from a number of other individuals. For example, the reference microbe profile can represent an optimal microbe profile generated from one or more other individuals with a complexion preferred by the individual. For example, the reference microbe profile can represent an optimal microbe profile from a celebrity with a complexion or skin properties preferred by the individual.

In an aspect, the method shown in FIG. 6 can optionally include generating a recommended treatment regimen based on the identification and the spatial profile of the at least one type of microbe captured on the microbe-capture region of the skin-covering material, and reporting the recommended treatment regimen to the user, as illustrated in block 870. For example, the method can include generating a recommended treatment regimen that includes an antimicrobial treatment based on the types of microbes present, e.g., antibiotics for bacteria, fungicide for fungus, or antiviral for a virus. For example, the method can include generating a recommended treatment regimen that includes a skin cleaning process, e.g., a type of soap or antiseptic rinse, based on the identity and the distribution of the at least one type of microbe. For example, the method can include generating a recommended treatment regimen that includes probiotics and/or prebiotics to modulate the microbe profile, e.g., to maintain and/or increase beneficial microbes and/or reduce harmful and/or pathogenic microbes. For example, the method can include generating a recommended treatment regimen that includes a certain type of cosmetic product that is compatible with the microbes present, e.g., helps to maintain good microbes but not encourage harmful microbes and can include probiotics and/or prebiotics. Non-limiting examples of treatment recommendations include antimicrobial agents, cleansing products, medicament, probiotics, prebiotics, cosmetic products, procedures (e.g., shaving or not in sensitive areas, applying warm compresses to open pores, use of a pore-opening or cleaning device, abrasion, and the like).

In an aspect, the recommended treatment regimen can be generated based on comparing the identification and the spatial profile of the at least one type of microbe captured from an individual with reference information, wherein the reference information can include identification and/or a spatial profile of at least one type of microbe captured from the same individual in the same location at a previous point in time. The previous point in time can be one or more days, one or more weeks, and/or one or more years previous to a current time point. The previous point in time may represent a point in time before onset of a condition and/or before onset of a treatment. In an aspect, the recommended treatment regimen can be generated based on comparing the identification and the spatial profile of the at least one type of microbe captured from an individual with reference information that includes identification and/or a spatial profile of at least one type of microbe captured from one or more other individuals. For example, the reference information from the one or more other individuals may include an "average" or a "normal" distribution of microbes. For example, the reference information from the one or more other individuals may include an identification and/or spatial distribution of at least one type of microbe on a skin surface of an admired individual, e.g., a celebrity with healthy skin. In an aspect, the method can include alerting the individual as to whether the identity and the spatial distribution of the at least one type of microbe warrants discussion with a medical professional. In an aspect, reporting the recommended treatment regimen to the user includes reporting the recommended treatment regimen via a display, a printout, or exportation of data to another device, e.g., a personal handheld device.

Figure 9:
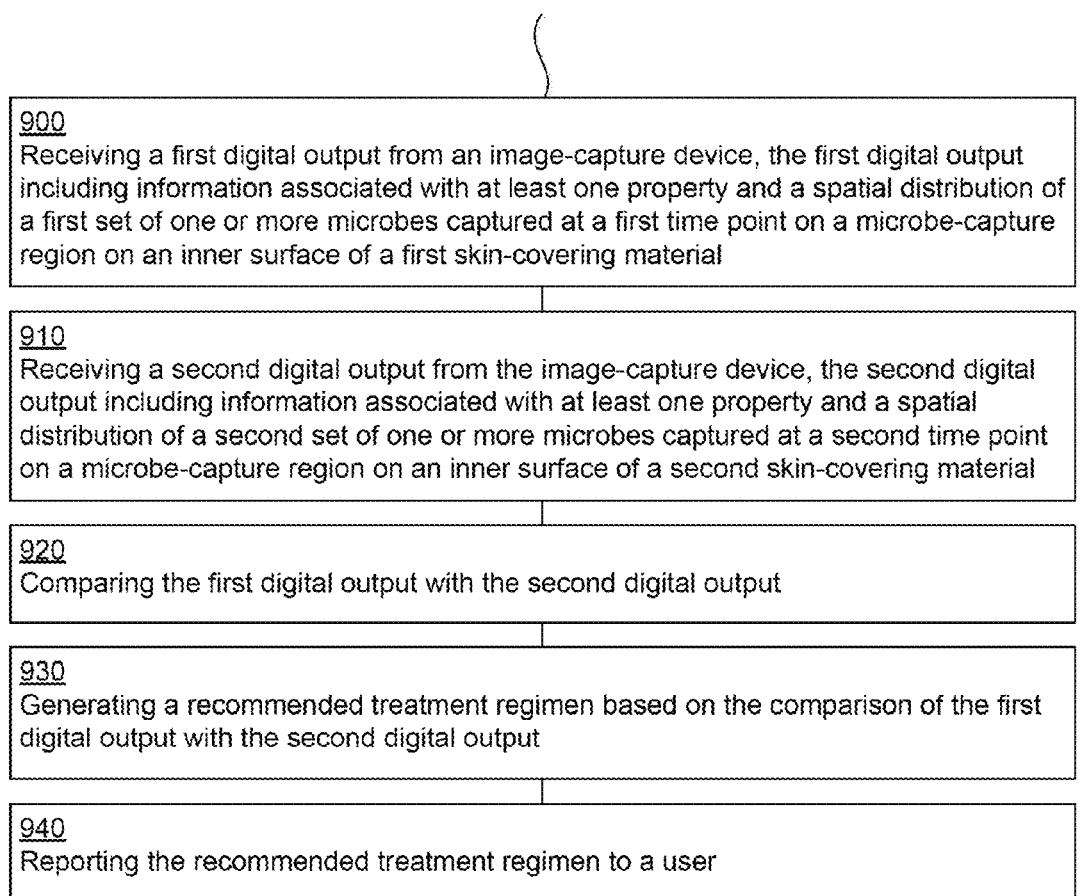
FIG. 9 is a flowchart of a method for assessing microbiota of skin.

FIG. 9 illustrates aspects of a method for assessing microbiota of skin. The method includes receiving a first digital output from an image-capture device at block 900, the first digital output including information associated with at least one property and a spatial distribution of a first set of one or more microbes captured at a first time point on a microbe-capture region on an inner surface of a first skin-covering material; receiving a second digital output from an image capture device at block 910, the second digital output including information associated with at least one property and a spatial distribution of a second set of one or more microbes captured at a second time point on a microbe-capture region on an inner surface of a second skin-covering material; comparing the first digital output with the second digital output at block 920; generating a recommended treatment regimen based on the comparison of the first digital output with the second digital output at block 930; and reporting the recommended treatment regimen to a user at block 940.

In an aspect, the first time point is at a first age of an individual and the second time point is at a second age of an individual. For example, the first time point and the second time point may be separated by days, months, or years depending upon how frequently the skin microbiota of an individual is assessed or monitored. In an aspect, the first time point is at a time before therapeutic treatment and the second time point is at a time after therapeutic treatment. In an aspect, the first time point is at a time point before a pathological condition, e.g., a normal baseline, and the second time point is at a time point after a pathological condition has arisen. In an aspect, a comparison of the microbiota at a first time point versus a second time point is used to generate a recommended treatment regimen, e.g., a cleansing protocol, preferred cosmetics, moisturizers, or antimicrobial treatment.

FIG. 10 illustrates aspects of a method for identifying and generating a spatial profile of microbiota of skin. The method includes applying a skin-covering material to a skin surface of an individual at block 1000, the skin-covering material including at inner surface and an outer surface, the inner surface substantially conforming in shape to a topography of the skin surface of the individual and including a microbe-capture region; removing the skin-covering material from the skin surface of the individual at block 1010; capturing at least one image of the inner surface of the skin-covering material with an image-capture device and transforming the captured at least one image into a digital output, the digital output including information associated with at least one property and a spatial distribution of at least one type of microbe bound to the microbe-capture region 1020; receiving the digital output from the image-capture device at block 1030, the digital output including information associated with at least one property and a spatial distribution of the at least one type of microbe bound to the microbe-capture region; identifying the at least one type of microbe bound to the microbe-capture region by comparing the information associated with the at least one property of the at least one type of microbe with a database of reference microbe properties at block 1040; and reporting to a user an identification and spatial profile of the identified at least one microbe bound to the microbe-capture region on the inner surface of the skin-covering material at block 1050.

In an aspect, the method of FIG. 10 includes applying a pre-formed skin-covering material to the skin surface of the individual. In an aspect, the method of FIG. 10 includes applying a settable material to the skin surface of the individual, the settable material configured to undergo a phase change from a liquid or gelled phase to a flexible solid phase to form a peelable skin-covering material in response to an applied stimulus.

In an aspect, applying the skin-covering material to the skin surface of the individual includes applying the skin-covering material to the skin surface of the individual for a prescribed period of time. For example, the skin-covering material can be placed in uniform contact with the skin surface and immediately removed, e.g., about 1-10 seconds. For example, the skin-covering material can be placed in uniform contact with the skin surface and allowed to sit on the skin surface for about 10 seconds to about 60 minutes.

In an aspect, applying the skin-covering material to the skin surface of the individual includes applying the skin-covering material to the skin surface of the individual under pressure. For example, pressure may be applied manually using hands to press the skin-covering material onto the skin surface of the individual. For example, pressure may be applied by using a tool that allows for uniform pressing of the skin-covering material onto the skin surface of the individual.

In an aspect, applying the skin-covering material to the skin surface of the individual includes applying the skin-covering material to the skin surface of the individual in the presence of a vacuum. For example, the skin-covering material may be fixed to the skin, e.g., with an adhesive, and gentle vacuum used to suck microbes from the skin surface and onto the inner surface of the skin-covering material.

In an aspect, applying the skin-covering material to the skin surface of the individual includes applying the skin-covering material to the skin surface of the individual in the presence of a stimulus. In an aspect, the stimulus includes a thermal or chemical stimulus. For example, the skin surface and/or the skin-covering material may be warmed to facilitate access to microbes on the skin surface, e.g., by opening skin pores. For example, the skin surface and/or the skin-covering material may include a detergent, surfactant, or other agent to aid in removing whole microbes or parts thereof, e.g., proteins, DNA, or RNA, from the skin surface.

FIG. 11 illustrates further aspects of a method such as shown in FIG. 10. In an aspect, the method includes applying a microbe-capture material to the inner surface of the skin-covering material prior to applying the skin-covering material to the skin surface of the individual, as shown in block 1100. For example, the method can include applying an adhesive or gel to the inner surface of the skin-covering material prior to applying to the skin surface, the adhesive or gel capable of capturing at least one type of microbe from the skin surface. In an aspect, the method includes applying a microbe-capture material to the skin surface of the individual prior to applying the skin-covering material to the skin surface of the individual. The microbe-capture material can be sprayed, layered, and/or spread onto the inner surface of the skin-covering material.

In an aspect, the method includes applying at least one signal-generating agent to the skin-covering material, capturing at least one image of the inner surface of the skin-covering material with the image-capture device to detect one or more signals emitted or reflected from the at least one signal-generating agent bound to one or more of the at least one type of microbe bound to the microbe-capture region, and transforming the one or more signals into a digital output, as illustrated in block 1110. For example, a signal-generating agent such as, for example, a fluorescently labeled antibody or aptamer, may be applied to the inner surface of the skin-covering material after the skin-covering material has been removed from the skin surface of the individual. The labeled antibody or aptamer can be configured to bind one or more types of microbes. Excess labeled antibody or aptamer can be removed from the skin-covering material with a rinsing solution prior to capturing an image of the inner surface of the skin-covering material.

In an aspect, the method includes separating the skin-covering material into one or more pieces along one or more tearable lines of perforation, and capturing at least one image with the image-capture device of the inner surface of at least one of the one or more pieces of the skin-covering material, as shown in block 1120. In an aspect, the skin-covering material can be manufactured with perforations. For example, the skin-covering material may be manufactured using a three-dimensional printing process in which the digital template for the skin-covering material includes perforations. In an aspect, the perforations are added to the skin-covering material after manufacture. For example, a skin-covering material manufactured from a thin sheet of material, e.g., latex or paper may be modified with a device configured to punch holes through the skin-covering material. In general, the tearable lines of perforation allow the skin-covering material to be separated into pieces that can be accommodated by the imaging window or scanning surface of the image-capture device.

In an aspect, the method includes generating a digital alignment of the spatial profile of the identified at least one type of microbe bound to the microbe-capture region on the inner surface of the skin-covering material with a digital image of the skin surface of the individual covered by the inner surface of the skin-covering material, and reporting to the user a personalized microbe profile including the identification and the spatial profile of the identified at least one type of microbe on the skin surface of the individual, as shown in block 1130. For example, a digital image of the individual can be captured either before or during placement of the skin-covering material onto the skin surface. In an aspect, the digital image of the skin-surface of the individual can be used to design a personalized skin-covering material as described above herein. One or more registration marks on the skin-covering material can be used to align with one or more landmarks, e.g., moles, blood vessels, or other landmarks on the skin surface that are visible in the digital image. In an aspect, the one or more registration marks are incorporated into the manufacture of the skin-covering material. In an aspect, the one or more registration marks can be added, e.g., with a pen or other marking device, while the skin-covering material is on the skin-surface of the individual.

In an aspect, the method includes generating a recommended treatment regimen based on the identification and the spatial profile of the at least one type of microbe bound to the microbe-capture region on the inner surface of the skin-covering material, and reporting the recommended treatment regimen to the user, as shown in block 1140. For example, the method may include recommending a specific antibiotic and/or antifungal regimen based on the identification and spatial profile of the identified type of microbe. For example, the method may include recommending a skin-cleansing regimen based on the identification and spatial profile of the identified type of microbe. For example, the method may include recommending a probiotic regimen based on the identification and spatial profile of the identified type of microbe. Non-limiting components of a recommended treatment regimen have been described above herein.

FIG. 12 illustrates a system for assessing the microbiota of skin. System 1200 includes skin-covering material 1210, image-capture device 120, and computing device 130. System 1200 further includes at least one signal-generating agent 1280. Signal-generating agent 1280 associates with at least one type of microbe captured on the microbe-capture region on the inner surface of skin-covering material 1210, one or more signals emitted by signal-generating agent 1280 measurable by image-capture device 120. In an aspect, signal-generating agent 1280 can include an ink, stain, or dye that emits or reflects ultraviolet, visible, near infrared, or infrared electromagnetic energy. In an aspect, signal-generating agent 1280 can include one or more histological stain, non-limiting examples of which include crystal violet, safranin, fuschin, methylene blue, or Giemsa stain. In an aspect, signal-generating agent 1280 can include a differential stain, e.g., a Gram's stain, which uses crystal violet with the mordant Gram's iodine and a counterstain, or an acid-fast stain. In an aspect, signal-generating agent 1280 can include a non-selective vital dye, e.g., a redox stain, e.g., 5-cyano-2,3-ditolyl tetrazoliumchloride (CTC). In an aspect, signal-generating agent 1280 includes a vital dye that intercalates into nucleic acids of microbes, non-limiting examples of which include DAPI (4',6-diamidino-2-phenylindole), acridine orange, or Hoechst stain. Other non-limiting examples of vital dyes include calcein AM, carboxyfluorescein diacetate, DiOC (3,3'-dihexyloxacarbocyanine iodide), rhodamine 123, and Nile red. In an aspect, signal-generating agent 1280 can include a stain that will react with a polysaccharide, non-limiting examples of which include Schiff's reagent or a diamino stilbene, e.g., Calcofluor (from, e.g., Polysciences, Inc., Warrington, Pa.). In an aspect, the signal-generating element can include a negative stain, e.g., India ink or nigrosin, which stains the area surrounding the captured microbes, but not the microbes. In an aspect, signal-generating agent 1280 can include a dye-labeled antibody, aptamer, or binding agent that recognizes at least one type of microbe captured on the microbe-capture region. For example, the dye-labeled antibody, aptamer, or other binding agent can bind to one or more biomolecule exposed on the outer surface of a microbe, e.g., a protein, carbohydrate or lipid biomolecule exposed on the outer surface of the microbe. The label associated with the antibody, aptamer, or other binding agent can include a fluorescent label, a colored label, or a chemiluminescent label. For example, the labeled antibody, aptamer, or other binding agent configured to bind the at least one type of microbe may further include fluorescein for direct fluorescence detection or horseradish peroxidase (HRP) for indirect detection using colorimetric or chemiluminesence following addition of peroxidase substrate. In some embodiments, the labeled antibody, aptamer, or other binding agent configured to bind the at least one type of microbe may further include biotin conjugates available for binding with avidin or streptavidin. In an aspect, signal-generating agent 1280 includes at least one fluorescence-generating agent. In an aspect, signal-generating agent 1280 includes at least one chemiluminescence-generating agent. In an aspect, signal-generating agent 1280 includes an anti-16S RNA labeled with a chromophore or fluorophore. In an aspect, signal generating agent 1280 includes universal primers of the type used for amplification of microbial 16S gene sequencing the 1.4 kb amplicon and comparing with known sequences in a database. See, e.g., references regarding Ribosomal Database Project (Cole et al. (2009) *Nucl. Acids Res.* 37(D1):D141-D145); SILVA (Quast et al. (2013) *Nucl. Acids Res.* 41(D1): D590-D596); CORE ("core human oral microbiome;" Griffen et al. (2011), *PLoS ONE* 6(4):e19051), which are incorporated herein by reference. Other non-limiting examples of signal-generating agents include radioactive agents, magnetic agents, radiofrequency identification tags, or contrast agents. Signal-generating agent 1280 can further include labeled oligonucleotides, lectins, proteins, lipids, carbohydrates, ligands, or any other molecule capable carrying a label and interacting with one or more components of the at least one type of microbe captured on the inner surface of skin-covering material 1210. Other non-limiting examples of signal-generating agents include labeled antibodies, aptamers, oligonucleotides, anti-16S rRNAs, antibody fragments, peptides, protein nucleic acids, proteins, viruses, lipids, phospholipids, carbohydrates, enzymes, receptors, lectin, peptide aptamer, bacteria, cells, cell fragments, inorganic molecules, organic molecules, synthetic ligands, artificial binding substrates, mimetic binding elements (e.g., formed by molecular imprinting), or combinations thereof. In an aspect, the binding component of the signal-generating agent can be configured to recognize components of microbe surface biomolecules including amino acid sequences and oligosaccharides.

In an aspect, the signal-generating element is incorporated into the inner surface of the skin-covering material. In an aspect, the signal-generating element can include a responsive material attached to the inner surface of the skin-covering material. For example, the inner surface of the skin-covering material can include a polymer which changes color in response to binding a target, e.g., bacteria. See, e.g., WO2008/059274, which is incorporated herein by reference. In an aspect, the inner surface of the skin-covering material can include a negative chromogen which loses color in response to binding a microbe.

Non-limiting examples of signal-generating agents include optical signal-generating agents, fluorescence signal-generating agents, electrical signal-generating agents, radio signal-generating agents, electromagnetic signal-generating agents, acoustic signal-generating agents, or magnetic signal-generating agents. Non-limiting examples of signal-generating agents include, but are not limited to, at least one of a fluorescent agent, an electromagnetic-emitting agent, a quantum dot, a gold label, dye, or chemiluminescent dye, or a combination thereof. Non-limiting examples of additional signal-generating agents include at least one of a radioactive agent; a radiopaque dye; a radiofrequency identification tag; chromogenic agent; a contrast agent, a visible dye, volatile label; mass label; luminescent label, e.g., bioluminescent or chemiluminescent; metallic label, e.g., gold particles, magnetic beads, or paramagnetic beads; dyes, e.g., direct, indirect, or releasable; or a combination thereof.

In an aspect, the at least one type of signal-generating element is an optical signal-generating agent. In an aspect, the optical signal-generating agent can be a chemical entity that changes color in response to binding a microbe. In an aspect, the optical signal-generating agent can change color in response to metabolism of a microbe bound to the inner surface of the skin-covering material. For example, the optical signal-generating agent can by linked to metabolism of certain classes of biochemicals including sugars, hexophosphates, amino acids, hexose sugars, carboxylic acids, esters, and fatty acids. For example, tetrazolium salts form violet colored formazans in response to microbe metabolism. See, e.g., Tachon et al. (2009) *Microbiology* 155:2941-2948, which is incorporated herein by reference.

In an aspect, the signal-generating agent can include a chromogenic, fluorogenic, or luminescent substrate. Chromogenic substrates can include peptides that react with microbe-derived proteolytic enzymes under the formation of color. For example, the chromogenic substrate may include a chemical group which when released after enzyme cleavage gives rise to color. The color change can be followed spectrophotometrically and may be proportional to the proteolytic activity. For example, the fluorogenic substrate may include a chemical group including a fluorophore, which, when released after enzymatic cleavage or chemical reaction, is fluorescent. For example, a chemiluminescent substrate may include a chemical group which when released after enzyme cleavage or chemical reaction produces light.

In an aspect, the at least one type of signal-generating agent is a fluorescence signal-generating agent. In an aspect, fluorescence signal-emitting agents can include chemical dyes that emit light, i.e., fluoresce, at various wavelengths in response to an excitation energy. In an aspect, the fluorescence signal-generating element can include a quantum dot or semiconductor nanocrystals that fluoresce at various wavelengths in response to an excitation energy. See, e.g., Jaiswal et al. (2003) *Nature Biotech.* 21:47-51, which is incorporated herein by reference. Non-limiting examples of fluorescing dyes include fluorescein (FITC), indocyanine green (ICG) and rhodamine B, red and near infrared emitting fluorophores (600-1200 nm) including cyanine dyes such as Cy5, Cy5.5, and Cy7 (Amersham Biosciences, Piscataway, N.J., USA) and/or a variety of Alexa Fluor dyes such as Alexa Fluor 633, Alexa Fluor 635, Alexa Fluor 647, Alexa Fluor 660, Alexa Fluor 680, Alexa Fluor 700 and Alexa Fluor 750 (Molecular Probes-Invitrogen, Carlsbad, Calif., USA). Additional fluorophores include IRDye800, IRDye700, and IRDye680 (LI-COR, Lincoln, Nebr., USA), NIR-1 and 1C5-OSu (Dejindo, Kumamotot, Japan), LaJolla Blue (Diatron, Miami, Fla., USA), FAR-Blue, FAR-Green One, and FAR-Green Two (Innosense, Giacosa, Italy), ADS 790-NS and ADS 821-NS (American Dye Source, Montreal, Calif.), NIAD-4 (ICx Technologies, Arlington, Va.). Other fluorescing dyes include BODIPY-FL, europium, green, yellow and red fluorescent proteins, luciferase.

In an aspect, the signal-generating agent can include a magnetic marker, e.g., magnetic beads, magnetic particles or carbon nanotubes. Magnetic beads and magnetic particles of various sub-millimeter size are available from commercial sources (e.g., from Seradyn-Thermo Scientific, Indianapolis, Ind.; Dynal-Invitrogen, Carlsbad, Calif.). Carbon nanotubes with various functionalities can be synthesized de novo (see, e.g., Didenko & Baskin (2006) BioTechniques 40:295-302, which is incorporated herein by reference) or may be available from commercial sources (e.g., from Nanolab, Newton, Mass.; Swan Chemical Inc., Lyndhurst, N.J.).

In an aspect, the signal-generating agent can include a radiofrequency identification (RFID) tag, sub-millimeter versions of which have been described. See, e.g., Hornyak *Scientific American Magazine*, pp 68-71, February 2008, which is incorporated herein by reference. Alternatively, the signal-generating agent can include one or more bokodes, millimeter sized visual tags that can be captured with a camera. See, e.g., Mohan et al. *ACM Transactions on Graphics* Proceedings of SIGGRAPH 2009, *Aug.* 3-7, 2009, New Orleans, which is incorporated herein by reference.

In an aspect, the signal-generating element includes paramagnetic and supramagnetic agents with one or more unpaired electrons, e.g., manganese, iron, or gadolinium, for use in magnetic imaging.

FIG. 12A shows a cross-section through skin-covering material 1210 including inner surface 1220 and outer surface 1230. Inner surface 1220 further includes microbe-capture region 1240. Skin-covering material 1210, either a preformed skin-covering material or a peelable skin-covering material, substantially conforms in shape to a topography of a skin surface 1250. Skin surface 1250 includes at least one first type of microbe 1260 and at least one second type of microbe 1270. FIG. 12B shows inner surface 1220 of skin-covering material 1210 in contact with skin-surface 1250. FIG. 12C shows at least one first type of microbe 1260 and at least one second type of microbe 1270 bound to microbe-capture region 1240 on inner surface 1220 of skin-covering material 1210 and skin-covering material 1210 exposed to signal-generating agent 1280. FIG. 12D illustrates a cross-section through skin-covering material 1210 with signal-generating agent 1280 selectively bound to at least one second type of microbe 1270 bound to microbe-capture region 1240 on inner surface 1220. Signal-generating agent 1280 is not bound to at least one first type of microbe 1260. Image-capture device 120 includes circuitry to capture at least one image, e.g., one or more signals 1290, of inner surface 1220 of skin-covering material 1210 and to transform the captured at least one image into a digital output including information associated with at least one property and a spatial distribution of at least one first type of microbe bound to inner surface 1220 of skin-covering material 1210. The at least one property can include one or more signals 1290 emitted or reflected from signal-generating agent 1280 in response to directed energy 1295 from image-capture device 120.

FIG. 13 illustrates aspects of an article of manufacture. Article of manufacture 1300 includes non-transitory machine readable media bearing one or more instructions for assessing microbiota of skin in block 1310. The non-transitory machine readable media stores instructions and/or data for use in assessing microbiota of skin. In an aspect, non-transitory machine readable media 1310 can be computer readable media. In an aspect, non-transitory machine readable media 1310 can be recordable-type media. Computer readable media may also be recordable-type media, and the qualities of being "computer readable" and "recordable-type" should not be construed as being mutually exclusive, though in some cases a computer readable media may not be a recordable-type media, and vice versa. Machine readable media include volatile and nonvolatile, removable and non-removable media implemented in any method or technology for storage of information such as machine readable instructions, data structures, program modules, or other data. Non-transitory machine readable media include, but are not limited to, random-access memory (RAM), read-only memory (ROM), electrically erasable programmable read-only memory (EEPROM), flash memory, or other memory technology, CD-ROM, digital versatile disks (DVD), or other optical disk storage, magnetic cassettes, magnetic tape, magnetic disk storage, or other magnetic storage devices, or any other media which can be used to store the desired information. In a further embodiment, computer storage media may include a group of computer storage media devices. In an aspect, machine readable media may include an information store. In an aspect, an information store may include a quantum memory, a photonic quantum memory, or atomic quantum memory. Combinations of any of the above may also be included within the scope of non-transitory machine readable media.

Non-transitory machine readable media bearing one or more instructions for assessing microbiota of skin, as shown in block 1310, includes one or more instructions for receiving a digital output from an image-capture device, the digital output including information associated with at least one property and a spatial distribution of at least one type of microbe captured on a microbe-capture region on an inner surface of a skin-covering material in block 1320; one or more instructions for comparing the information associated with the at least one property of the at least one type of microbe captured on the microbe-capture region with a database of reference microbe properties in block 1330; one or more instructions for generating a microbe profile including the at least one property and the spatial distribution of the at least one type of microbe captured on the microbe-capture region in block 1340; one or more instructions for generating recommended treatment regimen for an individual based on a comparison of the microbe profile with a reference microbe profile in block 1350; and one or more instructions for reporting to a user at least one of the microbe profile or the recommended treatment regimen in block 1360.

In an aspect, non-transitory machine readable media 1310 can further include one or more instructions for receiving the digital output from at least one digital camera. In an aspect, non-transitory machine readable media 1310 can include one or more instructions for receiving the digital output from at least one scanning device, wherein the scanning device includes at least one of a passive scanning device, an active scanning device, a three-dimensional scanning device, an optical scanning device, a fluorescence scanning device, an acoustic scanning device, or an electromagnetic scanning device.

In an aspect, non-transitory machine readable media 1310 includes one or more instructions for identifying the at least one type of microbe captured on the microbe-capture region by comparing the information associated with the at least one property of the at least one type of microbe with the database of reference microbe properties. In an aspect, non-transitory machine readable media 1310 can further include one or more instructions for identifying the at least one type of microbe captured on the microbe-capture region by comparing at least one of an optical property, autofluorescence property, an infrared spectral property, a reflective property, a light scattering property, an opacity property, a size, a morphological property, or a physical feature with the database of reference microbe properties. In an aspect, the database of reference microbe properties is included in the article of manufacture.

In an aspect, non-transitory machine readable media 1310 includes one or more instructions for generating a digital alignment of the spatial distribution of the identified at least one type of microbe captured on the microbe-capture region on the inner surface of the skin-covering material with a digital image of a skin surface of an individual covered by the microbe-capture region. In an aspect, non-transitory machine readable media 1310 can include one or more instructions for detecting one or more features depicted in the digital images, e.g., the physical landmarks, and match these features with features in the digital spatial profile, e.g., the registration marks. Features and the relationships between them may be detected using any of a number of feature-based methods including, but not limited to, segmentation methods, distance transform, affinely invariant neighborhoods, Harris corner detection, Maximally Stable External Regions, Canny detector, Laplacian of Gaussian, elastic contour extraction, existing edge detection, line intersections, local extrema of wavelet transform, inflection points of curves, and the like. The one or more instructions may further include one or more instructions for matching the features detected in the one or more images of skin surface of the individual with features in the digital spatial profile using one or more feature-matching methods, non-limiting examples of which include Euclidean distance matching, invariant moments, nearest neighbor based matching, correlation-like methods, Fourier methods, mutual information methods, optimization methods. Further non-limiting examples include methods using spatial relations, e.g., graph matching algorithms, methods using invariant descriptors, and relaxation methods. The following references are incorporated by reference and include descriptions of computational methods for image registration: Szeliski *Foundations and Trends in Computer Graphics and Vision*, Vol. 2, No. 1 (2006) 1-104, Zitova & Flusser *Image Vision Computing* (2003) 21:977-1000.

In an aspect, non-transitory machine readable media 1310 includes one or more instructions for generating a personalized microbe profile from the digital alignment, the personalized microbe profile including at least one of an identify of the at least one type of microbe, the spatial distribution of the at least one type of microbe on the skin surface of the individual, or the recommended treatment regimen; and one or more instructions for reporting the personalized microbe profile to the user. In an aspect, non-transitory machine readable media 1310 includes one or more instructions for reporting at least one of the personalized microbe profile or the recommended treatment regimen to a user that is a service provider, e.g., a medical practitioner or other provider who is performing the microbiota assessment. In an aspect, non-transitory machine readable media 1310 includes one or more instructions providing a visual representation of the personalized microbe profile and/or the recommended treatment regimen to a user on a display. In an aspect, non-transitory machine readable media 1310 includes one or more instructions for providing a printout to the user of the personalized microbe profile and/or the recommended treatment regimen. In an aspect, non-transitory machine readable media 1310 includes one or more instructions for exporting the personalized microbe profile and/or the recommended treatment regimen to a computing device, e.g., a second computing device.

In an aspect, non-transitory machine readable media 1310 includes one or more instructions for generating a recommended treatment regimen based on comparing microbiota of a skin surface of an individual at two or more points in time, the one or more instructions including one or more instructions for receiving a first digital output from an image-capture device, the first digital output including information associated with at least one property and a spatial distribution of a first set of one or more microbes captured at a first time point on a microbe-capture region on an inner surface of a first skin-covering material; one or more instructions for receiving a second digital output from an image capture device, the second digital output including information associated with at least one property and a spatial distribution of a second set of one or more microbes captured at a second time point on a microbe-capture region on an inner surface of a second skin-covering material; one or more instructions for comparing the first digital output with the second digital; one or more instructions for generating a recommended treatment regimen based on the comparison of the first digital output with the second digital output; and one or more instructions for reporting the recommended treatment regimen to a user.

In an aspect, non-transitory machine readable media 1310 includes one or more instructions for comparing the personalized microbe profile with a reference microbe profile generated for the individual at a previous point in time, e.g., at a young age, before the onset of a skin disorder, or before and/or after a treatment regimen to treat a skin disorder. In an aspect, non-transitory machine readable media 1310 includes one or more instructions for comparing the personalized microbe profile with a reference microbe profile generating for one or more other individuals, e.g., an average "normal" profile or the profile of an individual with a desirable microbe profile as exemplified by "healthy" looking skin.

Figure 14:
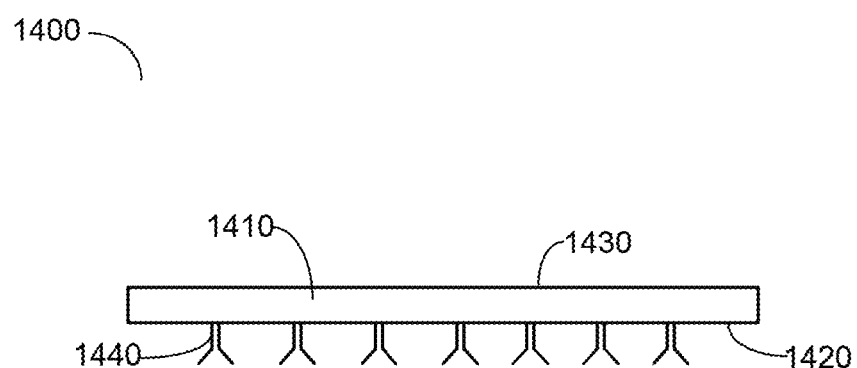
FIG. 14 illustrates a cross-section through a skin-covering material including a plurality of specific microbe-binding elements.

FIG. 14 illustrates aspects of a device for assessing the microbiota of the skin. FIG. 14 shows a cross-section through device 1400 including skin-covering material 1410. Skin-covering material 1410 includes inner surface 1420 and outer surface 1430. Inner surface 1420 substantially conforms in shape to a topography of a skin surface of an individual Inner surface 1420 further includes a plurality of specific microbe-binding elements 1440. Each of the plurality of specific microbe-binding elements 1440 is configured to specifically recognize and/or bind at least one type of microbe.

In an aspect, inner surface 1420 of skin-covering material 1410 is personalized to substantially conform in shape to the topography of the skin surface of the individual. Non-limiting examples of forming a personalized skin-covering material have been described above herein. In an aspect, inner surface 1420 of skin-covering material 1410 substantially conforms in shape to at least a portion of the topography of the skin surface of the individual's face. For example, skin-covering material 1410 including inner surface 1420 can include a mask-like structure that covers all or a portion of the individual's face. In an aspect, the skin-covering material is non-planar, substantially conforming in shape to a topography of a skin surface that is non-planar, e.g., following the contours of the features of a face.

In an aspect, skin-covering material 1410 is reusable. In an aspect, the binding capacity of the plurality of specific microbe-binding elements 1440 can be regenerated. For example, a change in pH, ionic strength, temperature, or combinations thereof may be used to non-destructively remove microbes bound to the at least one type of specific microbe-binding element. In an aspect, the plurality of specific microbe-binding elements 1440 are included in a renewable layer on the inner surface of skin-covering material 1410. For example, the plurality of specific microbe-binding elements 1440 may be applied to the inner surface of a skin-covering material as a liquid, gel, or spray, rinsed off the skin-covering material after a first use, and reapplied for subsequent uses. In this way, a single skin-covering material can be prepared for an individual and used multiple times with regenerated or replaced specific microbe-binding elements.

In an aspect, skin-covering material 1410 includes a pre-formed skin-covering material including a plurality of specific microbe-binding elements. In an aspect, the pre-formed skin-covering material including a plurality of specific microbe-binding elements is personalized to substantially conform in shape to the topography of the skin surface of the individual. In an aspect, the pre-formed skin-covering material including a plurality of specific microbe-binding element includes a semi-rigid pre-formed skin-covering material. In an aspect, the pre-formed skin-covering material including a plurality of specific microbe-binding elements includes a rigid pre-formed skin-covering material. In an aspect, the pre-formed skin-covering material including a plurality of specific microbe-binding elements includes one or more materials shaped by a three-dimensional printer. In an aspect, the pre-formed skin-covering material including a plurality of specific microbe-binding elements includes at least one of acrylic, nylon, plastic, ceramic, resin, rubber, epoxy, thermoplastic, polymer, photopolymer, polyurethane, gel, hydrogel, latex, or silicone. Non-limiting examples of materials and methods for generating a pre-formed skin-covering material have been described above herein.

In an aspect, skin-covering material 1410 including a plurality of specific microbe-binding elements includes a peelable skin-covering material including a plurality of specific microbe-binding elements. In an aspect, the peelable skin-covering material including a plurality of specific microbe-binding elements includes a flexible solid. In an aspect, the peelable skin-covering material including a plurality of specific microbe-binding elements includes a rigid solid. In an aspect, the peelable skin-covering material including a plurality of specific microbe-binding elements includes a settable material. The settable material can include at least one of latex, gel, polymer, plastic, or resin. The settable material includes at least one material configured to undergo a phase change from a liquid phase or a gelled phase to a flexible solid phase in response to an applied stimulus, e.g., air, thermal stimulus, and/or electromagnetic stimulus. Non-limiting examples of materials and methods for generating a peelable skin-covering material have been described above herein.

Specific Microbe-Binding Elements

Skin-covering material 1410 includes a plurality of specific microbe-binding elements 1440. Each of the plurality of specific microbe-binding elements 1440 specifically recognizes at least one type of microbe. The at least one type of microbe can include at least one type of bacteria, fungus, virus, or parasite. In an aspect, each of the plurality of specific microbe-binding elements 1440 recognizes at least one type of mutualistic microbe, commensal microbe, or pathogenic microbe. In an aspect, each of the plurality of specific microbe-binding elements 1440 recognizes at least one type of microbe resident on the skin surface of the individual. Non-limiting examples of microbes including skin-resident microbes have been described above herein.

In an aspect, the specific microbe-binding element is configured to specifically recognize and bind a particular microbe or class of microbes. In an aspect, the specific microbe-binding element may be specific for a particular type of microbe, e.g., bacteria versus fungus. In an aspect, the specific microbe-binding element may be specific for Gram-positive versus Gram-negative bacteria or a particular genus of microbes, e.g., *Propionibacterium* versus *Staphylococcus*. In an aspect, the specific microbe-binding element may be specific for a particular species of bacteria within a genus, e.g., *S. aureus* versus *S. epidermidis*.

Non-limiting examples of specific microbe-binding elements include antibodies, aptamers, oligonucleotides, or anti-16S rRNAs. Other non-limiting examples of specific microbe-binding elements include antibody fragments, peptides, peptide nucleic acids, proteins, viruses, phospholipids, carbohydrates, enzymes, receptors, lectins, peptide aptamers, bacteria, cells, cell fragments, inorganic molecules, organic molecules, artificial binding substrates (e.g., those formed by molecular imprinting), or combinations thereof.

In an aspect, the specific microbe-binding element recognizes one or more components of at least one type of microbe. In an aspect, the specific microbe-binding element recognizes one or more biomolecules associated with the surface of a microbe, e.g., bacteria, a virus, a fungus, or a parasite. In an aspect, the specific microbe-binding element recognizes components of microbe surface biomolecules including amino acid sequences, oligosaccharides, proteoglycans, proteins, peptides, and/or lipids. For example, the specific microbe-binding element can recognize and bind teichoic acids and/or peptidoglycans associated with Gram-positive bacteria. For example, the specific microbe-binding element can recognize and bind common lipopolysaccharide moieties, e.g., 2-keto-3-deoxyoctanate, associated with Gram-negative bacteria. For example, the specific microbe-binding element can recognize and bind chitin associated with fungi. In an aspect, the specific microbe-binding element recognizes nucleic acids. For example, the specific microbe-binding element may be configured to recognize and bind one or more DNA or RNA sequence associated with the at least one type of microbe.

In an aspect, the specific microbe-binding element recognizes one or more biomolecules associated with the bacterial outer membrane, cell wall, and/or cytoplasmic membrane. Non-limiting examples of biomolecules associated with the bacterial outer membrane of Gram-negative bacteria include, but are not limited to, lipopolysaccharide and OMP (outer membrane protein) porins, the latter of which are exemplified by OmpC, OmpF and PhoP of *E. coli*. Non-limiting examples of biomolecules associated with the bacterial cell wall of both Gram-positive and Gram-negative bacterial include, but are not limited to, peptidoglycans, i.e., polymers composed of an alternating sequence of N-acetyl-glucoamine and N-acetyl-muraminic acid and crosslinked by amino acids and amino acid derivatives. Non-limiting examples of biomolecules associated with the bacterial cytoplasmic membrane include, but are not limited to, the MPA1-C (also called polysaccharide copolymerase, PCP2a) family of proteins, the MPA2 family of proteins, and the ABC bacteriocin exporter accessory protein (BEA) family of proteins. Other examples of biomolecules associated with bacteria include, but are not limited to, transporters, e.g., sugar porter (major facilitator superfamily), amino-acid/polyamine/organocation (APC) superfamily, cation diffusion facilitator, resistance-nodulation-division type transporter, SecDF, calcium:cation antiporter, inorganic phosphate transporter, monovalent cation:proton antiporter-1, monovalent cation:proton antiporter-2, potassium transporter, nucleobase:cation symporter-2, formate-nitrite transporter, divalent anion:sodium symporter, ammonium transporter, and multi-antimicrobial extrusion; channels, e.g., major intrinsic protein, chloride channel, and metal ion transporter; and primary active transporters, e.g., P-type ATPase, arsenite-antimonite efflux, Type II secretory pathway (SecY), and sodium-transporting carboxylic acid decarboxylase. A number of other potential biomolecules associated with bacteria have been described in Chung, et al. (2001) *J. Bacteriology* 183:1012-1021, which is incorporated herein by reference.

In an aspect, the specific microbe-binding element recognizes one or more biomolecules associated with at least one type of fungus. Non-limiting examples of biomolecules associated with fungi, e.g., the outer surface of fungi, include chitins and glucans, e.g., alpha glucans (dextran, glycogen, pullulan, starch) and beta glucans (cellulose, curdlan, laminarin, chrysolaninarin, lentinan, lichenin, pleuran, zymosan).

In an aspect, the specific microbe-binding element recognizes one or more biomolecules associated with at least one type of virus. For example, the specific microbe-binding element may be configured to bind one or more capsid proteins of the virus. For example, the specific microbe-binding element may be configured to bind to VP5, a major capsid protein of herpes viruses.

In an aspect, the specific microbe-binding element can include a specific microbe-binding antibody. For example, the specific microbe-binding antibody can include one or more antibodies configured to recognize and bind one or more bacterium, fungus, and/or virus. Antibodies or fragments thereof for use in generating the specific microbe-binding element can include, but are not limited to, monoclonal antibodies, polyclonal antibodies, Fab fragments of monoclonal antibodies, Fab fragments of polyclonal antibodies, F(ab')$_2$ fragments of monoclonal antibodies, F(ab')$_2$ fragments of polyclonal antibodies, chimeric antibodies, non-human antibodies, fully human antibodies, among others. Single chain or multiple chain antigen-recognition sites can be used. Multiple chain antigen recognition sites can be fused or unfused. Antibody fragments can be produced by modification of whole antibodies or synthesized de novo using recombinant DNA technologies. Antibodies or fragments thereof may be generated using standard methods.

Alternatively, an antibody or fragment thereof directed against one or more microbe may be generated, for example, using phage display technology. See, e.g., Kupper et al. (2005) *BMC Biotechnology* 5:4, which is incorporated herein by reference. An antibody a fragment thereof, or an artificial antibody, e.g., Affibody® artificial antibodies (Affibody AB, Bromma, Sweden), can be prepared using in silico design (Knappik et al. (2000) *J. Mol. Biol.* 296:57-86, which is incorporated herein by reference). In some embodiments, antibodies directed against specific microbes may be available from a commercial source (from e.g., Novus Biological, Littleton, Colo.; Sigma-Aldrich, St. Louis, Mo.; United States Biological, Swampscott, Mass.). Non-limiting sources of antibodies designed to bind specific microbes, e.g., specific bacteria, fungi, viruses, or parasites, can be found in Linscott's Directory of Immunological and Biological Reagents (accessible through the website address http://www.linscottsdirectory.com/).

In an aspect, the specific microbe-binding element includes a specific microbe-binding aptamer. The aptamer can be an oligonucleotide RNA- or DNA-based aptamer configured to recognize and bind one or more of a bacteria, fungus, virus, or parasite. Aptamers are artificial oligonucleotides (DNA or RNA) that can bind to a wide variety of entities (e.g., metal ions, small organic molecules, proteins, and cells) with high selectivity, specificity, and affinity. Aptamers may be isolated from a large library of $10^{14}$ to $10^{15}$ random oligonucleotide sequences using an iterative in vitro selection procedure termed "systemic evolution of ligands by exponential enrichment" (SELEX). See, e.g., Cao, et al (2005) *Current Proteomics* 2:31-40; Proske et al. (2005) *Appl. Microbiol. Biotechnol.* 69:367-374, which are incorporated herein by reference. In general, SELEX may be used to generate aptamers against any of a number of microbial targets, including but not limited to bacteria, fungi, viruses, and parasites. See, e.g., Chen et al. (2007) *Biochem. Biophys, Res. Commun.* 357:743-748, Nitsche et al. (2007) *BMC Biotechnol.* 7:48; Gopinath et al. (2012) *J. Virol.* 86:6732-6744; Low et al. (2009) *Biochem. Biophys, Res. Commun.* 386:544-548, which are incorporated herein by reference.

In an aspect, the specific microbe-binding element includes a peptide-based aptamer, an artificial protein in which inserted peptides are expressed as part of the primary sequence of a structurally stable protein and having binding affinities comparable to antibodies. See, e.g., Crawford, et al. (2003) *Brief Funct. Genomic Proteomic* 2:72-79, which is incorporated herein by reference. Peptide aptamers can be generated by screening a target, e.g., all or part of a microbe, against yeast two-hybrid libraries, yeast expression libraries, bacterial expression libraries and/or retroviral libraries.

In an aspect, the specific microbe-binding element includes a novel peptide configured to specifically recognize and bind one or more microbes. Novel peptides that bind specific targets, e.g., a surface component of a bacteria, virus, or fungi, can be generated, for example, using phage display methodologies. See, e.g., Spear, et al. (2001) *Cancer Gene Ther.* 8:506-511, which is incorporated herein by reference. In an aspect, the phage express novel peptides on the surface as fusion proteins in association with a phage major or minor coat protein and can be screened for binding interaction with one or more microbes.

In an aspect, the specific microbe-binding element can include a ligand that specifically recognizes one or more microbes. For example, the specific microbe-binding element can include CD14, which is associated with monocyte/macrophages and known to bind lipopolysaccharide associated with Gram-negative bacteria as well as lipoteichoic acid associated with the Gram-positive bacteria *Bacillus subtilis* (see, e.g., Fan, et al. (1999) *Infect. Immun.* 67: 2964-2968). In an aspect, specific microbe-binding element can include all or part of a pattern recognition receptor that recognizes microbe-specific molecules (e.g., bacterial carbohydrates, bacterial or viral DNA or RNA, bacterial peptides, peptidoglycans, lipoteichoic acids, N-formylmethionine, lipoproteins, and fungal glucans). Non-limiting examples of pattern recognition receptors with microbe-binding properties include toll-like receptors, C-type lectin receptors, NOD-like receptors, RIG-I-like receptors, RNA helicases, complement receptors, collectins, ficolins, pentraxins, C-reactive proteins, lipid transferases, and the like. See, e.g., Modlin (2012) *J. Invest. Dermatol.* 132:882-886; Gauglitz et al. (2012) *Acta Derm. Venereol.* 92:291-298, which are incorporated herein by reference.

In an aspect, the specific microbe-binding element includes plasminogen to bind a fungus, e.g., *Candida albicans*. See, e.g., Crowe et al. (2003) *Mol. Microbiol.* 47:1637-1651, which is incorporated herein by reference.

In an aspect, the specific microbe-binding element includes a lectin. Lectins include carbohydrate-binding proteins that bind cell surface glycoproteins and/or glycolipids. Because of the specificity that each lectin has toward a particular carbohydrate structure, even oligosaccharides with identical sugar compositions can be distinguished or separated. Examples of lectins include, but are not limited to, algal lectins, e.g., b-prism lectin; animal lectins, e.g., tachylectin-2, C-type lectins, C-type lectin-like proteins, calnexin-calreticulin, capsid protein, chitin-binding protein, ficolins, fucolectin, H-type lectins, I-type lectins, sialoadhesin, siglec-5, siglec-7, micronemal protein, P-type lectins, pentrxin, b-trefoil, galectins, congerins, selenocosmia huwena lectin-I, Hcgp-39, Ym1; bacterial lectins, e.g., *Pseudomonas* PA-IL, *Burkholderia* lectins, chromobacterium CV-IIL, *Pseudomonas* PA IIL, Ralsonia RS-ILL, ADP-ribosylating toxin, *Ralstonia* lectin, *Clostridium* hemagglutinin, botulinum toxin, tetanus toxin, cyanobacterial lectins, FimH, GafD, PapG, Staphylococcal enterotoxin B, toxin SSL11, toxin SSL5; fungal and yeast lectins, e.g., *Aleuria aurantia* lectin, integrin-like lectin, *Agaricus* lectin, *Sclerotium* lectin, *Xerocomus* lectin, *Laetiporus* lectin, *Marasmius oreades* agglutinin, agrocybe galectin, coprinus galectin-2, Ig-like lectins, L-type lectins; plant lectins, e.g., alpha-D-mannose-specific plant lectins, amaranthus antimicrobial peptide, hevein, pokeweed lectin, *Urtica dioica* UD, wheat germ WGA-1, WGA-2, WGA-3, artocarpin, artocarpus hirsute AHL, banana lectin, Calsepa, heltuba, jacalin, *Maclura pomifera* MPA, MornigaM, Parkia lectins, abrin-a, abrus agglutinin, amaranthin, castor bean ricin B, ebulin, mistletoe lectin, TKL-1, cyanovirin-N homolog, and various legume lectins; and viral lectins, e.g., capsid protein, coat protein, fiber knob, hemagglutinin, and tailspike protein. See, e.g., E. Bettler, R. Loris, A. Imberty "3D-Lectin database: A web site for images and structural information on lectins" 3rd Electronic Glycoscience Conference, The internet and World Wide Web, 6-17 Oct. 1997; http://www.cermav.cnrs.fr/lectines/, which is incorporated herein by reference.

In an aspect, the specific microbe-binding element includes an artificial binding substrate formed by the process of molecular imprinting. In the process of molecular imprinting, a template, e.g., a microbe or a surface component of a microbe, is combined with functional monomers which, upon cross-linking, form a polymer matrix that surrounds the template. See, e.g., Alexander, et al. (2006) *J. Mol. Recognit.* 19:106-180, which is incorporated herein by reference. Removal of the template leaves a stable cavity in the polymer matrix that is complementary in size and shape to the template. In an aspect, functional monomers of acrylamide and ethylene glycol dimethacrylate can be mixed with at least one type of microbe or parts thereof in the presence of a photoinitiator and ultraviolet irradiation used to cross-link the monomers. The resulting polymer can be crushed or ground into smaller pieces and washed to remove the at least one type of microbe or parts thereof, leaving a particulate matrix material capable of binding the at least one type of microbe. Examples of other functional monomers, cross-linkers and initiators that can be used to generate an artificial binding substrate are provided. See, e.g., U.S. Pat. No. 7,319,038; Alexander, et al. (2006) *J. Mol. Recognit.* 19:106-180, each of which is incorporated herein by reference. In an aspect, hydrogels can be used for molecular imprinting. Other examples of synthetic binders are provided. See, e.g., U.S. Pat. Nos. 6,255,461; and 6,797,522; and Ye and Haupt (2004) *Anal Bioanal Chem.* 378: 1887-1897; Peppas and Huang (2002) *Pharm Res.* 19: 578-587, each of which is incorporated herein by reference.

In an aspect, the specific microbe-binding element recognizes and binds DNA and/or RNA sequences associated with the at least one type of microbe. In this instance, the one or more microbes may first be subjected to a lysis agent, e.g., a detergent, to make the cytoplasmic components of the microbes more accessible. For example, the specific microbe-binding element may be a cDNA element engaged in DNA-DNA hybridization with microbe DNA sequence. In an aspect, the specific microbe-binding element may include oligonucleotides capable of binding to unique 16S small subunit ribosomal (rRNA) genes. In an aspect, various phylogenetic markers may be targeted including ribosomal RNA, elongation and initiation factors, RNA polymerase subunits, DNA gyrases, heat shock proteins, and recA proteins.

In an aspect, the plurality of specific microbe-binding elements includes a plurality of specific microbe-binding elements of a single type. In an aspect, "a single type" refers to a type of specific microbe-binding elements, e.g., an antibody versus an aptamer. In an aspect, "a single type" refers to a specific antibody, e.g., a monoclonal antibody with a specific protein sequence or an aptamer with a specific nucleotide sequence. In an aspect, the plurality of specific microbe-binding elements includes a plurality of specific microbe-binding elements of one or more types. In an aspect, the "one or more types" refers to an antibody versus an aptamer. In an aspect, the "one or more types" refers to one or more distinct antibodies with distinct protein sequences and/or recognition specificities or one or more distinct aptamer with distinct nucleotides sequences and/or recognition specificities.

In an aspect, the plurality of specific microbe-binding elements are incorporated into the skin-covering material. In an aspect, the plurality of specific microbe-binding elements are substantially uniformly distributed throughout the skin-covering material. For example, the plurality of specific microbe-binding elements may be uniformly dispersed in a liquid or gelled form during manufacture of the skin-covering material.

In an aspect, the plurality of specific microbe-binding elements are substantially distributed along the inner surface of the skin-covering material. In an aspect, the plurality of specific microbe-binding elements are functionally attached to the inner surface of the skin-covering material. In an aspect, the plurality of specific microbe-binding elements are covalently attached to the inner surface of the skin-covering material. In an aspect, the plurality of specific microbe-binding elements are non-covalently attached to the inner surface of the skin-covering material.

In an aspect, the plurality of specific microbe-binding elements are covalently attached to at least the inner surface of the skin-covering material using a homobifunctional, heterobifunctional, and/or photoreactive crosslinking reagent. For example, the inner surface of the skin-covering material may include a layer of silane to which is bound one arm of the heterobifunctional crosslinking reagent. The other arm of the heterobifunctional crosslinking reagent is covalently bound at least one type of specific microbe-binding element. See, e.g., U.S. Pat. No. 5,077,210, which is incorporated herein by reference. The plurality of specific microbe-binding elements can be cross-linked to the inner surface of the skin-covering material through amine groups, carbohydrate groups, sulfhydryl groups, or combinations thereof. Non-limiting examples of homobifunctional cross-linking reagents include primary amine/primary amine linkers such as BSOCES ((bis(2-[succinimidooxy-carbonyloxy] ethyl) sulfone), DMS (dimethyl suberimidate), DMP (dimethyl pimelimidate), DMA (dimethyl adipimidate), DSS (disuccinimidyl suberate), DST (disuccinimidyl tartate), Sulfo DST (sulfodisuccinimidyl tartate), DSP (dithio-bis(succinimidyl propionate), DTSSP (3,3'-dithiobis(succinimidyl propionate), EGS (ethylene glycol bis(succinimidyl succinate)) and sulfhydryl/sulfhydryl linkers such as DPDPB (1,4-di-(3'-[2'pyridyldithio]-propionamido) butane). Non-limiting examples of heterobifunctional cross-linking reagents include primary amine/sulfhydryl linkers such as MBS (m-maleimidobenzoyl-N-hydroxysuccinimide ester), Sulfo MBS (m-maleimidobenzoyl-N-hydroxysulfosuccinimide), GMBS (N-gamma-maleimidobutyryl-oxysuccinimide ester), Sulfo GMBS (N-gamma-maleimidobutyryloxysulfosuccinimide ester), EMCS (N-(epsilon-maleimidocaproyloxy) succinimide ester), Sulfo EMCS (N-(epsilon-maleimidocaproyloxy) sulfo succinimide), SIAB (N-succinimidyl(4-iodoacetyl)aminobenzoate), SMCC (succinimidyl 4-(N-maleimidomethyl)cyclohexane-1-carboxylate), SMPB (succinimidyl 4-(rho-maleimidophenyl) butyrate), Sulfo SIAB (N-sulfosuccinimidyl(4-iodoacetyl) aminobenzoate), Sulfo SMCC (sulfosuccinimidyl 4-(N-maleimidomethyl)cyclohexane-1-carboxylate), Sulfo SMPB (sulfosuccinimidyl 4-(rho-maleimidophenyl) butyrate), and MAL-PEG-NHS (maleimide PEG N-hydroxysuccinimide ester); sulfhydryl/hydroxyl linkers such as PMPI (N-rho-maleimidophenyl) isocyanate; sulfhydryl/carbohydrate linkers such as EMCH (N-(epsilon-maleimidocaproic acid) hydrazide); and amine/carboxyl linkers such as EDC (1-ethyl-3-(3-dimethylaminopropyl) carbodiimide hydrochloride).

In an aspect, the plurality of specific microbe-binding elements are non-covalently attached to at least the inner surface of the skin-covering material. Non-limiting examples of non-covalent interactions include hydrogen bonds, ionic bonds, van der Waals forces, and hydrophobic interactions. For example, a specific microbe-binding element that is an oligonucleotide could be non-covalently attached through hybridization to at least the inner surface of a skin-covering material that includes a complementary oligonucleotide sequence. In an aspect, the plurality of specific microbe-binding elements are non-covalently attached to the inner surface of the skin-covering material through protein-protein interactions. For example, a type of specific microbe-binding element that includes biotin could be non-covalently attached to at least the inner surface including streptavidin or avidin. For example, a single chain antibody may incorporate streptavidin as part of a fusion protein to facilitate attachment of the antibody to a solid substrate via a biotin-streptavidin linkage. See, e.g., Koo et al. (1999) *Appl. Environ. Microbiol.* 64:2497-2502, which is incorporated herein by reference. Other non-limiting examples non-covalent interactions include interactions between protein A or protein G and immunoglobulins, ligands with receptors, and secondary antibodies with primary antibodies.

Figure 15:
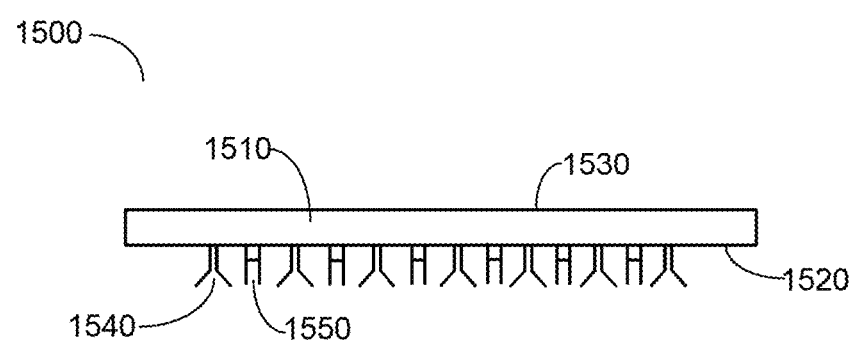
FIG. 15 illustrates a cross-section through a skin-covering material including a plurality of specific microbe-binding elements of a first type and a plurality of a specific microbe-binding elements of a second type.

FIG. 15 illustrates aspects of a device for assessing the microbiota of the skin. FIG. 15 shows a cross-section through device 1500. Skin-covering material 1510 includes inner surface 1520 and outer surface 1530. Inner surface 1520 substantially conforms in shape to a topography of a skin surface of an individual. In an aspect, skin-covering material 1510 includes a pre-formed skin-covering material. In an aspect, skin-covering material 1510 includes a peelable skin-covering material. Inner surface 1520 further includes a plurality of specific microbe-binding elements of a first type 1540 and a plurality of specific microbe-binding elements of a second type 1550. In an aspect, at least one of the plurality of specific microbe-binding elements of the first type 1540 specifically recognizes at least one first type of microbe and at least one of the plurality of specific microbe-binding elements of the second type 1550 specifically recognizes at least one second type of microbe. In an aspect, the plurality of specific microbe-binding elements of the first type 1540 differs from the plurality of specific microbe-binding elements of the second type 1550 and the at least one first type of microbe differs from the at least one second type of microbe. In this manner, two or more types of microbes can be specifically bound to or captured by the skin-covering material. In an aspect, the plurality of specific microbe-binding elements of the first type 1540 differs from the plurality of specific microbe-binding elements of the second type 1550 but the at least one first type of microbe does not differ from the at least one second type of microbe. In general, the inner surface of the skin-covering material can include one or more types of specific microbe-binding elements for specifically interacting with one or more types of microbes.

Figure 16:
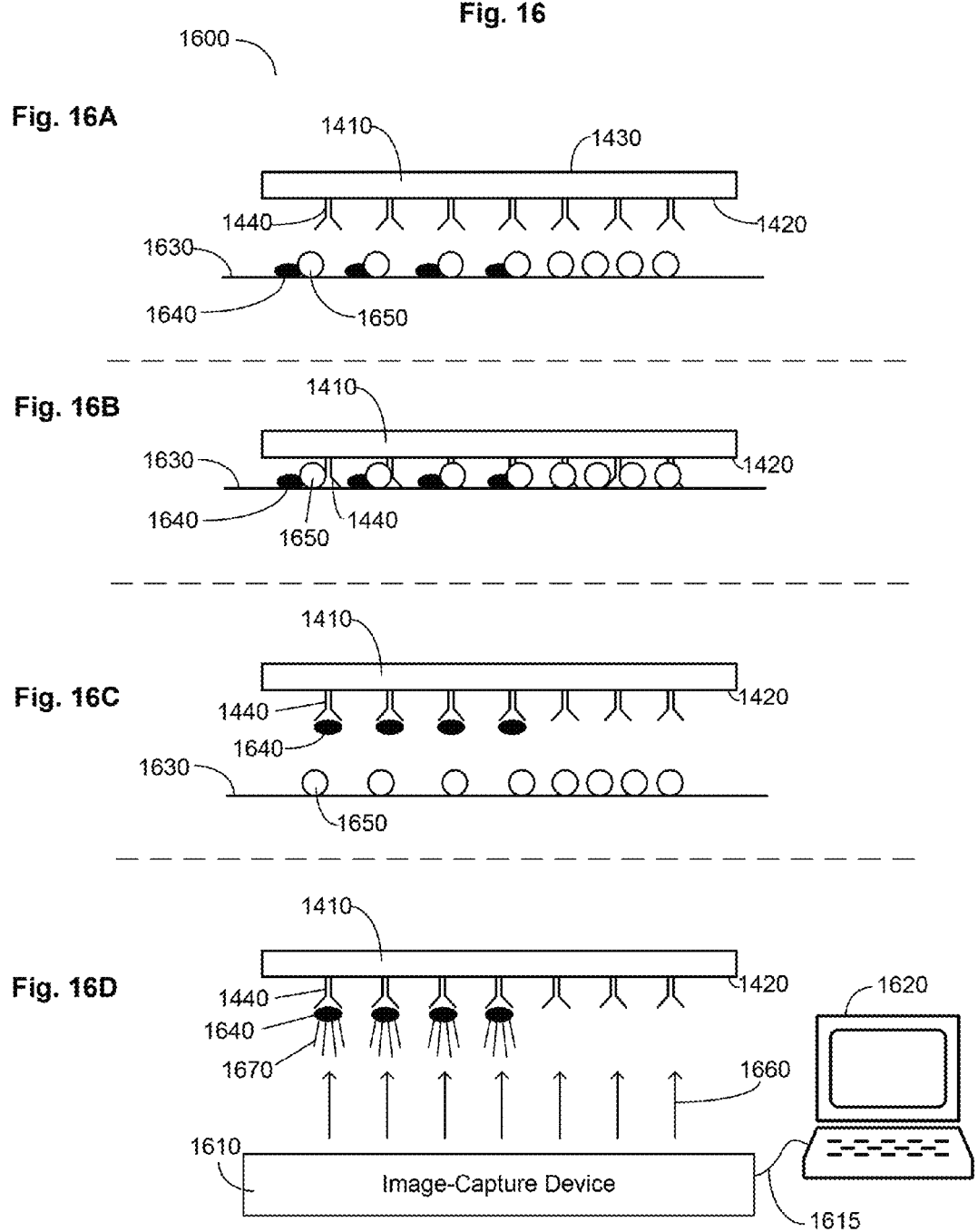
FIGS. 16A-16D illustrate aspects of a system for assessing microbiota of skin.

FIG. 16 illustrates aspects of a system for assessing the microbiota of skin. System 1600 includes skin-covering material 1410, image-capture device 1610, and computing device 1620. FIG. 16A shows a cross-section through skin-covering material 1410. Skin-covering material 1410 includes inner surface 1420 and outer surface 1430, inner surface 1420 substantially conforming in shape to a topography of skin surface 1630 of an individual and including a plurality of specific microbe-binding elements 1440 associated with inner surface 1420. Skin surface 1630 includes at least one first type of microbe 1640 and at least one second type of microbe 1650. FIG. 16B shows a cross-section through skin-covering material 1410 with inner surface 1420 of skin-covering material 1410 including the plurality of specific microbe-binding elements 1440 in close proximity to skin surface 1630 and at least one first type of microbe 1640 and at least one second type of microbe 1650. FIG. 16C shows a cross-section through skin-covering 1410, with at least one first type of microbe 1640 bound to one or more of specific microbe-binding elements 1440 on inner surface 1420 of skin-covering material 1410. The second type of microbe 1650 does not interact with specific microbe-binding element 1440 and remains associated with skin-surface 1630. FIG. 16D shows a cross-section of skin-covering material 1410 imaged with image-capture device 1610. In this instance, image-capture device 1610 includes circuitry to capture at least one image of inner surface 1420 of skin-covering material 1410 and to transform the captured at least one image into a digital output including information associated with at least one property and a spatial distribution of at least one first type of microbe 1640 bound to at least one of the plurality of specific microbe-binding elements 1440. The at least one property can include one or more signal 1670 emitted from the at least one first type of microbe 1640 in response to directed energy 1660 from image-capture device 1610. Image-capture device 1610 can include any of a number of image-capture devices including digital cameras and scanners, non-limiting examples of which have been describe above herein.

In an aspect, image-capture device 1610 includes circuitry configured to capture at least one image of at least one first portion of inner surface 1420 of skin-covering material 1410 and at least one image of at least one second portion of inner surface 1420 of skin-covering material 1410 adjacent to the at least one first portion; and generate a composite image including the at least one image of the at least one first portion of inner surface 1420 of skin-covering material 1410 and the at least one image of the at least one second portion of inner surface 1420 of skin-covering material 1410. In an aspect, image-capture device 1610 further includes a feeding mechanism and an imaging surface to accommodate at least a portion of the entirety of skin-covering material 1410, wherein the feeding mechanism is configured to feed in the at least a portion of skin-covering material 1410 onto the image surface. In an aspect, image-capture device 1610 is a hand-held image-capture device, e.g., a smartphone, camera, or other hand-held scanning device.

Image-capture device 1610 is operably coupled to computing device 1620 through a communication link 1615. Communication link 1615 can include at least one of a wireless communication link, e.g., Bluetooth or other radio transmission link, or a wired communication link, e.g., an electrical link. In an aspect image-capture device 1610 and computing device 1620 including the processor are incorporated into a single unit. In an aspect, image-capture device 1610 and computing device 1620 including the processor are incorporated into an interactive kiosk.

Computing device 1620 includes a processor and circuitry configured to receive the digital output from image-capture device 1610 including information associated with the at least one property and the spatial distribution of the at least one first type of microbe 1640 bound to the at least one of the plurality of specific microbe-binding elements 1440 associated with inner surface 1420 of skin-covering material 1410, compare the at least one property of the at least one first type of microbe 1640 with a database of reference microbe properties, and generate a digital profile including the at least one property and the spatial distribution of the at least one first type of microbe 1640 bound to the at least one of the plurality of specific microbe-binding elements 1440. Non-limiting features of a computing device have been described above herein, for example, in FIG. 2.

In an aspect, computing device 1620 including the processor further includes circuitry to identify the at least one first type of microbe bound to the at least one of the plurality of specific microbe-binding elements based on comparison of the at least one property of the at least one first type of microbe with the database of reference microbe properties. In addition, the digital profile can include the identification of the at least one type of microbe bound to the at least one of the plurality of specific microbe-binding elements based on comparison of the at least one property of the at least one type of microbe with the database of reference microbe properties. Non-limiting examples of reference microbe properties to be included in the database include reference autofluorescence properties, optical properties, infrared properties, reflective properties, light scattering properties, opacity properties, size properties, morphological properties, physical features, metabolic properties, lipid properties, carbohydrate properties, protein properties, and/or genomic properties.

In an aspect, computing device 1620 further includes circuitry to generate a digital alignment of the digital profile of the at least one type of microbe captured on the microbe-capture region of skin-covering material with a digital image of a skin surface of individual covered by the inner surface of the skin-covering material. The digital alignment can be reported to a user of the system, e.g., the individual or a service provider, to aid in determining a recommended treatment regimen to maintain or alter the current types and spatial distribution of microbes on the skin surface of the individual.

In an aspect, computing device 1620 includes circuitry configured to report to a user a personalized microbe profile, the personalized microbe profile including an identity of the at least one type of microbe and a spatial distribution of the identified at least one type of microbe on the skin surface of the individual. In an aspect, the user is the individual upon whom the skin-covering material has been placed. In an aspect, the user includes a service provider, e.g., a medical practitioner, a cosmetologist, or the like. In an aspect, the user includes a third-party payer, e.g., an insurance company. In an aspect, the user includes a distributor, e.g., the manufacturer of one or more components of the system, e.g., the skin-covering material, the image-capture device, and/or the computing device and associated software. In an aspect, computing device 1620 includes circuitry to provide a visual representation of the personalized microbe profile on a display. The display can be operably coupled to computing device 1620 or operably coupled to a second computing device. In an aspect, computing device 1620 includes circuitry to provide a printout to the user, the printout including the personalized microbe profile. In an aspect, computing device 1620 includes circuitry to export information regarding the personalized microbe profile to at least one second computing device.

In an aspect, computing device 1620 includes circuitry configured to generate a treatment recommendation based on an identity of the at least one type of microbe and a spatial distribution of the at least one type of microbe on the skin surface of the individual. The treatment recommendation can include use of an anti-microbial agent, e.g., antibiotic or fungicide, use of a cleaning regimen, e.g., type of soap, abrasive, astringent, and the like, use of a probiotic, e.g., adding back bacteria or other microbes that contribute to a healthy skin condition, and/or change in a diet, e.g., increased fluids, omitting certain foods, and the like.

Figure 17:
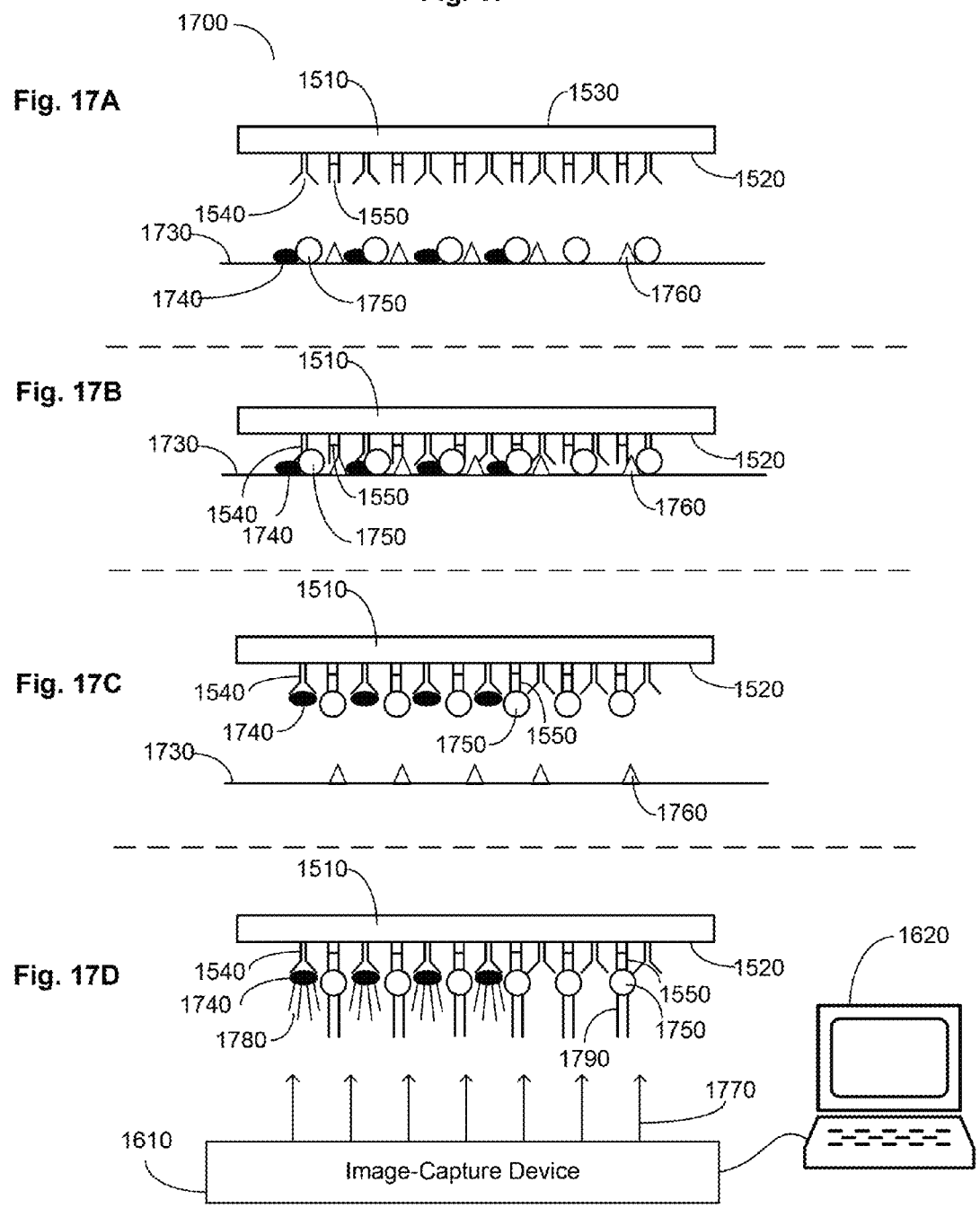
FIGS. 17A-17D illustrate aspects of a system for assessing microbiota of skin.
Figure 18A:
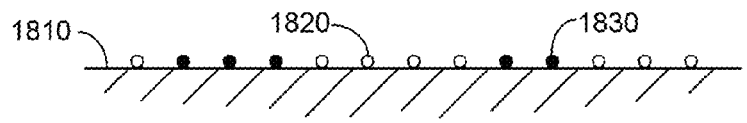
FIGS. 18A-18E illustrate aspects of a peelable skin-covering material.
Figure 18B:
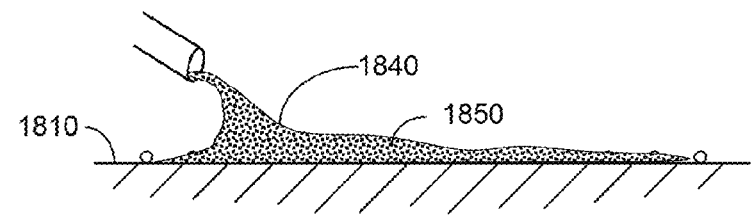
Figure 18C:
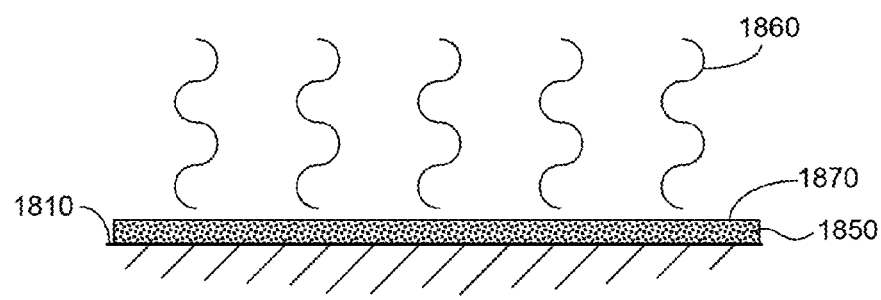
Figure 18D:
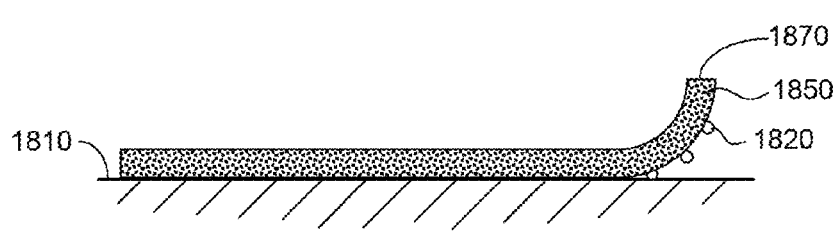
Figure 18E:
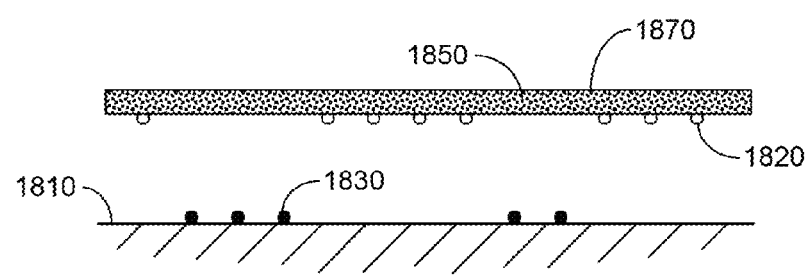

FIG. 17 illustrates aspects of a system for assessing the microbiota of skin. System 1700 includes skin-covering material 1510, image-capture device 1610, and computing device 1620. FIG. 17A shows a cross-section through skin-covering material 1510 in proximity to skin surface 1730. Skin-covering material 1510 includes inner surface 1520 and outer surface 1530. Inner surface 1520 substantially conforms in shape to skin surface 1730 of an individual Inner surface 1520 further includes a plurality of specific microbe-binding elements of a second type 1540 and a plurality of specific microbe-binding elements of a second type 1550. In an aspect, at least one of the plurality of specific microbe-binding elements of the first type 1540 specifically recognizes at least one first type of microbe and at least one of the plurality of specific microbe-binding elements of the second type 1550 specifically recognizes at least one second type of microbe. Skin surface 1730 includes a first type of microbe 1740, a second type of microbe 1750, and a third type of microbe 1760. FIG. 17B illustrates a cross-section of skin-covering material skin-covering material 1510 applied to skin surface 1730, which allows the plurality of specific microbe-binding elements of the first type 1540 and the plurality of specific microbe-binding elements of the second type 1550 on inner surface 1520 to interact with first type of microbe 1740, second type of microbe 1750, and third type of microbe 1760 on skin surface 1730. FIG. 17C illustrates a cross-section of skin-covering material 1510 in which the first type of microbe 1740 is bound to at least one of the plurality of specific microbe-binding elements of the first type 1540 on inner surface 1520 and the second type of microbe 1750 is bound to at least one of the plurality of specific microbe-binding elements of the second type 1550 on inner surface 1520. Third type of microbe 1760 remains on skin surface 1730. FIG. 17D shows a cross-section of inner surface 1520 of skin-covering material 1510 imaged with image-capture device 1610. In this instance, image-capture device 1610 includes circuitry to capture at least one image of inner surface 1520 of skin-covering material 1510 and to transform the captured at least one image into a digital output including information associated with at least one property and a spatial distribution of at least one first type of microbe 1740 bound to at least one of the plurality of specific microbe-binding elements of the first type 1540 and at least one property and a spatial distribution of at least one second type of microbe 1750 bound to at least one of the plurality of specific microbe-binding elements of the second type 1550. The at least one property can include at least one property of one or more signals 1780 emitted or reflected from the at least one first type of microbe 1740 in response to directed energy 1770 from image-capture device 1610 and at least one property of one or more signals 1790 emitted or reflected from the at least one second type of microbe 1750 in response to directed energy 1770 from image-capture device 1610. Image-capture device 1610 can include any of a number of image-capture devices including digital cameras and scanners, non-limiting examples of which have been describe above herein.

Image-capture device 1610 is operably coupled to computing device 1620. Computing device 1620 includes a processor and circuitry configured to receive the digital output from image-capture device 1610 including the information associated with the at least one property and the spatial distribution of the at least one first type of microbe 1740 bound to the at least of the plurality of specific microbe-binding elements of the first type 1540 and the at least one property and the spatial distribution of the at least one second type of microbe 1750 bound to the at least one of the plurality specific microbe-binding elements of the second type of 1550 with a database of reference microbe properties, and generate a digital profile of the first type of microbe 1740 and the second type of microbe 1750 specifically bound to skin-covering material 1510. Non-limiting features of a computing device have been described above herein, for example, in FIG. 2.

FIG. 18 illustrates aspects of a peelable skin-covering material for assessing the microbiota of skin. FIG. 18A shows skin surface 1810 including a plurality of a first type of microbe 1820 and a plurality of a second type of microbe 1830. FIG. 18B shows settable material 1840 including a plurality of specific microbe-binding elements 1850 applied to skin surface 1810. Settable material 1840 includes at least one of latex, gel, polymer, plastic, or resin. Settable material 1840 includes at least one material configured to undergo a phase change from a liquid or gelled phase to a flexible solid phase in response to an applied stimulus. The plurality of specific microbe-binding elements can include a plurality of specific microbe-binding elements of a first type and a plurality of specific microbe-binding elements of a second type, wherein the specific microbe-binding element of the first type recognizes at least one first type of microbe and the specific microbe-binding element of the second type recognizes at least one second type of microbe. FIG. 18C shows applied stimulus 1860 to transform settable material 1840 on skin surface 1810 into peelable skin-covering material 1870 including the plurality of specific microbe-binding elements 1850. Applied stimulus 1860 can include at least one of air, a thermal stimulus, or an electromagnetic stimulus. FIG. 18D shows peelable skin-covering material 1870 including the plurality of at least one type of specific microbe-binding element partially peeled from skin surface 1810, with at least one first type of microbe 1820 bound to at least one of the plurality of specific microbe-binding elements 1850. FIG. 18E shows peelable skin-covering material 1870 including at least one first type of microbe 1820 bound to at least one of the plurality of specific microbe-binding elements 1850. The at least one second type of microbe 1830 remains associated with skin surface 1810.

Figure 19:
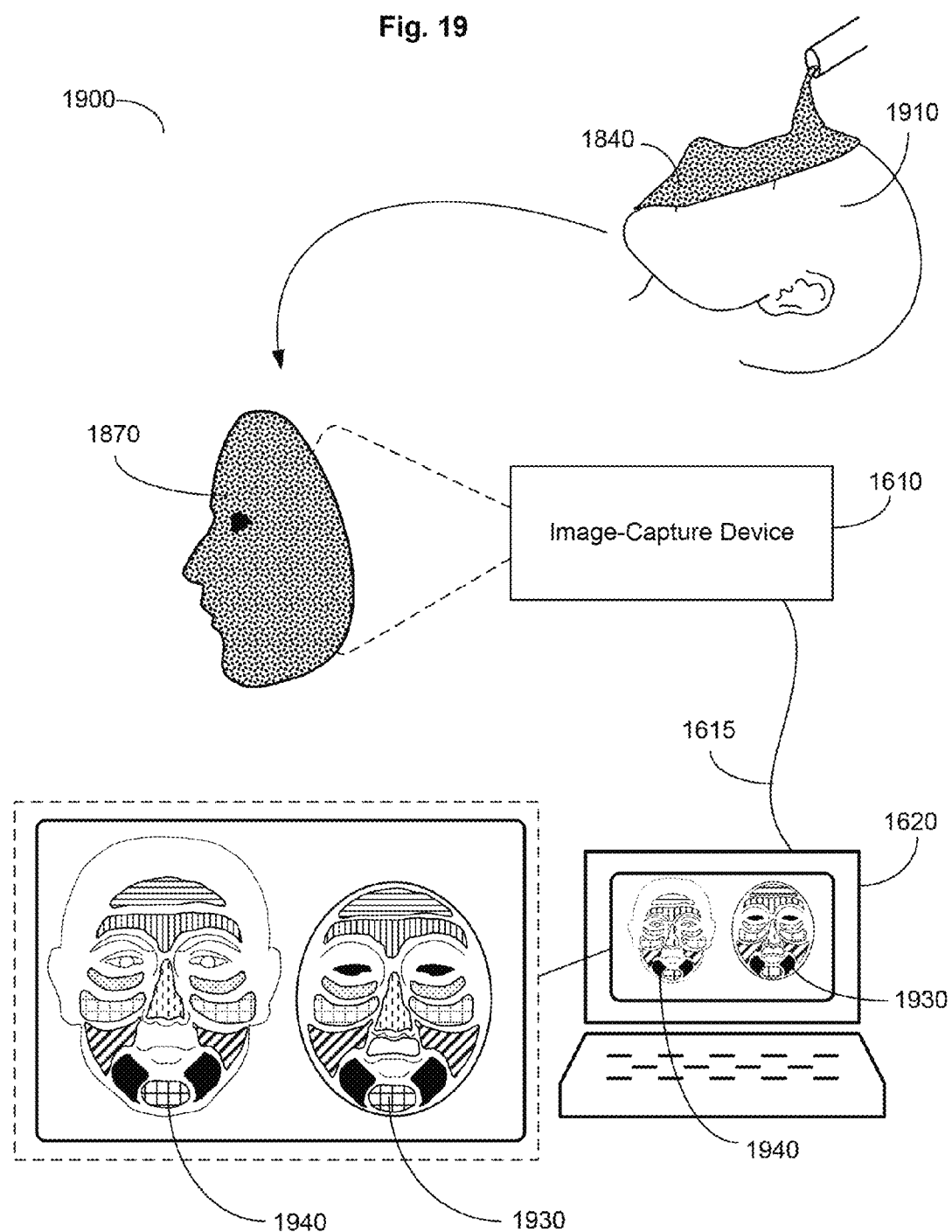
FIG. 19 is a schematic of a system for assessing microbiota including a peelable skin-covering material.

FIG. 19 illustrates aspects of a system including a peelable skin-covering material for assessing the microbiota of skin. System 1900 includes peelable skin-covering material 1870, image-capture device 1610, and computing device 1620. Peelable skin-covering material 1870 including a plurality of specific microbe-binding elements is formed from settable material 1840 and substantially conforms in shape to a topography of a skin surface of individual 1910. Image-capture device 1610 includes circuitry to capture at least one image of the inner surface of peelable skin-covering material 1870 and to transform the captured at least one image into a digital output including information associated with at least one property and a spatial distribution of at least one type of microbe bound to at least one of the plurality of specific microbe-binding elements. Computing device 1620 includes a processor and is operably coupled to image-capture device 1610 through communications link 1615. Computing device 1620 includes circuitry configured to receive digital output from image-capture device 1610 including the information associated with the at least one property and the spatial distribution of the at least one type of microbe bound to the at least one of the plurality of specific microbe-binding elements associated with the inner surface of peelable skin-covering material 1870, compare the at least one property of the at least one type of microbe with a database of reference microbe properties, and generate digital profile 1930 including the at least one property and the spatial distribution of the at least one type of microbe bound to the at least one of the plurality of specific microbe-binding elements. In an aspect, computing device 1620 further includes circuitry to generate a digital alignment 1940 of digital profile 1930 of the at least one type of microbe bound to the at least one of the plurality of specific microbe-binding elements associated with the inner surface of peelable skin-covering material 1870 with a digital image of a skin surface of individual 1910 covered by settable material 1840 prior to peeling. Digital alignment 1940 can be reported to a user of the system, e.g., individual 1910 or another individual, to aid in determining a recommended treatment regimen to maintain or alter the current types and spatial distribution of microbes on the skin surface of the individual.

FIG. 20 shows aspects of a method. The method includes receiving a digital output from an image-capture device, the digital output including information associated with at least one property and a spatial distribution of at least one type of microbe bound to at least one of a plurality of specific microbe-binding elements associated with an inner surface of a skin-covering material in block 2000; identifying the at least one type of microbe bound to the at least one of the plurality of specific microbe-binding elements by comparing the information associated with the at least one property of the at least one type of microbe with a database of reference microbe properties in block 2010; and reporting to a user an identification and spatial profile of the identified at least one type of microbe bound to the at least one of the plurality of specific microbe-binding elements associated with the inner surface of the skin-covering material in block 2020.

FIG. 21 shows further aspects of a method such as that shown in FIG. 20. Receiving a digital output from an image-capture device in block 2000 can further include receiving a digital output from at least one digital camera in block 2100 and/or at least one scanning device in block 2105. Receiving a digital output from at least one scanning device can further include receiving the digital output from at least one of an optical scanning device, a fluorescence scanning device, an acoustic scanning device, and/or an electromagnetic scanning device. Non-limiting examples of cameras and scanning devices have been described above herein.

The method includes identifying the at least one type of microbe bound to the at least one of the plurality of specific microbe-binding elements by comparing the information associated with the at least one property of the at least one type of microbe with a database of reference microbe properties. In an aspect, the method includes comparing at least one of an optical property of the at least one type of microbe as shown in block 2110. In an aspect, the method includes comparing at least one of a fluorescence property of the at least one type of microbe in block 2115. In an aspect, the method includes comparing at least one of an infrared spectral property of the at least one type of microbe in block 2120. In an aspect, the method includes comparing at least one of an acoustic property of the at least one type of microbe in block 2125. In an aspect, the method includes comparing at least one of a reflective property of the at least one type of microbe in block 2130. In an aspect, the method includes comparing at least one of a light scattering property of the at least one type of microbe in block 2135. In an aspect, the method includes comparing at least one of an opacity property of the at least one type of microbe in block 2140. In an aspect, the method includes comparing at least one of a size of the at least one type of microbe in block 2145. In an aspect, the method includes comparing at least one of a morphological property of the at least one type of microbe in block 2150. In an aspect, the method includes comparing at least one of a physical feature of the at least one type of microbe in block 2155.

FIG. 22 shows further aspects of a method such as shown in FIG. 20. In an aspect, the method includes generating a digital alignment of the spatial profile of the identified at least one type of specific microbe-binding element associated with the inner surface of the skin-covering material with a digital image of a skin surface of an individual covered by the inner surface of the skin-covering material; and reporting to the user a personalized microbe profile including the identification and the spatial profile of the identified at least one type of microbe one the skin surface of the individual in block 2200. In an aspect, reporting to the user includes providing a visual representation of the personalized microbe profile on a display in block 2210. In an aspect, reporting to the user includes providing a printout of the personalized microbe profile in block 2220. In an aspect, reporting to the user includes exporting the personalized microbe profile to a computing device as shown in block 2230.

In an aspect, the method further includes comparing the personalized microbe profile with a reference microbe profile, generating a recommended treatment regimen for the individual based on the comparison, and reporting the recommended treatment regimen to the user as illustrated in block 2240. In an aspect, comparing the personalized microbe profile with a reference microbe profile includes comparing with a reference microbe profile generated for the individual at a previous point in time in block 2250. In an aspect, comparing the personalized microbe profile with a reference microbe profile includes comparing with a reference microbe profile generated for one or more other individuals in block 2260.

In an aspect, the method includes generating a recommended treatment regimen without generating a digital alignment and creating a personalized microbe profile. In an aspect, the method includes generating a recommended treatment regimen based on the identification and the spatial profile of the at least one type of microbe bound to the at least one of the plurality of specific microbe-binding elements associated with the inner surface of the skin-covering material, and reporting the recommended treatment regimen to the user as illustrated in block 2270. Non-limiting examples of generating a recommended treatment regimen without generating a digital alignment and/or creating a personalized microbe profile have been described above herein.

FIG. 23 illustrates a method for generating a recommended treatment regimen. The method includes receiving a first digital output from an image-capture device, the first digital output including information associated with at least one property and a spatial distribution of a first set of one or more microbes bound at a first time point to one or more of a plurality of specific microbe-binding elements on an inner surface of a first skin-covering material in block 2300; receiving a second digital output from an image-capture device, the second digital output including information associated with at least one property and a spatial distribution of a second set of one or more microbes bound at a second time point to one or more of a plurality of microbe-binding elements on an inner surface of a second skin-covering material in block 2310; comparing the first digital output with the second digital output in block 2320; generating a recommended treatment regimen based on the comparison of the first digital output with the second digital output in block 2330; and reporting the recommended treatment regimen to a user in block 2340.

FIG. 24 shows a flowchart for a method for generating an identification and a spatial profile of at least one type of microbe on a skin surface of an individual. The method includes applying a skin-covering material to a skin surface of an individual, the skin-covering material including an inner surface and an outer surface, the inner surface substantially conforming in shape to a topography of the skin surface of the individual and including a plurality of at least one type of specific microbe-binding element in block 2400; removing the skin-covering material from the skin surface of the individual in block 2410; capturing at least one image of the inner surface of the skin-covering material with an image-capture device and transforming the captured at least one image into a digital output, the digital output including information associated with at least one property and a spatial distribution of at least one type of microbe bound to the at least one of the plurality of specific microbe-binding elements associated with the inner surface of the skin-surface material in block 2420; receiving the digital output from the scanning device, the digital output including information associated with at least one property and a spatial distribution of the at least one type of microbe bound to the at least one of the plurality of specific microbe-binding elements associated with the inner surface of the skin-covering material in block 2430; identifying the at least one type of microbe bound to the at least one of the plurality of specific microbe-binding elements by comparing the information associated with the at least one property of the at least one type of microbe with a database of reference microbe properties in block 2440; and reporting to a user an identification and spatial profile of the identified at least one microbe bound to the at least one of the plurality of specific microbe-binding elements associated with the inner surface of the skin-covering material in block 2450.

In an aspect, applying the skin-covering material to the skin surface of the individual includes applying the skin-covering material to the skin surface of the individual for a prescribed period of time. For example, the skin-covering material can be applied to the skin and immediately removed. For example, the skin-covering material can be applied to the skin for as little as about one second and as long as about one hour. In an aspect, the method includes applying the skin-covering material to the skin surface under pressure. In an aspect, the method includes applying the skin-covering material to the skin surface under vacuum. In an aspect, the method includes applying the skin-covering material to the skin surface in the presence of a stimulus, e.g., a thermal and/or chemical stimulus.

FIG. 25 shows further aspects of a method such as that shown in FIG. 24. In an aspect, the method further includes applying the plurality of specific microbe-binding elements to the inner surface of the skin-covering material prior to applying the skin-covering material to the skin surface of the individual in block 2500. For example, the plurality of specific microbe-binding elements can be formulated into a spray that is applied to the inner surface of the skin-covering material. For example, the plurality of specific microbe-binding elements can be formulated in a liquid or gel that is applied to the inner surface of the skin-covering material. In an aspect, the plurality of specific microbe-binding elements can be applied directly to the skin surface of the individual. For example, the specific microbe-binding element can include an antibody that specifically recognizes at least one type of microbe and is further modified with streptavidin to allow binding to a biotin-coated inner surface of a skin-covering material.

In an aspect, the method further includes separating the skin-covering material into one or more pieces along one or more tearable lines of perforations; and capturing at least one image of the inner surface of at least one of the one or more pieces of the skin-covering material in block 2510.

In an aspect, the method further includes generating a digital alignment of the spatial profile of the identified at least one type of microbe bound to the at least one of the plurality of specific microbe-binding elements associated with the inner surface of the skin-covering material with a digital image of the skin surface of the individual covered by the inner surface of the skin-covering material; and reporting to the user a personalized microbe profile including the identification and the spatial profile of the identified at least one type of microbe on the skin surface of the individual in block 2520.

In an aspect, the method further includes generating a recommended treatment regimen based on the identification and the spatial profile of the at least one type of microbe bound to the at least one of the plurality of specific microbe-binding elements associated with the inner surface of the skin-covering material; and reporting the recommended treatment regimen to the user in block 2530.

FIG. 26 illustrates aspects of a system including a signal-generating agent. System 2600 includes skin-covering material 1410, image-capture device 1610, computing device 1620, and signal-generating agent 2640. Non-limiting examples of signal-generating agents have been described above herein. FIG. 26A shows a cross-section of skin-covering material 1410 including inner surface 1420 and outer surface 1430. Inner surface 1420 further includes a plurality of specific microbe-binding elements 1440. FIG. 26A further shows a cross-section of skin surface 2610 including a first type of microbe 2620 and a second type of microbe 2630. FIG. 26B shows a cross-section of skin-covering material 1410 in close proximity to skin surface 2610. FIG. 26C shows a cross-section of skin-covering material 1410 on which the first type of microbe 2620 is bound to at least one of the plurality of specific microbe-binding elements 1440. The second type of microbe 2630 remains associated with skin surface 2610. FIG. 26D shows skin-covering material 1410 including the first type of microbe 2620 bound to at least one of the plurality of specific microbe-binding elements 1440 in contact with signal-generating agent 2640. Signal-generating agent 2640 binds directly to the first type of microbe 2620 bound to the specific microbe-binding element 1440. FIG. 26E shows image-capture device 1610 with circuitry configured to capture at least one image of inner surface 1420 of skin-covering material 1410 and including one or more signals 2670 emitted or reflected from signal-generating agent 2640 in response to directed energy 2660. Image-capture device 1610 includes circuitry for transforming one or more signals 2670 into a digital output for receipt by operably coupled computing device 1620 through communication link 1615.

FIG. 27 shows aspects of an article of manufacture for generating a personalized microbe profile. Article of manufacture 2700 includes non-transitory machine readable media bearing one or more instructions for assessing microbiota of skin in block 2710. The non-transitory machine readable media stores instructions and/or data for use in assessing microbiota of skin. Non-limiting examples of non-transitory machine readable media have been described above herein. Non-transitory machine readable media 2710 includes in block 2720, one or more instructions for receiving a digital output from an image-capture device, the digital output including information associated with at least one property and a spatial distribution of at least one type of microbe bound to at least one of a plurality of specific microbe-binding elements on an inner surface of a skin-covering material; in block 2730, one or more instructions for identifying the at least one type of microbe bound to the at least one of the plurality of specific microbe-binding elements by comparing the information associated with the at least one property of the at least one type of microbe with a database of reference microbe properties; in block 2740, one or more instructions for generating a digital alignment of the spatial distribution of the identified at least one type of microbe bound to the at least one of the plurality of specific microbe-binding elements on the inner surface of the skin-covering material with a digital image of a skin surface of an individual covered by the inner surface of the skin-covering material; in block 2750, one or more instructions for generating a personalized microbe profile from the digital alignment, the personalized microbe profile including the identity of the at least one type of microbe and the spatial distribution of the at least one type of microbe on the skin surface of the individual; in block 2760, one or more instructions for comparing the personalized microbe profile with a reference microbe profile; in block 2770, one or more instructions for generating at recommended treatment regimen for the individual based on the comparison of the personalized microbe profile with the reference microbe profile; in block 2780, one or more instructions for reporting to a user at least one of the personalized microbe profile or the recommended treatment regimen.

FIG. 28 illustrates aspects of a system including a skin-covering material with perforations and an image-capture device with a feeding mechanism. FIG. 28A illustrates aspects of a skin-covering material. Skin-covering material 2800 includes one or more tearable perforations 2810. In an aspect, one or more tearable perforations 2810 are added to the skin-covering material during manufacture, e.g., as part of a digital template from which the skin-covering material is manufactured through a 3D-printing process. In an aspect, one or more tearable perforations 2810 are added to the skin-covering material after manufacture, e.g., by punching a series of perforations into the skin-covering material. One or more tearable perforations 2810 are configured to separate skin-covering material 2800 into segments 2830*a*, 2830*b*, 2830*c*, 2830*d*. Each segment of skin-covering material 2810 is coded with a corresponding registration mark 2820*a*, 2820*b*, 2820*c*, and 2820*d*. In this example, the registration marks are represented by a bar code, with each segment having a unique bar code. FIG. 28B illustrates further aspects of skin-covering material 2800. Skin-covering material 2800 is separable into segment 2830*d* along tearable perforations 2810. Segment 2830*d* includes registration mark 2820*d*. In an aspect, skin-covering material 2800 including at least one type of microbe captured from a skin surface of an individual is separated into one or more segments for analysis by an image-capture device. FIG. 28C illustrates aspects of a system including skin-covering material 2800 and image-capture device 2840. Segment 2830*d* is fed into feeding mechanism 2850 of image-capture device 2840. Registration mark 2820*d* is "read" by a component of image-capture device 2840, e.g., a bar code scanner. Additional segments, e.g., 2830*c* are separable from skin-covering material 2800 and can also be subsequently fed into image-capture device 2840 for image analysis.

In an aspect, the one or more tearable perforations once torn allow a non-planar skin-covering material to lay substantially flat to aid in imaging the inner surface. For example, the one or more tearable perforations associated with a skin-covering material that substantially conforms in shape to a topography of a skin surface of an individual's face, e.g., a pre-formed rigid mask, can be used to flatten the mask for imaging. In an aspect, the computing device includes circuitry configured to reconstruct the three-dimensional aspects of the otherwise flattened skin-covering material.

Mouthpiece

In an aspect, the skin-covering material includes a mouthpiece configured for use in a mouth region of an individual. In an aspect, one or more surfaces of the mouthpiece substantially conform in shape to a topography of at least a portion of the mouth region of the individual. In an aspect, the at least a portion of the mouth region of the individual includes at least a portion of an oral mucosa, tooth, gingiva, tongue, or palate. For example, the mouthpiece can be configured for insertion into a mouth and to cover at least a portion of an individual's gingiva and teeth. In an aspect, the mouthpiece includes an inner surface defined as those portions of the mouthpiece, e.g., one or more surfaces of the mouthpiece, in contact with the surfaces of the mouth, e.g., the surfaces of the oral mucosa, teeth, gingiva, tongue, and/or palate. In an aspect, the skin-covering material can include a pre-formed mouthpiece.

In an aspect, the pre-formed mouthpiece substantially conforms in shape to the topography of at least a portion of the mouth region of the individual. In an aspect, the pre-formed mouthpiece is personalized to substantially conform in shape to the topography of at least a portion of the mouth region of the individual. For example, a digital three-dimensional representation of the mouth region of the individual may be used to digitally render a pre-formed mouth piece, which is then used as a template for manufacturing the pre-formed mouthpiece using a three-dimensional printer. In an aspect, the pre-formed mouthpiece is generated using one or more images captured using an image-capture device, e.g., a three-dimensional laser scanning system, to image the topography of the mouth region of the individual. Non-limiting examples of imaging systems for this purpose include Cadent iTero® (from Align Technology, Inc., San Jose, Calif.) and E4D Dentist System (from ED4 Technologies Richardson, Tex.). Computer-aided design software can be used to generate a digitally rendered model of the pre-formed mouthpiece from which the pre-formed mouthpiece can be formed using an additive or a subtractive manufacturing process. Non-limiting examples of modeling programs and manufacturing processes applicable to generating the pre-formed mouthpiece have been described above herein.

The pre-formed mouthpiece can be formed from any of a number of materials capable of being shaped, molded, or printed. Non-limiting examples of shapeable, moldable or printable materials include acrylic, nylon, plastic, ceramic, resin, rubber, epoxy, thermoplastic, polymer, photopolymer, polyurethane, gel, hydrogel, latex, or silicone. Other non-limiting examples of materials have been described above herein.

In an aspect, the skin-covering material can include a peelable mouthpiece. In an aspect, the peelable mouthpiece can include any of a number of shapeable or moldable materials applied to at least a portion of the mouth region of the individual and subsequently removed, i.e., peeled, leaving an imprint, wherein the imprint substantially conforms in shape to a topography of the at least one portion of the mouth region of the individual. In an aspect, the shapeable or moldable material may harden over an elapsed period of time or in response to exposure to air. In an aspect, the shapeable or moldable material may be hardened in response to electromagnetic energy, e.g., light of a specific wavelength, or in response to elevated temperature. In an aspect, the peelable mouthpiece is formed from a settable material configured to undergo a phase change from a liquid or gelled phase to a flexible solid phase in response to an applied stimulus. The applied stimulus can include at least one of exposure to air, a thermal stimulus, or an electromagnetic stimulus. For example, a peelable mouthpiece can be formed by adding a settable material, e.g., sodium alginate, into a dental or impression tray and inserting the tray with the settable material into the mouth of the individual and firmly pressing the tray into the teeth. Once the settable material has set, the dental or impression tray including the peelable mouthpiece is removed from the mouth. Non-limiting settable materials for use in generating a mouthpiece include sodium alginate, polyether, silicones, e.g., condensation-cured silicones and addition-cured silicones, polyvinyl siloxane, agar, or zinc oxide eugenol.

In an aspect, the mouthpiece, whether pre-formed or peelable from a settable material, further includes a medicament for treating a mouth condition. In an aspect, the medicament can be included as a layer on the one or more surfaces of the mouthpiece that come in contact with the surfaces of the mouth region. In an aspect, the medicament can be incorporated into the settable material. In an aspect, the medicament can be eluted by simple diffusion from a gel, e.g., a hydrogel, associated with the mouthpiece. Non-limiting examples of medicaments for treating a mouth condition include antibacterial agents, antifungal agents, antiviral agents, mouth deodorizer, fluoride treatment, probiotics, or prebiotics.

In an aspect, the mouthpiece includes at least one registration mark to register the mouthpiece to at least one landmark on one or more surfaces of the mouth region of the individual. The one or more landmarks on the one or more surfaces of the mouth region can include pigmented areas, dental topography, oral mucosa texture patterns, blemishes, anatomical features, or subsurface blood vessels. In an aspect, the one or more registration marks are incorporated into the manufacture of the mouthpiece based on a digital image of the mouth region including the one or more landmarks over which the mouthpiece will be placed.

In an aspect, the mouthpiece includes a microbe-capture region. The microbe-capture region is associated with one or more surfaces of the mouthpiece, e.g., one or more inner surfaces in direct contact with one or more surfaces of the mouth region of the individual. The microbe-capture region of the mouthpiece is configured to capture at least one type of microbe from the mouth region of the individual when the mouthpiece is placed in physical contact with the mouth region. Non-limiting examples of bacteria of the oral microbiota include *Streptococcus, Actinomyces, Veillonella, Fusobacterium, Porphromonas, Prevotella, Treponema, Nisseria, Haemophilis, Eubacteria, Lactobacterium, Capnocytophaga, Eikenella, Leptotrichia, Peptostreptococcus, Staphylococcus, Corynebacterium, Rothia, Selenomonas, Treponema, Propionibacterium*, and TM7 genera 1 and 5. See, e.g., Dewhirst et al. (2010) J. Bacteriology 192:5002-5017, which is incorporated herein by reference. Non-limiting examples of fungi of the oral microbiota include *Candida albicans, Aspergillus, Blastomyces dermatitidis, Cryptococcus neoformans*, and *Histoplasma capsulatum*.

Non-limiting examples of viruses of the oral microbiota include herpes simplex virus (HSV-1), human papillomavirus, coxsackievirus, and Paramyxoviridae viruses. Additional non-limiting examples of microbes have been described above herein. In an aspect, the microbe-capture region includes one or more materials configured to non-selectively capture a representative sample of microbes from the mouth region of an individual. Non-limiting examples of materials for use in a microbe-capture region have been described above herein.

In an aspect, the mouthpiece includes a plurality of specific microbe-binding elements. In an aspect, the specific microbe-binding element recognizes one or more components of at least one type of microbe. In an aspect, the specific microbe-binding element recognizes one or more components of a microbe, e.g., bacteria, a virus, a fungus, or a parasite, non-limiting examples of which have been describe above herein. Non-limiting examples of specific microbe-binding elements have been described above herein. In an aspect, the plurality of specific microbe-binding elements are incorporated into the mouthpiece. In an aspect, the plurality of specific microbe-binding elements are substantially uniformly distributed throughout the mouthpiece. For example, the plurality of specific microbe-binding elements may be uniformly dispersed in a liquid or gelled form during manufacture of the mouthpiece. In an aspect, the plurality of specific microbe-binding elements are substantially distributed along the inner surface of the mouthpiece, e.g., the one or more surfaces of the mouthpiece substantially conforming in shape to the topography of the mouth region of the individual. In an aspect, the plurality of specific microbe-binding elements are functionally attached to the inner surface of the mouthpiece. In an aspect, the plurality of specific microbe-binding elements are covalently attached to the inner surface of the mouthpiece. In an aspect, the plurality of specific microbe-binding elements are non-covalently attached to the inner surface of the mouthpiece.

In an aspect, the mouthpiece is deformable. In an aspect, the mouthpiece is deformable to facilitate imaging with an image-capture device. For example, the mouthpiece may be constructed of a material that is capable of being flattened for the purpose of performing imaging with a scanner, e.g., a flat-bed scanner. In an aspect, the mouthpiece can include one or more tearable perforations that allow the mouthpiece to be reshaped to facilitate imaging. For example, the mouthpiece can include one or more tearable or cuttable lines which when torn or cut allow the mouthpiece to be in a flattened state.

Figure 29:
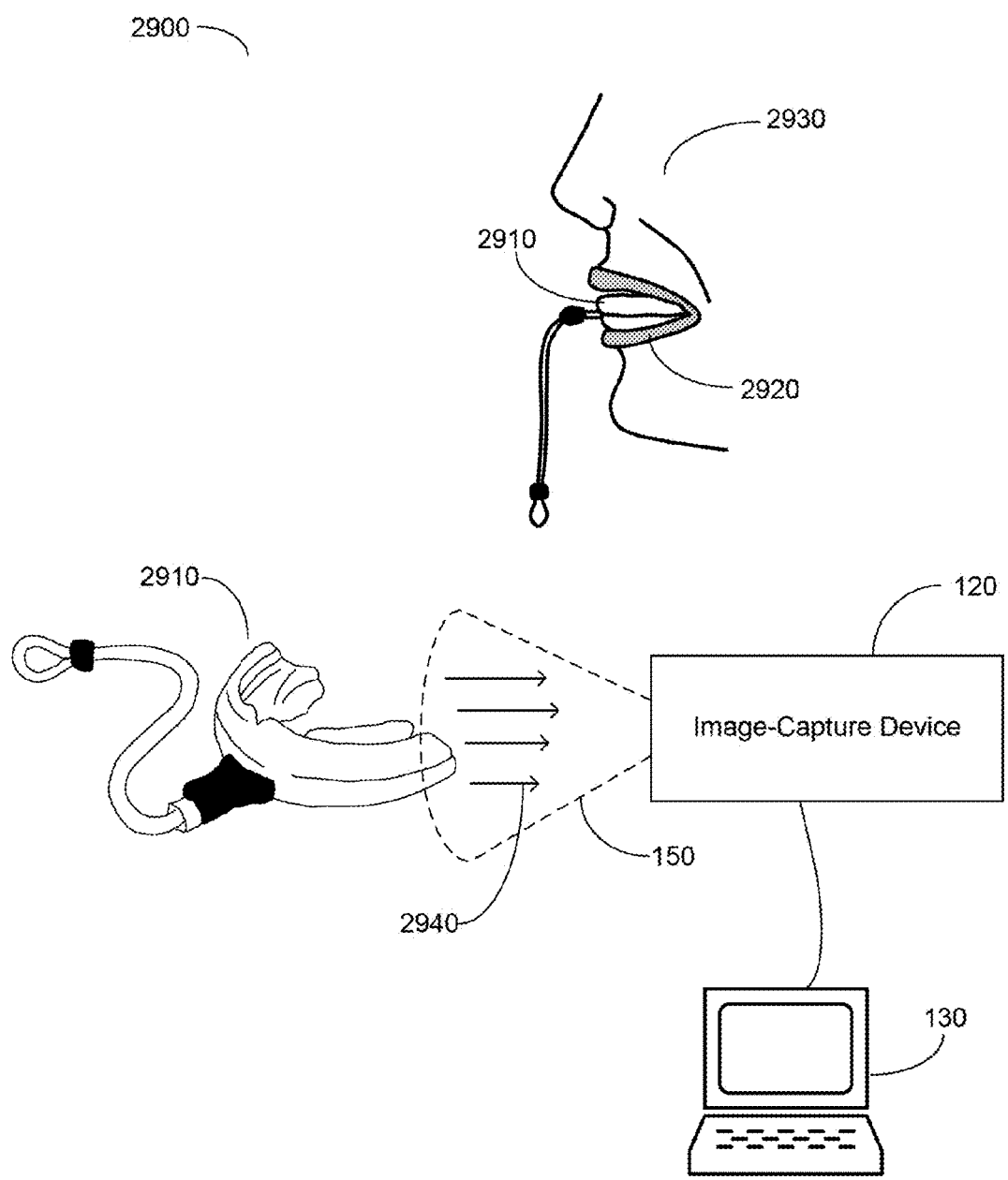
FIG. 29 illustrates aspects of a system for assessing microbiota of mouth.

In an aspect, the mouthpiece is part of a system for assessing microbiota of the mouth region. FIG. 29 illustrates aspects of a system including a mouthpiece. System 2900 includes mouthpiece 2910, image-capture device 120, and computing device 130. Mouthpiece 2910 is configured for insertion into mouth region 2920 of individual 2930. Mouthpiece 2910 includes an inner surface and an outer surface, wherein the inner surface includes one or more surfaces of the mouthpiece substantially conforming in shape to a topography of mouth region 2920 of individual 2930. The inner surface of mouthpiece 2910 includes a microbe-capture region and/or a plurality of specific microbe-binding elements. System 2900 further includes image-capture device 120 including circuitry to capture at least one image of the inner surface of mouthpiece 2910 and to transform the captured at least one image into a digital output including information associated with at least one property and a spatial distribution of at least one type of microbe bound to the microbe-capture region and/or at least one of the plurality of specific microbe-binding elements. In an aspect, one or more signals 2940 are emitted or reflected from the inner surface of mouthpiece 2910 in response to directed energy 150 from image-capture device 120. For example, one or more surfaces of mouthpiece 2910 can be imaged using a three-dimensional laser scanning system.

System 2900 further includes computing device 130 including a processor, computing device 130 operably coupled to image-capture device 120 through communications link 125. Computing device 130 includes circuitry configured to receive the digital output from the image-capture device including the information associated with the at least one property and the spatial distribution of the at least one type of microbe bound to the microbe-capture region and/or at least one of the plurality of specific microbe-binding elements; compare the at least one property of the at least one type of microbe with a database of reference microbe properties; and generate a digital profile including the at least one property and the spatial distribution of the at least one type of microbe bound to the microbe-capture region and/or at least one of the plurality of specific microbe-binding elements of mouthpiece 2910. In an aspect, computing device 130 further includes circuitry configured to generate a digital alignment of the digital profile of the at least one type of microbe bound to the microbe-capture region and/or the at least one of the plurality of specific microbe-binding elements associated with the inner surface of the mouthpiece with a digital image of the mouth region of the individual covered by the inner surface of the mouthpiece.

In an aspect, system 2900 further includes at least one signal-generating agent to associate with the at least one type of microbe bound to the microbe-capture region and/or at least one of the plurality of specific microbe-binding elements associated with the inner surface of the mouthpiece, the at least one signal-generating agent including at least one of a color-generating agent, a fluorescence-generating agent, or a luminescence-generating agent. Other non-limiting examples of signal-generating agents have been described above herein.

In an aspect, system 2900 further includes at least one of an enhancing component to enhance binding of the at least one type of microbe to the microbe-capture region and/or the at least one of the plurality of specific microbe-binding elements associated with the one or more surfaces of the mouthpiece, the at least one enhancing component includes at least one of a thermal component, a vacuum component, a humidity component, a pressure component, a skin-softener, a detergent, or a lysing compound.

In an aspect, a method of assessing microbiota of skin such as described in FIGS. 6 and 20 includes a method of assessing microbiota of the oral cavity. In an aspect, the method of assessing the microbiota of the oral cavity includes receiving a digital output from an image-capture device, the digital output including information associated with at least one property and a spatial distribution of at least one type of microbe captured on at least one surface of a mouthpiece, the at least one surface of the mouthpiece including a microbe-capture region and/or a plurality of specific microbe-binding elements; identifying the at least one type of microbe captured on the at least one surface of the mouthpiece by comparing the information associated with the at least one property of the at least one type of microbe with a database of reference microbe properties; and reporting to a user an identification and spatial profile of the identified at least one type of microbe captured on the at least one surface of the mouthpiece. In an aspect, the method further includes generating a recommended treatment regimen based on the identification and spatial profile of the at least one type of microbe captured on the surface of the mouthpiece; and reporting the recommended treatment regimen to the user. Non-limiting aspects of a treatment regimen for a mouth region include instructions for brushing techniques; type and use of toothpaste, fluoride, mouth rinses, flossing, antibacterial agents, anti-fungal agents, antiviral agents, probiotics, or prebiotics; and recommendation regarding seeing a care provider such as a dentist, periodontist, or oral surgeon.

In an aspect, the method of assessing microbiota of skin includes a method of assessing microbiota of the oral cavity. In an aspect, the method of assessing the microbiota of the oral cavity includes applying a mouthpiece to a mouth region of an individual, the mouthpiece including one or more surfaces substantially conforming in shape to a topography of at least a portion of the mouth region of the individual, the one or more surfaces including a microbe-capture region and/or a plurality of specific microbe-binding elements; removing the mouthpiece from the mouth region of the individual; capturing at least one image of the one or more surfaces of the mouthpiece with an image-capture device and transforming the captured at least one image into a digital output, the digital output including information associated with at least one property and a spatial distribution of at least one type of microbe bound to the one or more surfaces of the mouthpiece; receiving the digital output from the image-capture device including the information associated with the at least one property and the spatial distribution of the at least one type of microbe bound to the one or more surfaces of the mouthpiece; identifying the at least one type of microbe bound to the one or more surfaces of the mouthpiece by comparing the information associated with the at least one property of the at least one type of microbe with a database of reference microbe properties; and reporting to a user an identification and a spatial profile of the identified at least one type of microbe bound to the one or more surfaces of the mouthpiece. In an aspect, the method further includes generating a recommended treatment regimen based on the identification and the spatial profile of the at least one type of microbe bound to the one or more surfaces of the mouthpiece; and reporting the recommended treatment regimen to the user. In an aspect, the method further includes generating a digital alignment of the spatial profile of the identified at least one type of microbe bound to the one or more surfaces of the mouthpiece with a digital image of one or more surfaces of the mouth region of the individual covered by the mouthpiece; and reporting to the user a personalized microbe profile including the identification and spatial profile of the identified at least one type of microbe on the one or more surfaces of the mouth region of the individual.

In an aspect, the identity and spatial distribution of the at least one type of microbe on the one or more surfaces of the mouth region of the individual are indicative of a condition of the oral cavity, e.g., periodontal disease. For example, the amount of *Prevotella* at one site may indicate developing periodontal disease at that site, whereas an abundance of *Prevotella* at another site may indicate advanced disease at the second site. See, e.g., Liu et al. (2012) PLoS ONE 7(6):e37919, which is incorporated herein by reference. In an aspect, the identity and spatial distribution of the at least one type of microbe on the one or more surfaces of the mouth region of the individual can be used to correlate risk with systemic indications, e.g., cardiovascular disease, preterm birth, stroke, diabetes, pneumonia, or a disease of the central nervous system. See, e.g., Cockburn, et al. (2012) Investigative Genetics 3:19; Dewhirst et al. (2010) J. Bacteriology 192:5002-5017, which are incorporated herein by reference.

In an aspect, the method of assessing microbiota of skin at at least two different time points includes assessing microbiota of a mouth region of an individual at at least two different time points. In an aspect, the method includes receiving at first digital output from an image-capture device, the first digital output including information associated with at least one property and at spatial distribution of a first set of one or more microbes captured at a first time point on one or more surfaces of a first mouthpiece; receiving a second digital output from the image-capture device, the second digital output including information associated with at least one property and a spatial distribution of a second set of one or more microbes captured at a second time point on one or more surfaces of a second mouthpiece; comparing the first digital output with the second digital output; generating a recommended treatment regimen based one comparison of the first digital output with the second digital output; and reporting the recommended treatment regimen to a user.

FIG. 30 is a schematic of a system for assessing microbiota of skin. System 3000 includes image-capture device 3010, computing device 3020 including a processor and operably coupled to image-capture device 3010 through communication link 3015, and non-transitory machine readable media 3030, readable by the computing device and bearing one or more instructions for assessing the microbiota of a skin surface of an individual. Image-capture device 3010 includes circuitry to capture at least one image of an inner surface of a skin-covering material and to transform the captured at least one image into a digital output including information associated with at least one property and a spatial distribution of at least one type of microbe bound to the inner surface of the skin-covering material. Non-limiting examples of skin-covering materials as well as image-capture devices have been describe above herein. Computing device 3020 includes a processor, and is configured to receive the digital output from image-capture device 3010. Computing device 3020 is configured to read and process the one or more instructions from non-transitory machine readable media 3030. Non-limiting aspects of a computing device have been described in FIG. 2. Non-limiting examples of non-transitory machine readable media have been described above herein. Non-transitory machine readable media 3030 includes one or more instructions 3040 for receiving the digital output from the image-capture device, the digital output including information associated with the at least one property and the spatial distribution of the at least one type of microbe bound to the inner surface of the skin-covering material; one or more instructions 3050 for comparing the information associated with the at least one property of the at least one type of microbe bound to the inner surface of the skin-covering material with a database of reference microbe properties; one or more instructions 3060 for generating a microbe profile including the at least one property and the spatial distribution of the at least one type of microbe bound to the inner surface of the skin-covering material; one or more instructions 3070 for generating a recommended treatment regimen for the individual based on a comparison of the microbe profile with a reference microbe profile; and one or more instructions 3080 for reporting to a user at least one of the microbe profile or the recommended treatment regimen.

In an aspect, non-transitory machine readable media 3010 includes one or more instructions for identifying the at least one type of microbe bound to the inner surface of the skin-covering material by comparing the information associated with the at least one property of the at least one type of microbe with the database of reference microbe properties. In an aspect, the database of reference microbe properties is included in the non-transitory machine readable media.

In an aspect, non-transitory machine readable media 3010 includes one or more instructions for generating a digital alignment of the spatial distribution of the identified at least one type of microbe bound to the inner surface of the skin-covering material with a digital image of a skin surface of an individual covered by the microbe-capture region. In an aspect, non-transitory machine readable media 3010 can include one or more instructions for detecting one or more features depicted in the digital images, e.g., the physical landmarks, and match these features with features in the digital spatial profile, e.g., the registration marks. Non-limiting methods for registering images by matching features, for example, have been described above herein.

In an aspect, non-transitory machine readable media 3010 includes one or more instructions for generating a personalized microbe profile from the digital alignment, the personalized microbe profile including at least one of an identify of the at least one type of microbe, the spatial distribution of the at least one type of microbe on the skin surface of the individual, or the recommended treatment regimen; and one or more instructions for reporting the personalized microbe profile to the user. In an aspect, non-transitory machine readable media 3010 includes one or more instructions for reporting at least one of the personalized microbe profile or the recommended treatment regimen to a user that is a service provider, e.g., a medical practitioner or other provider who is performing the microbiota assessment.

In an aspect, non-transitory machine readable media 3010 includes one or more instructions for comparing the personalized microbe profile with a reference microbe profile generated for the individual at a previous point in time, e.g., at a young age, before the onset of a skin disorder, or before and/or after a treatment regimen to treat a skin disorder. In an aspect, non-transitory machine readable media 3010 includes one or more instructions for comparing the personalized microbe profile with a reference microbe profile generating for one or more other individuals, e.g., an average "normal" profile or the profile of an individual with a desirable microbe profile as exemplified by "healthy" looking skin.

The state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein can be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations can include software or other control structures. Electronic circuitry, for example, may have one or more paths of electrical current constructed and arranged to implement various functions as described herein. In some implementations, one or more media can be configured to bear a device-detectable implementation when such media hold or transmit a device detectable instructions operable to perform as described herein. In some variants, for example, implementations can include an update or modification of existing software or firmware, or of gate arrays or programmable hardware, such as by performing a reception of or a transmission of one or more instructions in relation to one or more operations described herein. Alternatively or additionally, in some variants, an implementation can include special-purpose hardware, software, firmware components, and/or general-purpose components executing or otherwise invoking special-purpose components. Specifications or other implementations can be transmitted by one or more instances of tangible transmission media as described herein, optionally by packet transmission or otherwise by passing through distributed media at various times.

Alternatively or additionally, implementations may include executing a special-purpose instruction sequence or otherwise invoking circuitry for enabling, triggering, coordinating, requesting, or otherwise causing one or more occurrences of any functional operations described above. In some variants, operational or other logical descriptions herein may be expressed directly as source code and compiled or otherwise invoked as an executable instruction sequence. In some contexts, for example, C++ or other code sequences can be compiled directly or otherwise implemented in high-level descriptor languages (e.g., a logic-synthesizable language, a hardware description language, a hardware design simulation, and/or other such similar mode(s) of expression). Alternatively or additionally, some or all of the logical expression may be manifested as a Verilog-type hardware description or other circuitry model before physical implementation in hardware, especially for basic operations or timing-critical applications. Those skilled in the art will recognize how to obtain, configure, and optimize suitable transmission or computational elements, material supplies, actuators, or other common structures in light of these teachings.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein can be implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the mechanisms of the subject matter described herein are capable of being distributed as a program product in a variety of forms, and that an illustrative embodiment of the subject matter described herein applies regardless of the particular type of signal bearing medium used to actually carry out the distribution.

In a general sense, those skilled in the art will recognize that the various embodiments described herein can be implemented, individually and/or collectively, by various types of electro-mechanical systems having a wide range of electrical components such as hardware, software, firmware, and/or virtually any combination thereof; and a wide range of components that may impart mechanical force or motion such as rigid bodies, spring or torsional bodies, hydraulics, electro-magnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs. Those skilled in the art will also appreciate that examples of electro-mechanical systems include but are not limited to a variety of consumer electronics systems, medical devices, as well as other systems such as motorized transport systems, factory automation systems, security systems, and/or communication/computing systems. Those skilled in the art will recognize that electro-mechanical as used herein is not necessarily limited to a system that has both electrical and mechanical actuation except as context may dictate otherwise.

In a general sense, the various aspects described herein can be implemented, individually and/or collectively, by a wide range of hardware, software, firmware, and/or any combination thereof and can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). The subject matter described herein can be implemented in an analog or digital fashion or some combination thereof.

Those skilled in the art will recognize that at least a portion of the systems and/or processes described herein can be integrated into an image processing system. A typical image processing system generally includes one or more of a system unit housing, a video display device, memory such as volatile or non-volatile memory, processors such as microprocessors or digital signal processors, computational entities such as operating systems, drivers, applications programs, one or more interaction devices (e.g., a touch pad, a touch screen, an antenna, etc.), control systems including feedback loops and control motors (e.g., feedback for sensing lens position and/or velocity; control motors for moving/distorting lenses to give desired focuses). An image processing system can be implemented utilizing suitable commercially available components, such as those typically found in digital still systems and/or digital motion systems.

Those skilled in the art will recognize that at least a portion of the systems and/or processes described herein can be integrated into a data processing system. A data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system can be implemented utilizing suitable commercially available components, such as those typically found in data computing/communication and/or network computing/communication systems.

Those skilled in the art will recognize that at least a portion of the systems and/or processes described herein can be integrated into a mote system. Those having skill in the art will recognize that a typical mote system generally includes one or more memories such as volatile or non-volatile memories, processors such as microprocessors or digital signal processors, computational entities such as operating systems, user interfaces, drivers, sensors, actuators, applications programs, one or more interaction devices (e.g., an antenna USB ports, acoustic ports, etc.), control systems including feedback loops and control motors (e.g., feedback for sensing or estimating position and/or velocity; control motors for moving and/or adjusting components and/or quantities). A mote system may be implemented utilizing suitable components, such as those found in mote computing/communication systems. Specific examples of such components entail such as Intel Corporation's and/or Crossbow Corporation's mote components and supporting hardware, software, and/or firmware.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory). A sale of a system or method may likewise occur in a territory even if components of the system or method are located and/or used outside the territory.

Further, implementation of at least part of a system for performing a method in one territory does not preclude use of the system in another territory.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "operably coupled to" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components can be referred to herein as "configured to," "configured by," "configurable to," "operable/operative to," "adapted/adaptable," "able to," "conformable/conformed to," etc. Those skilled in the art will recognize that such terms (e.g. "configured to") can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications can be made without departing from the subject matter described herein and its broader aspects and, therefore, the appended claims are to encompass within their scope all such changes and modifications as are within the true spirit and scope of the subject matter described herein.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

Various non-limiting embodiments are described herein as Prophetic Examples.

Prophetic Example 1

A Preformed Skin-Covering Material Including an Adhesive Microbe-Binding Region to Assess Microbiota of Skin Construction and use of a skin-covering material are described. The skin-covering material is constructed of a semi-rigid material to substantially conform in shape to the topography of an individual's face. A digitally rendered model of the skin-covering material is generated from one or more digital images of the skin surface of the individual's face. Briefly, two charge-coupled device cameras and a projector connected to a computer are used to scan the skin surface of the individual's face as described in Feng et al. *Brit. J. Oral Maxillofacial Surg.* (2010) 48:105-109, which is incorporated herein by reference. The individual's face is exposed to structured light to collect an optical representation of the body region by a point cloud of up to 300,000 points in three-dimensional coordinates. The three-dimensional coordinates are acquired by the computer and used to construct a digitally rendered model of the skin-covering material using a CAD/CAM software package, e.g., Geomagic Studio (Morrisville, N.C.).

The skin-covering material is formed from the digitally rendered model using a commercially available 3D printer. An example of a 3D printer appropriate for a physician's office, for example, includes the uPrint SE system (from, e.g., Stratasys, Eden Prairie, Minn.). In this example, software associated with the 3D printer system converts an STL format file containing data regarding the digitally rendered model of the skin-covering material into deposition paths that guide the extrusion head of the printer, printing the skin-covering material layer by layer. The skin-covering material, with an overall thickness of 3 mm, is produced from a thermoplastic material, e.g., acrylonitrile butadiene styrene (ABS). Several pre-formed skin-covering materials specifically designed for the individual can be printed and used at subsequent treatment appointments. Similarly, the information used to form the skin-covering material can be saved for printing additional skin-coverings in the future.

The inner surface of the skin-covering material is coated with a biocompatible silicone-based pressure sensitive adhesive to form a microbe-capture region. Dow Corning 7-9700 Soft Skin Adhesive (from, e.g., Dow Corning, Midland, Mich.) is a two-part platinum catalyzed silicone elastomer. Part A and part B are mixed in a 1:1 ratio and applied to the inner surface of the skin-covering material in a 0.1 mm to 0.5 mm coating. Curing of the adhesive occurs at room temperature but may be accelerated by application of heat. Uncured adhesive is removed with isopropyl alcohol.

The inner surface of the skin-covering material is placed in contact with the individual's face for 5-10 minutes with manually applied pressure, e.g., using hands to press the skin-covering material onto the skin surface. The skin-covering material with adhered microbes is removed from the skin surface and subjected to imaging with an image-capture device.

The inner surface of the skin-covering material is imaged using a fluorescence spectrometer including a krypton ion laser, a color CCD camera, and a long-pass filter (cutoff wavelength, 550 nm) as described by Koenig & Schneckenburg (in *J. Fluorescence* (1994) 4:17-40, which is incorporated herein by reference). The excitation wavelength from the krypton laser is 407 nm. Fluorescent spots or regions of yellow and red corresponding to autofluorescence peak emissions associated with bacteria, e.g., *Propionibacterium acnes*, of about 580-600, 620, and about 640 nm are imaged using the CCD camera. Autofluorescence peaks at about 430-450 nm associated with sloughed off skin cells (see, e.g., Meerwaldt et al. (2005) J. Am. Soc. Nephrol. 16:3687-3693, which is incorporated herein by reference) that may be bound to inner surface of the skin-covering material are filtered out by the long-pass filter.

The digital image information including the distribution of fluorescent spots is sent to a computing device operably linked to the fluorescence spectrometer. The computing device is equipped with software such as that described by Selinummi et al. to assess both the intensity of the fluorescence as well as the quantity of spots. See, e.g., Selinummi et al. (2005) BioTechniques 39:859-863, which is incorporated herein by reference. The spatial distribution of the fluorescent spots or regions is digitally overlaid with the corresponding digital image of the individual's face to create a personalized microbe profile for the individual. A color scale is used to highlight the abundance of the bacteria detected on the skin surface. The computing device compares the personalized microbe profile of the individual with a reference microbe profile of an "average" individual of matched gender, ethnicity, and age. The comparison reveals an above "normal" distribution of bacteria in the "T-zone" (forehead, nose, and chin), and the computing device generates a recommended treatment regimen including cleansing twice daily with a mild soap and use of a topical antibiotic cream, e.g., 1% Clindamycin lotion. A printout including the personalized microbe profile and the recommended treatment regimen is provided to the individual.

Prophetic Example 2

A Preformed Skin-Covering Material Including a Poly-L-Lysine Microbe-Capture Region for Assessing Microbiota of Skin Construction and use of a skin-covering material for assessing abundance and/or distribution of *Staphylococcus epidermidis* on the skin surface of an individual are described. The skin-covering material is constructed of a semi-rigid material to substantially conform in shape to the topography of an individual's face using a digitally rendered model of the skin surface of the individual as described in Example 1. In this example, the skin-covering material is formed from the digitally rendered model of the skin surface of the individual by a sintering manufacturing process using DuraForm PP 100 Plastic, a polypropylene-like plastic (from, e.g., 3D Systems, Corp., Rock Hill S.C.).

At least a portion of the inner surface of the skin-covering material, e.g., the portion corresponding to the forehead of the individual, is coated with a layer of poly-L-lysine (0.01% solution, Sigma-Aldrich, St. Louis, Mo.) to generate the microbe-binding region. See, e.g., Cowan et al. (2001) *Biotechnology Letters* 23:1235-1241, which is incorporated herein by reference. The poly-L-lysine solution is allowed to dry either at room temperature or at an elevated temperature, e.g., 37 degrees centigrade, to speed evaporation.

The skin surface of the individual's face is moistened with phosphate buffered saline and the skin-covering material applied to the skin surface. After about 10 minutes, the skin-covering material is removed from the skin surface and allowed to dry.

The inner surface of the skin-covering material is further treated with a signal-generating agent, e.g., a modified antibody that recognizes a specific bacteria. The skin-covering material is incubated for 30 minutes in a solution containing an antibody that recognizes *Staphylococcus epidermidis* (from Thermo Scientific Pierce, Rockford, Ill.). The skin-covering material is washed several times with a solution containing phosphate buffered saline and 1% Tween20. The skin-covering material is incubated for 30 minutes with a secondary antibody-horseradish peroxidase conjugate. The skin-covering material is washed several times with a solution containing phosphate buffered saline and 1% Tween. The skin-covering material is placed in a developing solution that includes hydrogen peroxide and 3,3',5,5'-tetramethylbenzidine (TMB) and allowed to incubate until a blue color emerges. The reaction can be stopped by placing the skin-covering material in an acidic stopping reagent.

The blue color associated with positive *Staphylococcus epidermidis* staining on the inner surface of the skin-covering material is imaged using a CCD camera and the one or more captured images transmitted to a computing device for further analysis. The computing device compares the intensity and spatial distribution of staining of the *Staphylococcus epidermidis* captured from the individual's skin with staining associated with a "normal" individual. The levels and distribution of *Staphylococcus epidermidis* are deemed by the computing device to fall below a "normal" threshold. A recommended treatment regimen is generated for the individual that includes a probiotic for topical application to the skin surface that includes *Staphylococcus epidermidis*. The recommended treatment regimen recommends applying the probiotic to the skin surface for a prescribed period of time, e.g., a month, and recommends performing an updated analysis of the skin surface of *Staphylococcus epidermidis* after completion of the recommended treatment to determine whether the abundance and/or distribution of *Staphylococcus epidermidis* on the skin surface has shifted closer to the norm. Once the updated analysis has been completed, the computing device updates the recommended treatment regimen to reflect any changes in the abundance and/or distribution of *Staphylococcus epidermidis* on the skin surface.

Prophetic Example 3

A Peelable Skin-Covering Material for Assessing Microbiota of Skin

Use of a peelable skin-covering material to assess microbiota of skin is described.

A settable material, e.g., gelatin, is prepared and applied to a skin surface of an individual. Briefly, 7 grams of gelatin, e.g., 1 0.25 ounce packet of non-flavored Knox® Gelatine (from Kraft Foods, Northfield, Ill.) is heated in the presence of 125 milliliters of water to completely dissolve the gelatin. The gelatin solution is allowed to cool for 20 minutes at 4 degrees centigrade. The gelatin solution is applied as a thin layer to the surface of the individual's skin and allowed to air dry for 15 to 30 minutes.

Once solidified, one or more registration marks can be added to the gelatin peelable skin-covering. Because the gelatin is translucent, registration marks can be placed on the gelatin using ink (e.g., fluorescent ink) pushed through the outer surface to the inner surface of the skin-covering over landmarks on the individual's face, e.g., freckles, moles, or other markings visible through the translucent gelatin. A digital image of the gelatin peelable skin-covering on the skin-surface of the individual is also captured, as in Prophetic Example 1, to document where the landmarks are on the skin surface relative to the registration marks. The gelatin peelable skin-covering material is then carefully peeled from the individual's skin, removing with it microbes associated with the skin surface.

The inner surface of the gelatin peelable skin-covering material is treated with acridine orange, a cell-permeant nucleic acid fluorescent cationic dye, to stain DNA and RNA of microbes associated with the gelatin. When bound to DNA, acridine orange exhibits an excitation maximum of 502 nm and an emission maximum at 525 nm (green). When bound to RNA, acridine orange exhibits excitation maximum of 460 nm (blue) and an emission maximum of 650 nm (orange/red).

A solution of acridine orange is prepared by adding 2 milligrams of acridine orange (Catalog # A1301 from Invitrogen, Carlsbad, Calif.) into 1 milliliter of distilled water. This solution is further diluted 1:100 in phosphate buffered saline. Alternatively, a solution of acridine orange is prepared by a 1:100 to 1:1000 dilution of a commercially available acridine orange solution (e.g., Acridine Orange Staining Solution, 1 mM, catalog #6130 from Immunochemistry Technologies, LLC, Bloomington, Minn.). The acridine orange solution is applied to the inner surface of the gelatin peelable skin-covering material, e.g., as a spray, and allowed to incubate for 5-10 minutes. The inner surface may be briefly rinsed with phosphate buffered saline to remove unincorporated acridine orange prior to imaging.

The inner surface of the gelatin peelable skin-covering material is illuminated with electromagnetic energy at 502 nm and green fluorescence at 525 nm is captured using a charge-coupled device. The information regarding the intensity and spatial distribution of the green fluorescence is transformed into a digital output and sent to a computing device for further processing. The digital output may also include green fluorescence associated with staining nuclei of any sloughed-off skin cells that are bound to the inner surface of the skin-covering material. The sloughed-off skin cells are differentiated from the bacterial cells based on the difference in size of the stained nuclei (5-10 microns in width or diameter) versus the stained bacteria (0.2-2 microns in width or diameter).

A specific type of microbe, e.g., *Staphylococcus aureus*, captured on the gelatin peelable skin-covering material can be assessed using a more specific signal-generating agent e.g., a direct or indirect fluorescently labeled antibody. Either before or after staining with acridine orange, the inner surface of the gelatin peelable skin-covering material is incubated with a biotin conjugated antibody that recognizes *Staphylococcus aureus* (from, e.g., Thermo Scientific Pierce Antibodies, Rockford, Ill.). After washing with phosphate buffered saline with 1% Tween-20, the skin-covering material is incubated with Cy5-labeled streptavidin (from, e.g., Life Technologies Invitrogen, Carlsbad, Calif.). Cy5 has an absorption maximum of 650 nm and an emission at 667 nm and can be excited with either a Mercury lamp or a Krypton/Argon laser at 647 nm and visualized as red fluorescence with a CCD camera.

The computing device includes an algorithm for assessing the size of the fluorescent areas and subtracting or recoloring, e.g., as blue, those areas consistent with fluorescence associated with the larger skin cells. The spatial distribution of the captured fluorescence is presented to the user on a display associated with the computing device. The captured fluorescence can also include fluorescence associated with staining a specific type of microbe, in this example *Staphylococcus aureus*, with a fluorescent dye, i.e., Cy5 (red fluorescence), that can be distinguished from the green fluorescence associated with acridine-orange. The computing device generates a digital alignment of the captured fluorescence with a digital image of the skin surface of the individual previously covered by the peelable skin-covering material. The image of the captured fluorescence is aligned based on aligning the fluorescent marks corresponding to the registration marks with the corresponding landmarks on the skin surface observed in the digital image of the skin surface. The computing device further generates a personalized microbe profile for the individual including a spatial distribution and relative abundance of acridine orange-stained microbes as well as the Cy5-stained *Staphylococcus aureus* on the skin surface of the individual. The computing device compares the personalized microbe profile for the individual with that of another individual, for example, an average gender- and age-matched "control," and generates a recommended treatment regimen. The personalized microbe profile is provided to the individual as either a color printout or transmitted to the individual's personal computing device for future access and viewing, and includes recommended cleansers, e.g., antibacterial soap, and non-comedogenic cosmetics based on the spatial distribution and relative abundance of the microbes detected on the skin surface.

Prophetic Example 4

A Preformed Skin-Covering Including a Plurality of Specific Microbe-Binding Antibodies for Use in Assessing Microbiota of Skin A preformed skin-covering material is formed using methods such as described in Example 1. In this example, the preformed skin-covering material is formed from PMMA (poly(methyl methacrylate)) with a 3D printer (e.g., Objet Connex 3D printer, from Stratasys Ltd. Minneapolis, Minn.) using a digitally rendered model of an individual's skin surface. The inner surface of the skin-covering material is subjected to reactive ion etching (RIE) using an inductively coupled oxygen plasma to generate a textured surface conducive to antibody binding. See, e.g., Rucker et al. (2005) Langmuir 21:7621-7625, which is incorporated herein by reference.

The textured inner surface of the preformed skin-covering material is incubated with antibodies against *Propionibacterium acnes* and antibodies against *Staphylococcus epidermidis*. Antibodies to *Propionibacterium acnes* can be generated from heat inactivated bacteria as described in Nakatsuji et al. (2008) J. Invest. Dermatol. 127:2451-2457, which is incorporated herein by reference. Antibodies against *Staphylococcus epidermidis* are obtained from a commercial source (e.g., Thermo Scientific Pierce Antibodies, Rockford, Ill.). The antibodies are prepared in an aqueous solution, e.g., phosphate buffered saline, and applied in sufficient volume to cover the entirety of the inner surface and allowed to dry for 1 hour. The inner surface is rinsed with phosphate buffered saline supplemented with 0.1% Tween 20 to remove non-adhered antibody.

The preformed skin-covering material including antibodies against *Propionibacterium acnes* and antibodies against *Staphylococcus aureus* is applied to a skin surface of an individual to selectively capture these bacteria from the skin surface. The skin-covering material is removed from the skin surface and subjected to fluorescence scanning to detect autofluorescence associated with either *Propionibacterium acnes* or *Staphylococcus epidermidis*.

To detect autofluorescence associated with *Propionibacterium acnes*, the inner surface of the skin-covering material is imaged using a fluorescence spectrometer including a krypton ion laser, a color CCD camera, and a long-pass filter (cutoff wavelength, 550 nm) as described by Koenig & Schneckenburg (in *J. Fluorescence* (1994) 4:17-40, which is incorporated herein by reference). The excitation wavelength from the krypton laser is 407 nm. Fluorescent spots or regions of yellow and red corresponding to autofluorescence peak emissions of about 580-600, 620, and about 640 nm are imaged using the CCD camera. To detect autofluorescence associated with *Staphylococcus epidermidis*, the inner surface of the skin-covering material is subjected to directed energy at 488-nm line from an Argon laser the resulting autofluorescence captured with a CCD camera through 530/430-nm bandpass.

The spatial distribution of the captured autofluorescence from *Propionibacterium acnes* and the spatial distribution of the captured autofluorescence from *Staphylococcus epidermidis* are provided to a user as a two color spatial profile, for example, red for *Propionibacterium acnes* and green for *Staphylococcus epidermidis*. A personalized microbe profile is also prepared for an individual by overlaying the spatial distribution of autofluorescence from each type of bacteria with a digital image of the skin surface. Fluorescent spots or regions captured by the image-capture device are digitally overlaid with the corresponding digital image of the individual's face. A color scale may be used to highlight the abundance of the bacteria detected on the skin surface. As above, the computing device compares the personalized microbe profile of the individual with reference microbe profiles to generate a recommended treatment regimen.

Prophetic Example 5

A Preformed Skin-Covering Material Including a Plurality of Specific Microbe-Binding Aptamers for Assessing Microbiota of Skin A preformed skin-covering material is formed from thermoplastic material, e.g., acrylonitrile butadiene styrene (ABS) using methods such as described in Example 1. The inner surface is further modified with poly(dimethylsiloxane) and cross-linkers to facilitate attachment of oligonucleotides as described in Blank et al. (2003) Proc. Natl. Acad. Sci., USA. 100:11356-11360, which is incorporated herein by reference. Briefly, the inner surface of the pre-formed skin-covering material is coated with a thin layer of PDMS (poly(dimethylsiloxane); Sylgard 184, Dow Corning, Midland, Mich.). The PDMS is derivatized with 3-aminopropyldimenthylethoxysilane to generate free amino groups to which a heterobifunctional cross-linking agent, e.g., NHS-PEG-COOH (from, e.g., Pierce, Rockford, Ill.), is attached to create a carboxy-modified inner surface.

One or more aptamers specific for binding at least one type of microbe, e.g., a type of bacteria, are generated as described by Chen et al. (see Chen et al. (2007) *Biochem. Biophys. Res. Commun.* 357:743-748, which is incorporated herein by reference). Briefly, aptamers against whole bacteria, e.g., whole *Propionibacterium acnes*, are isolated from a large library of $10^{14}$ to $10^{15}$ random oligonucleotides using an iterative in vitro selection procedure (SELEX). Whole *Propionibacterium acnes* are incubated with the oligonucleotides attached to beads, the beads washed, and the bound oligonucleotides amplified using the polymerase chain reaction (PCR) method. The amplified oligonucleotides are re-incubated with *Propionibacterium acnes* through multiple rounds of selection. One or more aptamers with specific affinity for *Propionibacterium acnes* are isolated after 8-10 rounds of selection. The resulting aptamers are further end-modified with an amine during the last PCR amplification.

To bind the amino-labeled aptamer to the carboxy-modified inner surface of the skin-covering material, 50 mM ethylene diaminecarbodiimide (EDC) is added to a solution of the aptamer before it is applied to the carboxy-modified inner surface. The skin-covering material is rinsed with a physiological buffer, e.g., phosphate buffered saline.

The skin surface of the individual is wetted with a buffered saline solution, e.g., phosphate buffered saline, and the skin-covering material including the plurality of aptamers configured to recognize and bind *Propionibacterium acnes* is placed on the wetted skin surface. After about 10 minutes of light pressure, e.g., applied with a hand, to ensure adequate contact between the inner surface of the skin-covering material and the skin surface, the skin-covering material is removed and subjected to fluorescence imaging.

To detect autofluorescence associated with *Propionibacterium acnes*, the inner surface of the skin-covering material is imaged using a fluorescence spectrometer including a krypton ion laser, a color CCD camera, and a long-pass filter (cutoff wavelength, 550 nm) as described by Koenig & Schneckenburg (in *J. Fluorescence* (1994) 4:17-40, which is incorporated herein by reference). The excitation wavelength from the krypton laser is 407 nm. Fluorescent spots or regions of yellow and red corresponding to autofluorescence peak emissions of about 580-600, 620, and about 640 nm are imaged using the CCD camera.

Alternatively, the inner surface of the skin-covering material can be incubated with a developing agent, e.g., acridine orange as described previously or a fluorescent antibody directed against *Propionibacterium acnes*. For the latter, an antibody that recognizes *Propionibacterium acnes* can be generated as described above herein and further modified with a fluorescent dye, e.g., fluorescein, using a commercially available kit (e.g., FluoroTag™ FITC Conjugation Kit, Sigma-Aldrich, St. Louis Mo.). The fluorescein-labeled antibody is then used to confirm the binding of *Propionibacterium acnes* to the *Propionibacterium acnes*-specific aptamers.

The fluorescence signal captured from the inner surface of the skin-covering material with the CCD camera is transformed into a digital output and sent to an operably linked computing device as described above herein. The fluorescence includes both the autofluorescence associated with *Propionibacterium acnes* as well as the fluorescence associated with the fluorescein-labeled antibody. A digital profile of the fluorescence is aligned with a digital image of the skin surface of the individual to generate a personalized microbe profile. The personalized microbe profile includes the type of microbe captured by the plurality specific microbe-binding aptamers, in this example *Propionibacterium acnes*, and spatial distribution of the microbe. The computing device generates a recommended treatment regimen for the individual as described above herein.

Prophetic Example 6

A Peelable Skin-Covering Material Including a Plurality of Specific Microbe-Binding Antibodies for Use in Assessing Microbiota of Skin Described is use of a peelable skin-covering material including a plurality of specific microbe-binding antibodies to assess *Candida albicans* population on a skin surface of an individual being treated with antibiotics. High doses of antibiotics can lead to reduced levels of healthy bacteria on skin allowing for increased fungal growth.

A settable material, e.g., polyvinyl alcohol, is prepared, mixed with the plurality of specific microbe-binding antibodies, and applied to a skin surface of an individual. A peelable skin-covering material is generated using polyvinyl alcohol as a settable material using methods such as described in U.S. Pat. No. 5,747,022; U.S. Patent Application 2005/0019291, which are incorporated herein by reference. Briefly, for a 100 ml solution of settable material, polyvinyl alcohol (10 µm; PVA-523, Sekisui America Corporation, Secaucus, N.J.) is heated in distilled water at 85° C. for 30 minutes. After cooling, sodium polyacrylate (1.5 µm; Rapithix A-60, Ashland Specialty Ingredients, Wayne, N.J.) is added to the solution along with glycerin (3 gm). Ethanol (10 ml) is added and the solution volume brought up to 100 ml with distilled water. Once the polyvinyl solution has cooled below about 37° C., polyclonal antibodies active against *Candida albicans* (from, e.g., Accurate Chemical & Scientific Co., Westbury, N.Y.) are added. The polyvinyl solution is cooled to about 27° C. The solution is slowly poured onto the skin within the area delineated by the surgical tape and allowed to solidify into a rectangular polyvinyl patch.

The polyvinyl patch is gently removed from the skin surface. The inner surface of the polyvinyl patch is imaged with directed electromagnetic energy at wavelengths of 465-495 nm to induce *Candida albicans* autofluoresces at an emission wavelength of 515-555 mm (see, e.g., Mateus et al. (2004) *Antimicrob. Agents Chemother.* 48:3358-3336, which is incorporated herein by reference). The autofluorescence is captured using an image-capture device and the resulting signal data is transformed into a digital output for receipt by a computing device.

Alternatively, a second antibody directed against *Candida albicans* and labeled with a fluorescent dye can be used to detect distribution of the fungus on the inner surface of the polyvinyl patch. For example, a polyclonal antibody conjugated to fluorescein (FITC, from, e.g., Thermo Scientific Pierce Antibodies, Rockford, Ill.) is applied to the inner surface of the polyvinyl patch for 30 minutes. Unbound antibody is removed from the polyvinyl patch by several rinses of phosphate buffered saline with 1% Tween (detergent). After rinsing, the inner surface of the polyvinyl patch is subjected to directed energy, e.g., an excitation wavelength of about 480 nm to cause the fluorescein associated with the antibody to fluoresce at about 520 nm. The resulting fluorescence signal is captured with the image-capture device and transformed into a digital output.

Alternatively, a fluorescent stain, e.g., Calcofluor White Stain, that binds cellulose and chitin in fungal cell walls, can be used to detect *Candida albicans* bound to the inner surface of the skin-covering material. In this case, the inner surface of polyvinyl patch is treated with equal part Calcofluor White Stain (from, e.g., Sigma Aldrich, St. Louis, Mo.) and 10% potassium hydroxide and then imaged using an excitation wavelength of about 350 nm and capturing a blue light emission at about 400 nm.

A computing device is used to receive the digital output from the image-capture device and to generate a digital profile including the spatial distribution of *Candida albicans* on the polyvinyl patch. The intensity of the signals received from any given spot on the polyvinyl patch may also be used to estimate the relative abundance of the fungus. The computing device generates a recommended treatment regimen including use of a fungicide, e.g., miconazole, to attenuate the *Candida albicans* population, use of a probiotic to add back normal, healthy bacteria to repopulate the skin surface, and/or a reduction in the use of antibiotics that are altering the normal bacterial population on the skin surface. The recommended treatment regimen may also include a recommended date in the future, e.g., 2-3 weeks in the future, for a repeat analysis of the skin surface.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A system for assessing microbiota of skin comprising:
a skin-covering material having an inner surface and an outer surface, the inner surface substantially conforming in shape to a topography of a skin surface of an individual and including associated thereto a plurality of specific microbe-binding elements;
an image-capture device including circuitry to capture at least one image of the inner surface of the skin-covering material and to transform the captured at least one image into a digital output including information associated with at least one property and a spatial distribution of at least one type of microbe bound to at least one of the plurality of specific microbe-binding elements; and
a computing device including a processor, the computing device operably coupled to the image-capture device and including circuitry configured to
receive the digital output from the image-capture device including the information associated with the at least one property and the spatial distribution of the at least one type of microbe bound to the at least one of the plurality of specific microbe-binding elements associated with the inner surface of the skin-covering material;
compare the at least one property of the at least one type of microbe with a database of reference microbe properties; and
generate a digital profile including the at least one property and the spatial distribution of the at least one type of microbe bound to the at least one of the plurality of specific microbe-binding elements.

2. The system of claim 1, wherein the computing device including the processor includes circuitry configured to identify the at least one type of microbe bound to the at least one of the plurality of specific microbe-binding elements based on comparison of the at least one property of the at least one type of microbe with the database of reference microbe properties.

3. The system of claim 1, wherein the digital profile includes an identification of the at least one type of microbe bound to the at least one of the plurality of specific microbe-binding elements based on comparison of the at least one property of the at least one type of microbe with the database of reference microbe properties.

4. The system of claim 1, wherein the skin-covering material includes one or more tearable lines of perforations.

5. The system of claim 1, wherein at least a portion of the inner surface of the skin-covering material includes a medicament.

6. The system of claim 1, wherein the skin-covering material includes a mouthpiece, the mouthpiece including one or more inner surfaces substantially conforming in shape to a topography of at least one portion of one or more surfaces of a mouth region of the individual, the one or more surfaces including the plurality of specific microbe-binding elements.

7. The system of claim 1, wherein the skin-covering material includes a pre-formed skin-covering material.

8. The system of claim 1, wherein the skin-covering material includes a peelable skin-covering material.

9. The system of claim 1, wherein the plurality of specific microbe-binding elements are incorporated into the skin-covering material.

10. The system of claim 1, wherein the plurality of specific microbe-binding elements are included in a renewable layer on the inner surface of the skin-covering material.

11. The system of claim 1, wherein at least one of the plurality of specific microbe-binding elements includes a specific microbe-binding ligand.

12. The system of claim 1, wherein the image-capture device includes at least one of a camera, a scanning device, or a spectrophotometer.

13. The system of claim 1, wherein the image-capture device includes a feeding mechanism and an imaging surface sized to accommodate at least a portion of the entirety of the skin-covering material, wherein the feeding mechanism is configured to feed in the at least a portion of the skin-covering material onto the image surface.

14. The system of claim 1, wherein the image-capture device and the computing device including the processor are incorporated into an interactive kiosk.

15. The system of claim 1, wherein the computing device includes circuitry configured to report to a user a personalized microbe profile, the personalized microbe profile including an identity of the at least one type of microbe and a spatial distribution of the identified at least one type of microbe on the skin surface of the individual.

16. The system of claim 1, wherein the computing device includes circuitry configured to generate a treatment recommendation based on an identity of the at least one type of microbe and a spatial distribution of the at least one type of microbe on the skin surface of the individual.

17. The system of claim 1, further comprising:
at least one signal-generating agent to associate with the at least one type of microbe bound to the at least one of the plurality of specific microbe-binding elements associated with the inner surface of the skin-covering material.

18. A method comprising:
receiving a digital output from an image-capture device, the digital output including information associated with at least one property and a spatial distribution of at least one type of microbe bound to at least one of a plurality of specific microbe-binding elements associated with an inner surface of a skin-covering material;
identifying the at least one type of microbe bound to the at least one of the plurality of specific microbe-binding elements by comparing the information associated with the at least one property of the at least one type of microbe with a database of reference microbe properties; and
reporting to a user an identification and spatial profile of the identified at least one type of microbe bound to the at least one of the plurality of specific microbe-binding elements associated with the inner surface of the skin-covering material.

19. The method of claim 18, further comprising:
generating a digital alignment of the spatial profile of the identified at least one type of microbe bound to the at least one of the plurality of specific microbe-binding elements associated with the inner surface of the skin-covering material with a digital image of a skin surface of an individual covered by the inner surface of the skin-covering material; and
reporting to the user a personalized microbe profile including the identification and the spatial profile of the identified at least one type of microbe on the skin surface of the individual.

20. The method of claim 19, further comprising:
comparing the personalized microbe profile with a reference microbe profile;
generating a recommended treatment regimen for the individual based on the comparison; and
reporting the recommended treatment regimen to the user.

21. The method of claim 18, further comprising:
receiving a digital output from the image-capture device, the digital output including information associated with at least one property and a spatial distribution of at least one type of microbe bound to at least one of a plurality of specific microbe-binding elements associated with an inner surface of a mouthpiece;
identifying the at least one type of microbe bound to the at least one of the plurality of specific microbe-binding elements by comparing the information associated with the at least one property of the at least one type of microbe with the database of reference microbe properties; and
reporting to the user an identification and spatial profile of the identified at least one type of microbe bound to the at least one of the plurality of specific microbe-binding elements associated with the inner surface of the mouthpiece.

22. The method of claim 18, further comprising:
receiving a first digital output from the image-capture device, the first digital output including information associated with at least one property and a spatial distribution of a first set of one or more microbes bound at a first time point to one or more of a plurality of specific microbe-binding elements on an inner surface of a first skin-covering material;
receiving a second digital output from the image-capture device, the second digital output including information associated with at least one property and a spatial distribution of a second set of one or more microbes bound at a second time point to one or more of a plurality of specific microbe-binding elements on an inner surface of a second skin-covering material;
comparing the first digital output with the second digital output;
generating a recommended treatment regimen based on the comparison of the first digital output with the second digital output; and
reporting the recommended treatment regimen to the user.

23. A method comprising:
applying a skin-covering material to a skin surface of an individual, the skin-covering material including an inner surface and an outer surface, the inner surface substantially conforming in shape to a topography of the skin surface of the individual and including associated thereto a plurality of specific microbe-binding elements;
removing the skin-covering material from the skin surface of the individual;
capturing at least one image of the inner surface of the skin-covering material with an image-capture device and transforming the captured at least one image into a digital output, the digital output including information associated with at least one property and a spatial distribution of at least one type of microbe bound to the at least one of the plurality of specific microbe-binding elements associated with the inner surface of the skin-covering material;
receiving the digital output from the image-capture device, the digital output including the information associated with the at least one property and the spatial distribution of the at least one type of microbe bound to the at least one of the plurality of specific microbe-binding elements associated with the inner surface of the skin-covering material;
identifying the at least one type of microbe bound to the at least one of the plurality of specific microbe-binding elements by comparing the information associated with the at least one property of the at least one type of microbe with a database of reference microbe properties; and
reporting to a user an identification and spatial profile of the identified at least one type of microbe bound to the at least one of the plurality of specific microbe-binding elements associated with the inner surface of the skin-covering material.

24. The method of claim 23, wherein applying the skin-covering material to the skin surface of the individual includes applying the skin-covering material to a mouth region of the individual, wherein the skin-covering material includes a mouthpiece.

25. The method of claim 23, further comprising:
separating the skin-covering material into one or more pieces along one or more tearable lines of perforations; and
capturing at least one image of the inner surface of at least one of the one or more pieces of the skin-covering material.

26. The method of claim 23, further comprising:
generating a digital alignment of the spatial profile of the identified at least one type of microbe bound to the at least one of the plurality of specific microbe-binding elements associated with the inner surface of the skin-covering material with a digital image of the skin surface of the individual covered by the inner surface of the skin-covering material; and
reporting to the user a personalized microbe profile including the identification and the spatial profile of the identified at least one type of microbe on the skin surface of the individual.

27. The method of claim 23, further comprising:
generating a recommended treatment regimen based on the identification and the spatial profile of the at least one type of microbe bound to the at least one of the plurality of specific microbe-binding elements associated with the inner surface of the skin-covering material; and
reporting the recommended treatment regimen to the user.

28. An article of manufacture comprising:
non-transitory machine readable media bearing one or more instructions for assessing microbiota of skin, the one or more instructions including
one or more instructions for receiving a digital output from an image-capture device, the digital output including information associated with at least one property and a spatial distribution of at least one type of microbe bound to at least one of a plurality specific microbe-binding elements on an inner surface of a skin-covering material;
one or more instructions for identifying the at least one type of microbe bound to the at least one of the plurality of specific microbe-binding elements by comparing the information associated with the at least one property of the at least one type of microbe with a database of reference microbe properties;
one or more instructions for generating a digital alignment of the spatial distribution of the identified at least one type of microbe bound to the at least one of the plurality of specific microbe-binding elements on the inner surface of the skin-covering material with a digital image of a skin surface of an individual covered by the inner surface of the skin-covering material;

one or more instructions for generating a personalized microbe profile from the digital alignment, the personalized microbe profile including the identity of the at least one type of microbe and the spatial distribution of the at least one type of microbe on the skin surface of the individual;

one or more instructions for comparing the personalized microbe profile with a reference microbe profile;

one or more instructions for generating a recommended treatment regimen for the individual based on the comparison of the personalized microbe profile with the reference microbe profile; and one or more instructions for reporting to a user at least one of the personalized microbe profile or the recommended treatment regimen.

* * * * *